US008041048B2

(12) United States Patent
Shim

(10) Patent No.: US 8,041,048 B2
(45) Date of Patent: Oct. 18, 2011

(54) ELECTROMAGNETICALLY-COUNTERED SPEAKER SYSTEMS AND METHODS

(76) Inventor: Youngtack Shim, Port Moody (CA)

( * ) Notice: Subject to any disclaimer, the term of this patent is extended or adjusted under 35 U.S.C. 154(b) by 522 days.

(21) Appl. No.: 12/318,538

(22) Filed: Dec. 31, 2008

(65) Prior Publication Data

US 2010/0166201 A1 Jul. 1, 2010

(51) Int. Cl.
*A61F 11/06* (2006.01)

(52) U.S. Cl. ........................ 381/71.1; 381/394; 381/396

(58) Field of Classification Search ................. 381/71.1, 381/394, 396
See application file for complete search history.

(56) References Cited

U.S. PATENT DOCUMENTS 6,108,433 A * 8/2000 Norris ........................... 381/399
7,058,195 B2 * 6/2006 Trandafir ....................... 381/409
7,162,048 B2 * 1/2007 Shima ........................... 381/334
7,225,895 B2 * 6/2007 Sahyoun ....................... 181/157
7,231,057 B2 * 6/2007 Kim et al. ..................... 381/396
7,330,705 B2 * 2/2008 Lee .............................. 455/117

* cited by examiner

*Primary Examiner* — Patricia Nguyen
(74) *Attorney, Agent, or Firm* — Stein McEwen, LLP

(57) ABSTRACT

The present invention relates to electromagnetically-countered speaker systems for generating acoustic sounds according to dynamic signals supplied thereto while minimizing irradiation of harmful electromagnetic waves therefrom. More particularly, the present invention relates to various speaker systems which do not include speaker magnets but include driver members for generating the sounds while emitting such harmful waves and counter members for generating magnetic forces for providing such sound while emitting counter electromagnetic waves capable of canceling at least a substantial portion of the harmful waves based on their configurational and phase characteristics. The present invention also relates to various speaker systems which do not include speaker magnets but include various electric and/or magnetic shields in addition to such drive and counter members. The present invention also relates to various methods of minimizing irradiation of the harmful waves of the speaker systems by the counter members, various methods of shielding such harmful waves by the electric and/or magnetic shields, and the like. The present invention further relates to various processes for providing such systems, counter members thereof, and electric and/or magnetic shields therefor.

20 Claims, 10 Drawing Sheets

ELECTROMAGNETICALLY-COUNTERED SPEAKER SYSTEMS AND METHODS

CROSS-REFERENCES TO RELATED APPLICATIONS

The present application claims an earlier filing date of the U.S. Utility patent application which is entitled "Generic electromagnetically-countered systems and methods," which was filed on Aug. 28, 2006, and which bears the Ser. No. 11/510,667, an entire portion of which is incorporated herein by reference. The present application also claims an earlier invention date of the Disclosure Document which is entitled the same, which was deposited in the U.S. Patent and Trademark Office (the "Office") on Jan. 3, 2007 under the Disclosure Document Deposit Program (the "DDDP") of the Office, and which bears the Ser. No. 610,795 an entire portion of which is incorporated herein by reference.

CROSS-REFERENCES TO RELATED APPLICATIONS

The present application is related to various patent applications which have been filed by the same Applicant. The first is the U.S. Utility patent application entitled "Shunted Magnet Systems and Methods," filed on Aug. 30, 2005, and bearing a Ser. No. 11/510,667.

The second is the U.S. Utility patent application entitled "Magnet-Shunted Systems and Methods," filed on Aug. 30, 2005, and bearing a Ser. No. 11/213,686. The third is the U.S. Provisional Patent Application entitled "Electromagnetic Shield Systems and Methods," filed on Oct. 3, 2005, and bearing a Serial Number U.S. Ser. No. 60/723,274, and the Disclosure Document entitled the same, deposited in the U.S. Patent and Trademark Office (the "Office") on Oct. 3, 2005 under the Disclosure Document Deposit Program (the "DDDP") of the Office, and bearing a Ser. No. 587,338. The fourth is the U.S. Utility patent application which is entitled "Electromagnetically-Shielded Heat Generating Systems and Methods," filed on Nov. 30, 2005 and bears a Ser. No. 11/289,693. The fifth is the U.S. Utility patent application which is entitled "Electromagnetically-Shielded Hair Drying Systems and Methods," filed on Nov. 30, 2005, and bears a Serial Number U.S. Ser. No. 11/289,578. The sixth is another U.S. Utility patent application entitled "Electromagnetically-Shielded Air Heating Systems and Methods," filed on Dec. 22, 2005 and bearing a Serial Number U.S. Ser. No. 11/313, 921. The next application is another U.S. Utility patent application entitled, "Electromagnetically-Shielded High-Temperature Systems and Methods," which was filed on Apr. 11, 2006 and bears a Serial Number U.S. Ser. No. 11/403,899. Tha last is another U.S. Utility patent application entitled, "Electromagnetically-Shielded Speaker Systems and Methods," which was filed on May 25, 2006 and bearing a Serial Number U.S. Ser. No. 11/440,135. All of these Applications and Documents will be referred to as the "co-pending Applications" hereinafter and all "co-pending Applications" are to be incorporated herein in their entirety by reference.

FIELD OF THE INVENTION

The present invention relates to electromagnetically-countered speaker systems for generating acoustic sounds according to dynamic signals supplied thereto while minimizing irradiation of harmful electromagnetic waves therefrom. More particularly, the present invention relates to various speaker systems which do not include speaker magnets but include driver members for generating the sounds while emitting such harmful waves and counter members for generating magnetic forces for providing such sound while emitting counter electromagnetic waves capable of canceling at least a substantial portion of the harmful waves based on their configurational and phase characteristics. The present invention also relates to various speaker systems which do not include speaker magnets but include various electric and/or magnetic shields in addition to such drive and counter members. The present invention also relates to various methods of minimizing irradiation of the harmful waves of the speaker systems by the counter members, various methods of shielding such harmful waves by the electric and/or magnetic shields, and the like. The present invention further relates to various processes for providing such systems, counter members thereof, and electric and/or magnetic shields therefor.

BACKGROUND OF THE INVENTION

It is now well established in the scientific community that electromagnetic waves with varying frequencies irradiated by various devices may be hazardous to human health. In some cases, such electromagnetic waves in mega- and giag-hertz range may be the main culprit, whereas the 60-hertz electromagnetic waves may be the main health concern in other cases. It cannot be too emphasized that it is very difficult to shield against magnetic waves of the 60-hertz electromagnetic waves which have wavelengths amounting to thousands of kilometers and that such 60-hertz magnetic waves are omnipresent in any corner of the current civilization.

However, intensity of such electromagnetic waves typically decreases inversely proportional to a square of a distance from a source of such waves to a target. Accordingly, potentially adverse effects from such electromagnetic waves may be minimized by maintaining a safe distance from such a source. Some electrical devices, however, are intended to be used in a close proximity to an user, where typical examples of such devices are hair dryers, hair curlers, electric mattresses or blankets, heating pads, and the like. Accordingly, the Applicant have disclosed numerous electromagnetically-shielded embodiments of such devices.

In contrary to the above devices, conventional electric speakers operate with electric currents having amplitudes lot less than those flowing in such devices. However, certain speakers included in earphones, headphones, cellular phones, and handsets of regular phones are to be disposed close to an ear of an user. Accordingly, although these speakers may emit the electromagnetic waves having less amplitudes, such speakers tend to irradiate the electromagnetic waves directly to brain cells in a close proximity thereto. In particular, the earphones are to be disposed into an ear canal of the ear so that the electromagnetic waves irradiated therefrom may reach the brain cells at a less distance and, therefore, with greater strengths. It is appreciated that the irradiation of such undesirable waves may not be prevented by operating the speakers by a DC current, for such speakers generate the sounds through fluctuating electric currents which inevitably irradiate such electromagnetic waves.

Electromagnetic waves have been proved to affect physiological activities of brain cells. For example, U.S. Pat. Nos. 4,940,453, 5,047,005, 5,061,234, 5,066,272, and 5,267,938 describe various apparatus and methods for stimulating the brain cells by impinging thereto electromagnetic waves. In more recent disclosures, both of U.S. Pat. No. 6,849,040 B2 issued to J. Ruohonen et al. on Feb. 1, 2005 and U.S. Pat. Appl. Pub. No. 2003/0073899 A1 of the same inventors published on Apr. 17, 2003 disclose dose-computing apparatus and method for determining effects of magnetic stimulation on human brain. However, the prior art does not provide any speakers capable of reducing irradiation of the harmful electromagnetic waves to the brain cells of the user.

For example, U.S. Pat. No. 6,590,539 B2 issued to H. Shinichi on Jul. 8, 2003 and another U.S. Pat. Appl. Pub. No. 2002/0060645 A1 of the same inventor published on May 23, 2002 describe dipole antennas of portable communication devices capable of reducing specific absorption rate or "SAR" of electromagnetic waves (to be abbreviated as "EM waves" hereinafter) emitted by such devices. U.S. Pat. No. 6,377,827 B1 issued to N. Rydbeck on Apr. 23, 2002 describes mobile communication devices with foldable antennas which may be disposed away from users during use to reduce the EM waves propagating to the brains of the users, while U.S. Pat. No. 6,246,374 B1 issued to A. Perrotta et al. on Jun. 12, 2001 discloses antenna assemblies of mobile communication devices with main and parasitic antennas disposed away from the users for reducing the EM waves during use. In addition, U.S. Pat. No. 5,586,168 issued to B. Bucalo et al. on Dec. 17, 1996 similarly discloses multi-piece cellular communication devices including antennas disposed toward and away from the rest of such devices and reducing such EM waves emitted thereby. Although these prior art devices may reduce a portion of such EM waves, they fail to reduce the EM waves irradiated to the user from their speakers.

In another class of examples, U.S. Pat. No. 6,418,273 B1 issued to J. Lubinski et al. on Jul. 9, 2002 describes portable CD player devices incorporating less semiconductor devices and minimizing irradiation of the EM waves, while U.S. Pat. No. 6,195,562 B1 issued to R. Pirhonen et al. on Feb. 27, 2001 discloses mobile communication devices capable of restricting maximum transmitting power thereof, thereby limiting power of their EM waves radiated thereby. U.S. Pat. No. 5,777,261 issued to J. Katz on Jul. 7, 1998 discloses mobile communication devices having cases capable of attenuating and diverting their EM waves irradiated thereby, and U.S. Pat. Appl. Pub. No. 2004/0170086 A1 of Y. Mayer et al. published on Sep. 2, 2004 describes microphone devices which may not employ any membranes. U.S. Pat. Appl. Pub. No. 2003/0002691 A1 of H. Ono et al. published on Jan. 2, 2003 describes earphones for portable communication devices capable of being attached thereto at distances and reducing irradiation of the EM waves, while U.S. Pat. Appl. Pub. No. 2002/0098862 A1 of E. Engstrom published on Jul. 25, 2002 describes mobile communication devices with speakers and antennas disposed away from heads of users for reducing exposure of the users to the EM waves from the speakers and antennas thereof. In addition, U.S. Pat. Appl. Pub. No. 2001/0034253 A1 of S. Ruschin published on Oct. 25, 2001 describes mobile communication devices with speakers and microphones coupled by optical paths for reducing radiation of EM waves. Although some of these prior art devices have recognized potential hazards from their speakers, none of the prior art devices teach how to reduce the irradiation of the EM waves from the speakers of such devices.

The prior art also discloses various acoustic paths capable of delivering sounds therethrough. Thus, U.S. Pat. No. 6,825,810 B2 issued to G. Ragner et al. on Nov. 30, 2004 and U.S. Pat. Appl. Pub. No. 2003/0132884 A1 of the same inventors published on Jul. 17, 2003 describe various mobile communication devices employing air channels to route sounds from their speakers to their earpieces, while U.S. Pat. No. 6,631,279 B2 issued to A. Rivera on Oct. 7, 2003 and U.S. Pat. Appl. Pub. No. 2002/0055374 A1 by the same inventor published on May 9, 2002 disclose assemblies of speakers and microphones of cellular communication devices including air tubes for transmitting and receiving acoustic waves for reducing irradiation of the EM waves generated thereby. U.S. Pat. No. 6,377,824 B1 issued to R. Ingbir et al. on Apr. 23, 2002 describes assemblies for cellular communication devices capable of converting electrical signals to acoustic signals to reduce the irradiation of the EM waves, while U.S. Pat. No. 6,181,801 B1 issued to S. Puthuffet al. on Jan. 30, 2001 describes earpieces of mobile communication devices disposed away therefrom through connectors to reduce exposure to the EM waves emitted thereby. In addition, U.S. Pat. Appl. Pub. No. 2004/0125979 A1 of J. Elidan et al. published on Jul. 1, 2004 discloses portable communication devices including tubes for transmitting acoustic waves to and from speakers and microphones and reducing the irradiation of the EM waves, while U.S. Pat. Appl. Pub. No. 2002/0048385 A1 of I. Rosenberg published on Apr. 25, 2002 describes cellular communication devices having assemblies of speakers and microphones coupled by air tubes and receiving and transmitting acoustic waves through the tubes for reducing the irradiation of the EM waves. Though these devices may reduce the exposure of the user to the EM waves, such may be achieved by increasing distances between the user and sources of the EM waves, not by decreasing amounts of the EM waves generated by such devices. In addition, incorporation of such air channels not only introduces mechanical noises to the sounds but also mandates use of additional components such as the air channels.

Various shields have also been described in the prior art so as to shield the user from the EM waves. For example, U.S. Pat. No. 6,855,883 B1 issued to H. Matsui on Feb. 15, 2005 describes shielding materials of electrically conductive fibers woven into a web and incorporated into a case of mobile communication devices, while U.S. Pat. No. 6,708,047 B1 issued to J. Miller et al. on Mar. 16, 2004 discloses annular radiation shields disposed around antennas of mobile communication devices. U.S. Pat. No. 6,314,277 B1 issued to Y-F Hsu et al. on Nov. 6, 2001 discloses radiation shields disposed on one side of an antenna of a mobile communication device for absorbing such EM waves, whereas U.S. Pat. No. 6,184,835 B1 issued to C. Chen et al. on Feb. 6, 2001 describes shielding covers for mobile communication devices for absorbing the EM waves radiated from their antennas. U.S. Pat. No. 6,137,998 issued to H. Holshouser et al. on Oct. 24, 2000 also discloses shields for antennas of cellular communication devices for reducing the EM waves radiated to their users, while U.S. Pat. No. 5,657,386 issued to J. Schwanke on Aug. 12, 1997 describes cellular communication devices including shields incorporated into their cases and absorbing or dispersing such EM waves. U.S. Pat. No. 5,406,038 issued to D. Reiff et al. on Apr. 11, 1995 describes speakers with diaphragms coated with metal layers to prevent transmission of the EM waves therethrough, while U.S. Pat. Appl. Pub. No. 2004/0219328 A1 of K. Tasaki et al. published on Nov. 4, 2004 discloses laminates of soft magnetic materials and insulators capable of being used as countermeasures against a specific absorption rate. In addition, U.S. Pat. Appl. Pub. No. 2004/0090385 A1 of R. Green published on May 13, 2004 describes cellular communication devices with shielding and reflecting layers for reflecting the EM waves away from users, U.S. Pat. Appl. Pub. No. 2002/0137473 A1 of D. Jenkins published on Sep. 26, 2002 discloses shields disposed over speakers of mobile communication devices and obstructing the EM waves irradiated by their speakers, and U.S. Pat. Appl. Pub. No. 2002/0097189 A1 of S. Coloney published on Jul. 25, 2002 describes mobile communication devices with shields which are disposed over speakers and antennas of the devices for reducing the EM waves emitted thereby. Although these shields claim to shield the user from the harmful EM waves, such shields may amount only to electric shields capable of shielding electric waves of the EM waves and may not at all shield magnetic waves of the EM waves.

Thus, there is an urgent need for electromagnetically-countered speaker systems capable of effectively reducing the irradiation of the harmful EM waves from their speakers without affecting the sounds. There also is a need for the speaker systems employing simple countermeasures capable of canceling at least a substantial portion of the harmful EM waves irradiated by their speakers without compromising their performances as well as complicating their configurations. There is another need for such systems which may not include any permanent magnets and, accordingly, may have a lighter weight. In addition, there is need for electric and magnetic shields for such speaker systems capable of shielding users from the harmful electric and magnetic waves of the EM waves. Moreover, there is a need for speaker systems including multiple mechanisms for shielding the users from the harmful EM waves irradiated by their speakers.

SUMMARY OF THE INVENTION

The present invention relates to electromagnetically-countered speaker systems for generating acoustic sounds according to dynamic signals supplied thereto while minimizing irradiation of harmful electromagnetic waves therefrom. More particularly, the present invention relates to various speaker systems which do not include speaker magnets but include driver members for generating the sounds while emitting such harmful waves and counter members for generating magnetic forces for providing such sound while emitting counter electromagnetic waves capable of canceling at least a substantial portion of the harmful waves based on their configurational and phase characteristics. The present invention also relates to various speaker systems which do not include speaker magnets but include various electric and/or magnetic shields in addition to such drive and counter members. The present invention also relates to various methods of minimizing irradiation of the harmful waves of the speaker systems by the counter members, various methods of shielding such harmful waves by the electric and/or magnetic shields, and the like. The present invention further relates to various processes for providing such systems, counter members thereof, and electric and/or magnetic shields therefor.

The electromagnetically-countered speaker systems of the present invention may be formed in various embodiments. For example and as described above, such speaker systems may be embodied as earphones or headphones which are to be disposed adjacent to or into the ears of the users. The speaker systems may also be incorporated into portable mobile or cellular phones, handsets of wired phones, and other communication devices such as walkie-talkies, and the like. The speaker systems may also be incorporated into other audio devices such as portable tape players, portable CD players, portable DVD players, portable mp3 players, and the like. Such speaker systems may also be used in conjunction with consoles of various audiovisual devices, e.g., as speakers for TVs, CD players, DVD players, game machines, computers, and other electric or electronic devices designed to output sound signals. Whether such devices are to be used proximate to or at preset distances from the users, the electromagnetically-countered speaker systems of this invention may effectively reduce the irradiation of the harmful EM waves to the user.

The electromagnetically-countered speaker systems of this invention may also be used in pairs or in greater numbers. Thus, multiple electromagnetically-countered speaker systems may be incased in a single case member, where each speaker system may be arranged to cancel at least a portion of such harmful EM waves generated by its wave source, where two or all speaker systems may be arranged to share a common counter member, a common electric and/or magnetic shield, and the like. In the alternative, multiple electromagnetically-countered speaker systems may be formed as separate articles, where such speaker systems may be disposed in a preset arrangement, where the speaker systems may be disposed in an arbitrary arrangement while manipulating its common counter member or their individual counter members to irradiate the counter EM waves capable of canceling at least a portion of the harmful waves.

Basic principles of the electromagnetically-countered speaker systems and counter members of the systems may be modified and applied to microphone systems. For example, such a microphone system may include at least one counter member which may be similar to that of the speaker system and irradiate counter waves capable of canceling at least a portion of harmful EM waves irradiated by one or more wave sources of the microphone system. In the alternative, the microphone system may include at least one electric shield or magnetic shield capable of absorbing and eliminating the electric and magnetic waves of such harmful waves, respectively. In addition, the above electromagnetically-countered microphone system and speaker system may be incased in a single case member and used as an assembly of a receiver and transmitter, where each of the systems may have its own counter member for canceling the portion of the harmful waves and/or where a single counter member may be arranged to cancel the portion of a sum of the harmful waves from both systems.

Accordingly, a primary objective of the present invention is to provide an electromagnetically-countered (to be abbreviated as an "EMC" hereinafter) speaker system which may generate sounds based on dynamic signals without incorporating any permanent magnet into its drive member which is also a source of harmful EM waves irradiated by such a system. Therefore, a related objective of this invention is to incorporate at least one first electromagnet in the drive member and at least one second electromagnet in a counter member of the system so that the drive member may generate the sounds due to repulsive and/or attractive forces provided by interacting dynamic magnetic fields generated by such electromagnets. Another related objective of this invention is to irradiate the counter EM waves by the second electromagnet of the counter member and then to cancel at least a substantial portion or only a portion of such harmful waves irradiated by the first electromagnet by such counter waves irradiated by the second electromagnet. Another related objective of this invention is to form and/or to dispose the first and second electromagnets to maximize an extent of canceling between the harmful and counter waves while optimizing an efficiency in converting such dynamic signals into the sounds. Another related objective of this invention is to provide an EMC system not including any permanent magnet and, therefore, having a lighter weight, smaller size, and the like.

Another objective of the present invention is to provide an EMC speaker system including in its drive member at least one permanent magnet which, however, is smaller than a counterpart found in a conventional speaker. Accordingly, a related objective of this invention is to provide a substantial or major portion of such repulsive and/or attractive forces from the interacting dynamic magnetic fields between the electromagnet, while providing at least but not amounting to a major portion of the forces from interaction between static magnetic fields of the permanent magnet and dynamic magnetic fields of the first electromagnet.

Another objective of the present invention is to form such an EMC speaker system capable of generating counter EM waves capable of canceling the desired portion of harmful waves irradiated by one of more sources of the system. Accordingly, a related objective of this invention is to provide an EMC speaker system for irradiating the counter waves capable of canceling the desired portion of the harmful waves emitted by a dynamic source such as a voice coil of the drive member of the system. Another related objective of this invention is to provide another EMC speaker system for irradiating the counter waves capable of canceling the desired portion of the harmful waves emitted by other parts of the system. Another related objective of this invention is to achieve all of such objectives without affecting sounds generated by the systems. Another related objective of this invention is to achieve all of such objectives without necessarily disposing the sources of the system farther away from an ear and/or head of an user during use of the system.

Another objective of the present invention is to provide an EMC speaker system which may be capable of manipulating configurational and/or phase characteristics of such counter waves to cancel the desired portion of the harmful waves. Therefore, a related objective of this invention is to provide an EMC speaker system capable of controlling amplitudes and/or phase angles of the counter waves to cancel the desired portion of the harmful waves. Another related objective of the present invention is to dispose an EMC speaker system in a location and/or an arrangement to emit such counter waves which are capable of canceling the desired portion of such harmful waves. Another related objective of this invention is to achieve all of the above objectives without affecting sounds generated by such systems.

Another objective of the present invention is to fabricate an EMC speaker system with such a counter member for irradiating such counter waves capable of canceling the desired portion of such harmful waves emitted by one or more wave sources of the system. Accordingly, a related objective of this invention is to provide a single counter member for a single wave source of the system and to irradiate such counter waves. Another related objective of this invention is to provide multiple counter members for multiple waves sources of the system so that each wave source may be provided with at least one counter member and that the desired portion of the harmful waves irradiated by each of such sources may be canceled by the counter waves irradiated by each counter member. Another related objective of this invention is to provide a less number of counter members than multiple wave sources of the system so that at least one of the counter members may irradiate the counter waves capable of canceling such a portion of a sum of the harmful waves irradiated by at least two of such sources.

Another objective of the present invention is to provide an EMC speaker system with at least one counter member for generating the counter waves while manipulating characteristics thereof for canceling the desired portion of such harmful waves. Thus, a related objective of this invention is to provide the counter member capable of irradiating the counter waves with desired amplitudes and/or phase angles for canceling the desired portion of such harmful waves. Another related objective of this invention is to dispose the counter member in a preset location of the system and/or in a preset arrangement with respect to the wave source in a preset relation such that the counter waves may cancel the desired portion of the harmful waves. Another related objective of such an invention is to provide the counter member with the dynamic signals which define preset amplitudes and which flow along a preset direction for irradiating the counter waves capable of canceling the desired portion of the harmful waves.

Another objective of the present invention is to provide at least one counter member capable of canceling the desired portion of harmful waves irradiated by the drive member and other sources of the system. Therefore, a related objective of this invention is to provide the counter member in a preset configuration which is same as, similar to or different from the drive member for local or global canceling of such waves, respectively. Another related objective of this invention is to enclose such a drive member by the counter member in a concentric arrangement. Another related objective of this invention is to dispose the counter and drive members side by side. Another related objective of this invention is to dispose the counter member proximal or distal to an user with respect to an user or to dispose the counter member flush with the drive member with respect to the user. Another related objective of this invention is to generate by the counter member such counter waves with amplitudes same as, similar to or different from those of the harmful waves for canceling a desired portion of the harmful waves. Another related objective of this invention is to implement at least one insert into the counter member to augment such counter waves generated by the counter member or, alternatively, to generate the counter waves of preset amplitudes with a smaller or more compact counter member.

Another objective of the present invention is to provide the counter member which defines a configuration for generating the counter waves for canceling a desired portion of the harmful waves. Accordingly, a related objective of this invention is to form the counter member in a configuration for generating the counter waves which are aligned with a propagation direction or axis of such harmful waves. Another related objective of this invention is to dispose and operate the counter member in an arrangement and/or in an orientation for aligning such counter waves with the propagation axis of the harmful waves. Another related objective of this invention is to implement the counter member in such a configuration, an arrangement, and/or an orientation for canceling only a desired portion or as much a portion of the harmful waves. Another related objective of this invention is to dispose such counter and drive members at a same distance, similar distances or different distances for canceling only the desired portion or as much a portion of the harmful waves. Another related objective of this invention is to provide one or more counter members to cancel such a portion of the harmful waves irradiated by one or more sources of the system. Another related objective of this invention is to include at least one insert into the counter member for augmenting the counter waves emitted by the counter member or, in the alternative, for generating the counter waves with preset amplitudes with a smaller or more compact counter member. Another related objective of this invention is to provide the counter member to have a composition which may be identical to, similar to or different from a composition of at least a portion of the drive member for canceling only the desired portion or as much a portion of the harmful waves.

Another objective of the present invention is to provide at least one counter member including a single counter unit or multiple identical, similar or different counter units therein. Therefore, a related objective of this invention is to include a single counter unit for generating the counter waves capable of canceling the portion of the harmful waves due to its relation to the drive member of such a system, amplitudes and/or directions of electric currents or signals flowing in the counter and drive members, and so on. Another related objective of this invention is to include multiple counter units for generating multiple sets of counter waves a sum of which is capable of canceling such a portion of such harmful waves emitted by one or multiple sources of the drive member due to such relations between multiple counter units and one or more sources, due to amplitudes and/or directions of the electric currents or signals flowing in the counter units and source, and so on. Another related objective of this invention is to form a single symmetric (or asymmetric) counter unit or to dispose the counter unit in a symmetric (or asymmetric) arrangement with respect to such a drive member for generating the counter waves. Another related objective of this invention is to form multiple symmetric (or asymmetric) counter units, to dispose the counter units in a symmetric (or asymmetric) arrangement with respect to each other, to dispose at least two of such multiple counter units in an arrangement symmetric (or asymmetric) to the drive member, and the like. Another related objective of this invention is to provide at least one of the counter units to define a composition which is identical to, similar to or different from a composition of at least a portion of the drive member for canceling only the desired portion or as much a portion of the harmful waves.

Another objective of the present invention is to provide at least one counter member in a shape capable of emitting the counter waves capable of canceling the portion of the harmful waves. Thus, a related objective of this invention is to fabricate the counter member into a shape of a wire, a strip, a sheet, a tube, a coil, a mesh, an array of one or more of such shapes, a combination of one or more of such shapes, a mixture of two or more of such shapes, and the like. Another related objective of this invention is to form the counter member to consist of a single counter unit of one of such shapes. Another related objective of this invention is to provide the counter member to include multiple counter units all of which may define the same shape and may also be disposed in a preset arrangement with respect to the source of the drive member. Another related objective of this invention is to provide the counter member to include multiple counter units at least two of which may have different shapes and may be disposed in a preset arrangement with respect to the source of the drive member. Another related objective of this invention is to provide the counter member with a single counter unit capable of canceling the portion of the harmful waves irradiated by only one or at least two of the sources of the drive member. Another related objective of this invention is to provide the counter member with at least two counter units each of which may cancel the portion of the harmful waves irradiated by each source of the drive member or all of which may cancel the portion of the harmful waves irradiated by a single source or multiple sources of the drive member. Another related objective of this invention is to dispose the counter unit(s) closer to, at the same distance from or farther away from the user than the drive member for manipulating amplitudes of the counter waves relative to those of such harmful waves. Another related objective of this invention is to dispose at least two counter units at the same distance or different distances from the user for canceling the preset portion or as much a portion of the harmful waves by the counter waves. Another related objective of this invention is to fabricate a symmetric (or asymmetric) counter unit or symmetric (or asymmetric) counter units and/or to arrange at least two of the counter units in an arrangement symmetric (or asymmetric) to at least a portion of the drive member to cancel the portion of the harmful waves by the counter waves. Another related objective of this invention is to form the counter unit(s) and/or to arrange the counter unit(s) based on various propagation characteristics of the harmful waves for effective canceling thereof.

Another objective of the present invention is to fabricate a speaker system including the drive member for emitting such harmful waves and at least one counter member for irradiating the counter waves capable of canceling such a portion of the harmful waves. Therefore, a related objective of this invention is to configure at least a portion of the counter member to conform (or to not conform) to at least a portion of such a drive member. Another related objective of this invention is to dispose at least a portion of the counter member in an arrangement conforming (or not conforming) to at least a portion of the drive member. Another related objective of this invention is to provide such a counter member to generate the counter waves which may define amplitudes and/or phase angles in preset relations to those of such harmful waves. Another related objective of this invention is to electrically couple at least a portion of the counter member with the drive member in a parallel mode, in a series mode or in a hybrid mode or, in the alternative, to not electrically couple the counter member with the drive member. Another related objective of this invention is to electrically couple the counter member with the drive member in a preset sequence so that the counter member may receive electric currents or signals before, after or simultaneously with the drive member.

Another objective of the present invention is to provide such a speaker system including such a counter member disposed in various strategic locations of the system. Thus, a related objective of this invention is to dispose at least a portion of the counter member over, on, below, and/or inside the case member, bracket, cone, suspension, spider, dust cap, and/or voice coil of the system. Another related objective of this invention is to mechanically couple such a counter member directly with such portions of the system or, alternatively, to mechanically couple the counter member with such portions through a separate coupler.

Another objective of the present invention is to form an EMC speaker system which includes at least two speakers and incorporates at least one counter member to cancel the desired portion of the harmful waves irradiated by multiple speakers of the system. Accordingly, a related objective of this invention is to form such a system including at least two speakers encased in a single case member and also including multiple counter members (or units) each irradiating such counter waves capable of canceling the portion of the harmful waves emitted by each speaker. Another related objective of this invention is to provide the system including at least two speakers encased in the single case member and including a single counter member (or unit) for irradiating the counter waves capable of canceling the desired portion of a sum of the harmful waves irradiated by all of such speakers. Another related objective of this invention is to provide such a system including multiple speakers individually encased in different case members and including multiple counter members (or units) each emitting the counter waves capable of canceling such a desired portion of the harmful waves irradiated by each speaker. Another related objective of this invention is to provide such a system also including multiple speakers encased in different case members and also including a single counter member (or unit) for generating the counter waves capable of canceling the desired portion of the sum of the harmful waves emitted by all of the speakers. Another related objective of this invention is to incorporate at least one counter member into each of various conventional speakers which may include one magnet and a set of voice coil, which may include an electrostatic arrangement, and the like.

Another objective of the present invention is to form an EMC speaker system including at least two speakers and canceling the desired portion of such harmful waves emitted by the drive members of such speakers. Therefore, a related objective of this invention is to provide such a system with the above counter member(s) for generating the counter waves capable of canceling the desired portion of the harmful waves locally or globally. Another related objective of this invention is to fabricate the system as an earphone or a headphone each including a pair of speakers to be disposed on each ear of the user and to implement the counter member to each of the speakers for canceling the portion of the harmful waves irradiated by each of the speakers. Another related objective of this invention is to fabricate the system as a microphone and to implement such a counter member to the source of such a system to cancel the portion of such harmful waves irradiated thereby. Another related objective of this invention is to provide the system as an assembly of a microphone and speaker and to implement thereinto the counter member(s) for generating the counter waves for canceling the desired portion of the harmful waves emitted by its speaker and microphone. Another related objective of this invention is to include the counter member into mobile or stationary communication devices and to generate the counter waves capable of canceling such a portion of the harmful waves irradiated by the speakers and/or microphones of such devices.

Another objective of the present invention is to fabricate various electric and magnetic shields for such EMC speaker systems and to respectively shield electric waves and magnetic waves of the harmful EM waves irradiated from their wave sources by such shields. Thus, a related objective of this invention is to provide such magnetic shields capable of absorbing and rerouting magnetic waves therealong, terminating or sinking such rerouted waves into a magnetic pole of a magnet, and the like. Another related objective of this invention is to provide such magnetic shields capable of confining a magnet field generated by such a magnet therearound within a preset distance, e.g., by shunting the magnetic fields closer thereto. Another related objective of this invention is to provide various electric shields similarly capable of absorbing and rerouting electric waves therealong, terminating or sinking such rerouted waves into ground or by self-cancellation, and the like.

Another objective of the present invention is to incorporate the above magnetic and/or electric shields into the EMC speaker systems and their drive members for accomplishing synergetic shielding against the harmful waves generated by the source. Therefore, a related objective of this invention is to provide the shields in various shapes or sizes to releasably or fixedly couple with various portions of the drive member or other parts of the system, to include such shields inside the drive member or such parts of the system, to form the drive member or such parts from a mixture including materials for such shields, and the like. Another related objective of this invention is to directly incorporate one or both of the shields onto or into the drive member or other parts of the system. Accordingly, another related objective of this invention is to provide such shields in various shapes and sizes to releasably couple with the drive member and/or such parts of the system, and/or to fixedly couple therewith or couple therewith through a coupler. Another related objective of this invention is to incorporate such shields into the drive member itself for shielding the waves emitted thereby. Another related objective of this invention is to incorporate such shields onto an exterior or interior of the system for shielding such harmful waves irradiated by its drive member. Thus, another related objective of this invention is to dispose such shields around, inside, on, or over one or more strategic locations of the system for effectively shielding such waves.

Another objective of the present invention is to provide an EMC speaker system incorporating the counter member as well as the magnetic and/or electric shields. Therefore, a related objective of this invention is to provide the system including one or more of such counter units for canceling some portions of the harmful waves irradiated by its drive member and further including such electric and/or magnetic shields for shielding remaining portions of such harmful waves.

Another objective of the present invention is to provide an EMC speaker system having at least one counter member capable of supplying beneficial EM waves to the user. Thus, a related objective of this invention is to configure the counter member to irradiate such beneficial EM waves in or around ranges of infrared rays (to be abbreviated as “IR rays” hereinafter) including far-infrared rays (or “FIR rays” hereinafter), medium-infrared rays (or “MIR rays” hereinafter), near-infrared rays (or “NIR rays” hereinafter), and so on. Another related objective of this invention is to configure the counter member to cancel portions of the harmful waves except those beneficial waves.

It is appreciated in all of such objectives that the counter members may not adversely affect normal operation of other portions of the speaker systems. For example, the dynamic magnetic fields generated by their counter members may effectively replace the static magnetic fields generated by the speaker magnets of the conventional speakers. In addition, incorporation of the counter members may neither affect quality of the sounds generated by the system.

It is to be understood that various counter members and/or their counter units of various EMC speaker systems of this invention may be incorporated into any electrical or electronic devices which may include at least one speaker and/or microphone and, accordingly, may irradiate such harmful EM waves which may include the electric waves (to be abbreviated as “EWs” hereinafter) and magnetic waves (to be abbreviated as “MWs” hereinafter) of frequencies of about 60 Hz and/or other EWs and MWs of higher frequencies. It is also appreciated that the EMC speaker systems of this invention may be incorporated into any portable or stationary electric and/or electronic devices including at least one speaker and/or microphone.

A variety of apparatus, method, and/or process aspects of the electromagnetically-countered speaker systems and various embodiments thereof are now enumerated. It is appreciated, however, that following system, method, and process aspects of the present invention may also be embodied in many other different forms and, thus, should not be limited to such aspects and/or their embodiments which are to be set forth herein. Rather, various exemplary aspects and their embodiments described hereinafter are provided such that this disclosure will be thorough and complete, and fully convey the scope of the present invention to one of ordinary skill in the relevant art.

In one aspect of the present invention, an electromagnetically-countered speaker system may be provided for generating audible sounds based on at least one dynamic signal supplied to at least two electromagnets while minimizing irradiation of harmful electromagnetic waves onto an user of the system.

In one exemplary embodiment of this aspect of the present invention, a system may include at least one drive member and at least one counter member. The drive member may be arranged to have a first electromagnet and a mobile cone coupling with the first electromagnet and to flow a first signal in the first electromagnet in a preset direction in order to generate therearound first dynamic magnetic fields. The counter member may be arranged to include a second electromagnet disposed in a preset relation to the first electromagnet and to flow a second signal in the second electromagnet in another preset direction so as to generate second dynamic magnetic fields therearound. The first and second magnetic fields may be arranged to exert therebetween repulsive and/or attractive forces based upon the relation and/or directions, where magnitudes of each of such forces may be in preset proportion to magnitudes of the first and/or second signals. The drive member may then be arranged to generate vibration of the cone based on the forces, to convert the vibration of the cone into the sounds, and to transmit the sounds onto the user while irradiating the harmful waves. The counter member may be arranged to emit counter electromagnetic waves capable of canceling at least a portion of the harmful waves based upon the relation and directions, thereby minimizing the irradiation. In one option, such a counter member may include at least one insert disposed in another preset relation with respect to the counter member and also including therein at least one ferromagnetic material, thereby augmenting the second magnetic fields when the second signal flows in the second electromagnet. In another option, the drive member may also have at least one permanent speaker magnet disposed in another preset relation to at least one of the electromagnets and exerting one of such repulsive and attractive forces which may be supplementary to the forces between the first and second magnetic fields.

In another exemplary embodiment of this aspect of the present invention, a system may include at least one drive member and at least one counter member. Such a drive member may be arranged to include a first electromagnet and a mobile cone coupling with the first electromagnet and to flow a first signal defining first dynamic characteristics along a preset direction in the first electromagnet in order to generate first dynamic magnetic fields therearound. The counter member may be arranged to have a second electromagnet disposed in a preset relation to the first electromagnet and to flow a second signal defining second characteristics which may be at least similar to those of the first signal in the second electromagnet in another preset direction in order to generate second dynamic magnetic fields therearound. Such first and second magnetic fields may further be arranged to exert therebetween repulsive and/or attractive forces based upon the relation and/or characteristics, where magnitudes of each of the forces may also be arranged to be in preset proportion to amplitudes of the first and/or second signals. The drive member may be arranged to generate vibration of the cone based upon the forces, to convert the vibration into the sounds, and to transmit the sounds to the user while emitting the harmful waves. The counter member may be arranged to emit counter electromagnetic waves capable of canceling at least a portion of the harmful waves based on the relation and characteristics, thereby minimizing the irradiation. In one option, the counter member may include at least one insert disposed in another preset relation to the counter member and including at least one ferromagnetic material, thereby augmenting the second magnetic fields when the second signals flow through the second electromagnet. In another option, the drive member may also include at least one permanent speaker magnet disposed in another preset relation to at least one of the electromagnets and exerting the repulsive and/or attractive forces which may be supplementary to such forces between the first and second magnetic fields.

In another aspect of the present invention, an electromagnetically-countered speaker system may also be provided for generating audible sounds from at least one dynamic signal while minimizing irradiation of harmful electromagnetic waves to an user of the system.

In one exemplary embodiment of this aspect of the present invention, a system may include at least one drive member and at least one counter member. The drive member may be arranged to flow a first signal therein along a first direction and to convert the first signal into the sounds by vibration of at least a portion thereof while irradiating the harmful waves to the user. The counter member may be arranged to be disposed based upon a preset relation to the drive member, to flow a second signal therein in a second direction, to provide at least a major portion of repulsive and/or attractive forces causing such vibration, and to irradiate counter electromagnetic waves capable of canceling at least a portion of the harmful waves based upon the relation and directions, thereby minimizing the irradiation.

In another exemplary embodiment of this aspect of the present invention, a system may include at least one drive member and at least one counter member. Such a case member may be arranged to define at least one opening therethrough, and this case member will now be referred to as the "case of the first type" or simply as the "first case member" hereinafter. The drive member may be arranged to be coupled to the case member and to include at least one cone and at least one voice coil coupling with the cone. Such a voice coil may be arranged to flow a first signal therein in a first direction and to define first dynamic magnetic field therearound in response to the first signal while irradiating such harmful waves. The counter member may be arranged to couple with the case and/or drive members in a preset relation, to flow therein a second signal along a second direction, to form second dynamic magnetic fields therearound, and to emit counter electromagnetic waves, where the second magnetic fields may be arranged to interact with the first magnetic fields and then to generate repulsive and/or attractive forces capable of causing vibration of the cone and also generating the sound. The counter waves may be capable of canceling at least a portion of the harmful waves based on the relation and directions, thereby minimizing the irradiation.

In another exemplary embodiment of this aspect of the present invention, such a system may include the first case member, at least one drive member, at least one of the above counter members, and at least one magnetic shield. The drive member may be arranged to be at least partially supported by the case member, to receive the signal, and to convert the signal to the sounds while emitting the harmful waves, where this drive member will be referred to as the "drive member of the first type" or simply as the "first drive member" hereinafter. In one example, the magnetic shield may be arranged to couple with the case and/or drive members, to absorb therein magnetic waves of the harmful waves, and to reroute the magnetic waves away from the user therealong, thereby minimizing the irradiation, where this magnetic shield will be referred to as the "magnetic shield of the first type" or simply as the "first magnetic shield" hereinafter. In another example, the magnetic shield may be arranged to couple with the case and/or drive members, to include at least one magnetically permeable path member and at least one magnet member which may define at least one magnetic pole thereon and may directly or indirectly couple with the path member, to absorb magnetic waves of such harmful waves in the path member, and to terminate such magnetic waves in the pole of the magnet member, thereby minimizing the irradiation. This magnetic shield will be referred to as the "magnetic shield of the second type" or simply as the "second magnetic shield" hereinafter. In another example, the magnetic shield may be arranged to couple to the case and/or drive members and to have at least one magnetically permeable path member, a magnet member defining at least one magnetic pole thereon and directly or indirectly coupling to the path member, and a magnetically permeable shunt member. Such a path member may be arranged to absorb magnetic waves of the harmful waves thereinto, the magnet member may be arranged to terminate the magnetic waves by the pole while generating a magnetic field therearound, and the shunt member may be arranged to confine the magnetic field from the magnet member closer thereto, thereby minimizing the irradiation. Such a magnetic shield will be referred to as the "magnetic shield of the third type" or simply as the "third magnetic shield" hereinafter.

In another exemplary embodiment of this aspect of the present invention, a system may include the first case member, the first drive member, at least one of the above counter members, at least one magnetic shield of the first type, second type or third type, and at least one electric shield which may be arranged to be electrically conductive, to be coupled to the case and/or drive members, and then to absorb therein electric waves of the harmful waves. Such an electric shield will be referred to as the "electric shield of the first type" or simply as the "first electric shield" hereinafter.

In another aspect of the present invention, an electromagnetically-countered speaker system may be provided for generating audible sounds based on at least one dynamic signal while minimizing irradiation of harmful electromagnetic waves to an user of the system. Such a system may include a drive member and a case member which may be arranged to form at least one opening therethrough. The drive member may be arranged to be coupled to the case member and to also include at least one movable part as well as at least one first electromagnet which may be arranged to form first dynamic magnetic fields therearound when the signal flows therein while irradiating the harmful waves. The drive member may then be arranged to convert the signal into the audible sounds by vibration of the movable part.

In one exemplary embodiment of this aspect of this invention, a system may further include at least one counter member which may be arranged to couple with the case and/or drive members. In one example, the counter member may have a configuration at least substantially similar to that of the first electromagnet. In another example, the counter member may have a configuration different from that of the first electromagnet. In both example, the counter member may also be arranged to define second dynamic fields capable of interacting with such first magnetic fields and generating repulsive and/or attractive forces therebetween primarily responsible for the vibration based at least partially on the configurations, and to irradiate counter electromagnetic waves which are capable of canceling at least a substantial (or only a selected) portion of the harmful waves, thereby minimizing the irradiation.

In another exemplary embodiment of this aspect of the present invention, a system may further include at least one counter member which may also be arranged to couple with the case and/or drive members in one arrangement of enclosing therein at least a portion of such a first electromagnet or in another axial and side-by-side (and/or lateral) arrangement with respect to at least a portion of such a first electromagnet. Such a counter member may further be arranged to define second dynamic fields capable of interacting with the first magnetic fields and generating repulsive and/or attractive forces therebetween primarily responsible for the vibration based at least partially on the arrangement, and to irradiate counter electromagnetic waves which are capable of canceling at least a substantial (or only a selected) portion of the harmful waves, thereby minimizing the irradiation.

In another exemplary embodiment of this aspect of the present invention, a system may further include at least one counter member which may also be arranged to couple with the case and/or drive members in one disposition closer to (or farther from) the user than the first electromagnet during use of the system, in another disposition flush with the first electromagnet during use of the system or in yet another disposition defining a distance from the user during use which may be at least similar to or different from another distance between the user and the first electromagnet. The counter member may also be arranged to define second dynamic fields capable of interacting with such first magnetic fields and generating repulsive and/or attractive forces therebetween primarily responsible for such vibration based at least partially upon the disposition, and to irradiate counter electromagnetic waves capable of canceling at least a substantial (or only a selected) portion of the harmful waves, thereby minimizing the irradiation.

In another exemplary embodiment of this aspect of the present invention, a system may further include at least one insert as well as at least one counter member which may be arranged to couple with the case and/or drive members in an arrangement of enclosing therein at least a portion of such a first electromagnet, to define second dynamic fields capable of interacting with such first magnetic fields and generating between the fields repulsive and/or attractive forces primarily responsible for the vibration, and to emit counter electromagnetic waves capable of canceling at least a substantial (or only a selected) portion of the harmful waves, thereby minimizing such irradiation. The insert may be arranged to include at least one material which may be magnetically soft or hard, to be disposed in or along the counter member, and to augment such second magnetic fields generated by the counter member, thereby enhancing the minimizing and decreasing a size of the counter member.

In another exemplary embodiment of this aspect of the present invention, a system may further include at least one of the above counter members as well as at least one magnetic shield of the first type, second type or third type, thereby minimizing the irradiation.

In another exemplary embodiment of this aspect of the present invention, a system may further include at least one of the above counter members, the first electric shield, and at least one magnetic shield of the first type, second type or third type, thereby minimizing the irradiation.

In another exemplary embodiment of this aspect of the present invention, a system may further include at least one counter member which may also be arranged to couple with the case and/or drive members in a preset relation, to form therearound second dynamic fields capable of interacting with the first magnetic fields and generating between the fields repulsive and/or attractive forces primarily responsible for the vibration, and to irradiate counter electromagnetic waves aligned with the harmful waves and also capable of canceling at least a substantial (or only a selected) portion of the harmful waves, thereby minimizing the irradiation.

In another exemplary embodiment of this aspect of the present invention, a system may further include at least one counter member which may also be arranged to couple with the case and/or drive members in a preset relation, to form therearound second dynamic fields capable of interacting with the first magnetic fields and generating between the fields repulsive and/or attractive forces primarily responsible for the vibration, and to irradiate counter electromagnetic waves. In one example, such a drive member may include a single source of the harmful waves, while the counter member may emit the counter waves which may match configurational and phase characteristics of the harmful waves and cancel at least a portion of the harmful waves for minimizing the irradiation. In another example, the drive member may include multiple sources of the harmful waves, while the counter member may emit the counter waves which may match configurational and phase characteristics of such harmful waves irradiated from one of the sources and cancel at least a portion of the harmful waves, thereby minimizing the irradiation. In another example, the drive member may include multiple sources of such harmful waves, while the counter member may emit the counter waves which match configurational and phase characteristics of a sum of the harmful waves irradiated from at least two of the sources and cancel at least a substantial (or only a selected) portion of the sum of the harmful waves, thereby minimizing the irradiation.

In another exemplary embodiment of this aspect of the present invention, a system may further include at least one counter member which may also be arranged to couple with the case and/or drive members in a preset relation and to receive the signal in a preset direction, where amplitudes of such a signal may be greater (or less) than those of the signal supplied to the first electromagnet, may be at least substantially similar to those of the signal supplied to the first electromagnet, or may instead be manipulated to match those of the signal supplied to the first electromagnet. The counter member may also be arranged to define second dynamic fields capable of interacting with such first magnetic fields and generating repulsive and/or attractive forces primarily responsible for the vibration between such fields, and to emit counter electromagnetic waves capable of canceling at least a substantial (or only a selected) portion of the harmful waves, thereby minimizing the irradiation.

In another aspect of the present invention, an electromagnetically-countered speaker system may be provided for generating audible sounds based on at least one dynamic signal while minimizing irradiation of harmful electromagnetic waves to an user of the system. Such a system may include a drive member and a case member which may be arranged to form at least one opening therethrough. The drive member may be arranged to be coupled to the case member and to also include at least one movable part and at least one first electromagnet having a first shape and flowing the signal therein in a first direction. The first electromagnet may also be arranged to define first dynamic magnetic fields therearound when the signal flows therein while irradiating the harmful waves and the drive member may be arranged to convert such a signal into the audible sounds by vibration of the movable part.

In one exemplary embodiment of this aspect of this invention, a system may further include at least one counter member which may also be arranged to couple with the case and/or drive members based on a preset relation and including a single counter unit which may be arranged to form second dynamic fields capable of interacting with the first magnetic fields and generating between the fields repulsive and/or attractive forces primarily responsible for the vibration, and then to irradiate counter electromagnetic waves capable of canceling at least a substantial (or only a selected) portion of the harmful waves at least partially based on the relation, thereby minimizing the irradiation.

In another exemplary embodiment of this aspect of the present invention, a system may further include at least one counter member at least one counter member coupling with at least one of the case and drive members and including a single counter unit which is arranged to flow the signal therein along a second direction, to define second dynamic fields capable of interacting with the first magnetic fields and generating between the fields at least one of repulsive and attractive forces preferentially responsible for the vibration, and to irradiate counter electromagnetic waves capable of canceling at least a substantial (or only a selected) portion of the harmful waves at least partially based on the directions, thereby minimizing the irradiation.

In another exemplary embodiment of this aspect of the present invention, a system may further include at least one counter member including multiple counter units each of which may be arranged to couple with the case and/or drive members based upon a preset relation and all of which may also be arranged to define second dynamic fields capable of interacting with the first magnetic fields and also generating between the fields repulsive and/or attractive forces primarily responsible for the vibration, and to irradiate counter electromagnetic waves capable of canceling at least a substantial (or only a selected) portion of the harmful waves at least partially based upon the relations, thereby minimizing the irradiation.

In another exemplary embodiment of this aspect of the present invention, a system may further include at least one counter member including multiple counter units each of which may be arranged to couple with the case and/or drive members and to flow such a signal along a second direction and all of which may be arranged to form therearound second dynamic fields capable of interacting with the first magnetic fields and generating between the fields repulsive and/or attractive forces preferentially responsible for the vibration, and to irradiate counter electromagnetic waves capable of canceling at least a substantial (or only a selected) portion of the harmful waves at least partially based upon the directions, thereby minimizing the irradiation.

In another exemplary embodiment of this aspect of the present invention, a system may further include at least one counter member coupling to the case and/or drive members and including a single counter unit which may be arranged to have a shape and an arrangement symmetric (or asymmetric) to itself and/or the drive member, to define second dynamic fields capable of interacting with the first magnetic fields and generating between such fields repulsive and/or attractive forces preferentially responsible for the vibration, and to irradiate counter electromagnetic waves capable of canceling at least a substantial (or only a selected) portion of the harmful waves at least partially based upon the shape and arrangement, thereby minimizing the irradiation.

In another exemplary embodiment of this aspect of the present invention, a system may further include at least one counter member including multiple counter units each of which may be arranged to couple with the case and/or drive members and which may be arranged to define shapes as well as arrangements symmetric (or asymmetric) to themselves and/or the drive member, to define second dynamic fields capable of interacting with the first magnetic fields and generating between the fields repulsive and/or attractive forces preferentially responsible for the vibration, and to irradiate counter electromagnetic waves capable of canceling at least a substantial (or only a selected) portion of the harmful waves at least partially based upon the relations, thereby minimizing the irradiation.

In another exemplary embodiment of this aspect of the present invention, a system may further include at least one counter member coupling with the case and/or drive members based on a preset relation and including at least one counter unit which may be arranged to have a composition similar to (or different from) that of the first electromagnet, to form second dynamic fields capable of interacting with the first magnetic fields and also generating between the fields repulsive and/or attractive forces mainly responsible for the vibration, and to emit counter electromagnetic waves capable of canceling at least a substantial (or only a selected) portion of the harmful waves at least partially based on the compositions, thereby minimizing the irradiation.

In another aspect of the present invention, an electromagnetically-countered speaker system may be provided for generating audible sounds based on at least one dynamic signal while minimizing irradiation of harmful electromagnetic waves to an user of the system, where the system may include a case member and a drive member which may be arranged to include a first electromagnet, to flow the signals in a first direction through the first electromagnet while irradiating the harmful waves, and to convert the signals into the sounds.

In one exemplary embodiment of this aspect of this invention, a system may further include at least one counter member which may be arranged to couple with the case and/or drive members and to include a single counter unit which may be arranged to have a curvilinear shape of a wire, a strip, a sheet, a tube, a coil and/or a mesh or, in the alternative, which may be arranged to define a shape of an array, a mixture, and/or a combination of at least two of a wire, a strip, a sheet, a tube, a coil, and a mesh. The counter member may be arranged to form second dynamic fields capable of interacting with the first magnetic fields and also generating between the fields repulsive and/or attractive forces primarily responsible for the vibration, and then to irradiate counter electromagnetic waves capable of canceling at least a substantial (or only selected) portion of the harmful waves at least partially based upon a relation between the counter and drive members as well as directions of the signals flowing in the counter and drive members, thereby minimizing the irradiation.

In another exemplary embodiment of this aspect of the present invention, a system may further include at least one counter member including multiple counter units each of which may be arranged to couple with the case and/or drive members and may have a shape of a wire, a strip, a sheet, a tube, a coil, and/or a mesh or, in the alternative, may have a shape of an array, mixture, and/or combination of at least one of a wire, a strip, a sheet, a tube, a coil, and a mesh. The counter member may also be arranged to define second dynamic fields capable of interacting with the first magnetic fields and also generating between the fields repulsive and/or attractive forces primarily responsible for the vibration, and then to emit counter electromagnetic waves capable of canceling at least a substantial (or only a selected) portion of the harmful waves at least partially based on a relation between the counter and drive members as well as directions of the signals flowing in the counter and drive members, thereby minimizing the irradiation, where at least two of the control units may be arranged to have identical (or different) shapes.

In another exemplary embodiment of this aspect of the present invention, a system may further include at least one counter member which may be arranged to be coupled to the case and/or drive members and to include a single counter unit which may be arranged to have a curvilinear shape of a wire, a strip, a sheet, a tube, a coil, a mesh, an array of at least two of the shapes, a mixture thereof, and/or a combination thereof. In one example, the drive member may include a single source of such harmful waves, while the counter unit may irradiate the counter waves matching configurational and phase characteristics of the harmful waves and capable of canceling at least a portion of the harmful waves, thereby minimizing the irradiation. In another example, the drive member may include multiple sources of the harmful waves, while the counter units may irradiate such counter waves matching configurational and phase characteristics of the harmful waves irradiated by one of the sources and capable of canceling at least a portion of the harmful waves, thereby minimizing the irradiation. In yet another example, the drive member may include multiple sources of the harmful waves, while such a counter units may irradiate the counter waves matching configurational and phase characteristics of a sum of the harmful waves irradiated from at least two of such sources and capable of canceling at least a substantial (or only a selected) portion of the sum of the harmful waves, thereby minimizing the irradiation.

In another exemplary embodiment of this aspect of the present invention, a system may include at least one counter member which may be arranged to couple with such case and/or drive members and to include multiple counter units each of which may also be arranged to define a curvilinear shape of a wire, a strip, a sheet, a tube, a coil, a mesh, an array of at least two of such shapes, a mixture thereof, and/or a combination thereof. In one example, the drive member may include a single source of the harmful waves, while the counter units may irradiate the counter waves a sum of which may be arranged to match configurational and phase characteristics of such harmful waves and capable of canceling at least a portion of such harmful waves, thereby minimizing the irradiation. In another example, the drive member may include multiple sources of the harmful waves, whereas at least two of the counter units may irradiate the counter waves a sum of which may also be arranged to match configurational and phase characteristics of the harmful waves emitted by at least one of the sources and also capable of canceling at least a substantial (or only a selected) portion of the harmful waves, thereby minimizing the irradiation. In another example, the drive member may include multiple sources of the harmful waves, and at least two of the counter units may irradiate the counter waves a sum of which may also be arranged to match configurational and phase characteristics of another sum of the harmful waves emitted by at least two of the sources and capable of canceling at least a substantial (or only selected) portion of the another sum of the harmful waves, thereby minimizing the irradiation.

In another exemplary embodiment of this aspect of the present invention, a system may include at least one counter member which may be arranged to be coupled to the case and/or drive members and to include a single counter unit which may be arranged to define a curvilinear shape of a wire, a strip, a sheet, a tube, a coil, a mesh, an array of at least two of the shapes, a mixture thereof, and/or a combination thereof, to be disposed closer to the user, farther away from the user, or at the same distance to the user with respect to the driver member during use, and to irradiate the counter waves matching configurational and phase characteristics of the harmful waves and capable of canceling at least a portion of the harmful waves, thereby minimizing the irradiation.

In another exemplary embodiment of this aspect of the present invention, a system may include at least one counter member which may be arranged to couple with such case and/or drive members and to include multiple counter units each of which may be arranged to define a curvilinear shape of a wire, a strip, a sheet, a tube, a coil, a mesh, an array of at least two of the shapes, a mixture thereof, and/or a combination thereof, to be disposed one of closer to the user, farther from the user, or at the same distance to the user from the driver member during use, and to emit the counter waves matching configurational and phase characteristics of such harmful waves and capable of canceling at least a portion of the harmful waves, thereby minimizing the irradiation.

In another exemplary embodiment of this aspect of the present invention, a system may include at least one counter member which may be arranged to couple with such case and/or drive members and to include a single counter unit which may be arranged to define a curvilinear shape of a wire, a strip, a sheet, a tube, a coil, a mesh, an array of at least two of the shapes, a mixture thereof, and/or a combination thereof, to define the shape and an arrangement symmetric (or asymmetric) to itself or the drive member, and to emit the counter waves matching configurational and phase characteristics of the harmful waves and also capable of canceling at least a portion of the harmful waves, thereby minimizing the irradiation.

In another exemplary embodiment of this aspect of the present invention, a system may include at least one counter member which may be arranged to couple with such case and/or drive members and to include multiple counter units each of which may be arranged to define a curvilinear shape of a wire, a strip, a sheet, a tube, a coil, a mesh, an array of at least two of the shapes, a mixture thereof, and/or a combination thereof and at least two of which may be arranged to define the shapes and the arrangements symmetric (or asymmetric) to themselves and/or drive member and to emit such counter waves matching configurational and phase characteristics of the harmful waves and also capable of canceling at least a portion of the harmful waves, thereby minimizing the irradiation.

In another exemplary embodiment of this aspect of the present invention, a system may include at least one counter member which may be arranged to couple with such case and/or drive members and to have at least one counter unit which may be arranged to define a curvilinear shape of a wire, a strip, a sheet, a tube, a coil, a mesh, an array of at least two of the shapes, a mixture thereof, and a combination thereof and to emit such counter waves matching patterns of propagation of the harmful waves and also capable of canceling at least a substantial (or only a selected) portion of the harmful waves, thereby minimizing the irradiation.

In another aspect of the present invention, an electromagnetically-countered speaker system may be provided for generating audible sounds based on dynamic signals which may flow in at least one first electromagnet and at least one second electromagnet while minimizing irradiation of harmful electromagnetic waves onto an user thereof.

In one exemplary embodiment of this aspect of the present invention, a system may include at least one drive member and at least one counter member. Such a drive member may include the first electromagnet which may be arranged to have a first configuration (or arrangement) and to include a movable part, whereas the counter member may include the second electromagnet which may be arranged to be disposed in a preset relation with respect to the drive member and to have a second configuration (or arrangement). The electromagnets may then be arranged to define repulsive and/or attractive magnetic fields therebetween in response to such signals and based upon the relation, to generate repulsive and/or attractive forces from such magnetic fields, and to generate the sounds by movement of the movable part while irradiating such harmful waves. Such a counter member may be arranged to emit counter electromagnetic waves capable of canceling at least a substantial (or only a selected) portion of the harmful waves at least partially based on the configurations (or arrangement) and relation, thereby minimizing the irradiation.

In another exemplary embodiment of this aspect of the present invention, a system may include at least one drive member and at least one counter member. The drive member may be arranged to include the first electromagnet and at least one movable part and to flow first signal of first amplitudes through the first electromagnet along a first direction. Such a counter member may be arranged to be incorporated in a preset relation to the drive member, to include the second electromagnet, and to flow therethrough second signal defining second amplitudes in a second direction. In one example, such electromagnets may be arranged to define repulsive and/or attractive magnetic fields therebetween in response to the signals and based on such a relation and/or directions, to generate repulsive and/or attractive forces from such magnetic fields, and to generate the sounds by movement of the movable part while irradiating such harmful waves, where these electromagnets will now be referred to as the "electromagnets of the first type" or as the "first electromagnets" hereinafter. In another example, the electromagnets may be similar to the above first electromagnets, except that the electromagnets may operatively couple to each other in a series mode, parallel mode or hybrid mode. In another example, the electromagnets may be similar to the first electromagnets, except that the first and second signals may be identical signal and flow through the electromagnets based on a preset temporal pattern or at least substantially simultaneously. In all three examples, the counter member may be arranged to emit counter electromagnetic waves capable of canceling at least a substantial (or only a selected) portion of the harmful waves at least partially based upon at least one of the above relation, directions, and/or amplitudes, thereby minimizing the irradiation. In another example, the electromagnets may be similar to the first electromagnets, except that such electromagnets may also be arranged to be disposed at an identical distance or different distances with respect to the user so that the counter member may emit the counter waves defining greater or same magnitudes, respectively, compared with those of the harmful waves.

In another aspect of the present invention, an electromagnetically-countered speaker system may be provided for generating audible sounds based upon dynamic signals supplied thereto while minimizing irradiation of harmful electromagnetic waves to an user thereof. The system may include at least one case member, at least one drive member, at least one dust cap, at least one bracket, at least one suspension, and at least one spider, where the case member may define a front to be disposed closer to the user, a rear to be disposed away from the user, and at least one opening through such a front, where the drive member may couple with the case member and include at least one cone and at least one voice coil, where the voice coil may couple with the cone, receive first dynamic signal, and form therearound first dynamic magnetic fields when the first signal flows therein while emitting such harmful waves, where the cone may form a wider end and a narrower end and may also be capable of vibrating and generating the sounds, where the dust cap may be implemented in the narrower end of the cone and along a longitudinal axis of the cone, where the bracket may be disposed in the case member and retain the driver member therein, where the suspension may be flexible and also movably couple with the wider end of the cone with the bracket, and where the spider may be coupled to the narrower end of the cone and also retain the voice coil thereon.

In one exemplary embodiment of this aspect of this invention, a system may further include at least one counter member which may be arranged to couple with the case and/or drive members in a preset relation, to form second dynamic fields capable of interacting with the first magnetic fields and also generating between the fields at least one of repulsive and attractive forces primarily responsible for vibrating the cone, and to irradiate counter electromagnetic waves capable of canceling at least a substantial (or only a selected) portion of the harmful waves, thereby minimizing the irradiation. Such a counter member may be incorporated into various portions of the system, e.g., to be disposed on an exterior (or an interior) of the case member, bracket, cone, suspension, dust cap, and/or spider, to be embedded in or inside such a case member, bracket, suspension, cone, dust cap, and/or spider, to be disposed between the case member and at least one of the bracket, cone, dust cap, and suspension, to be disposed between the bracket and at least one of the suspension, cone, and spider, to be also disposed between the suspension and at least one of the cone and spider, to be disposed between the cone and the spider and/or dust cap, to be disposed between the dust cap and spider, to be also disposed closer to (or farther from) the front of the case member than the voice coil, to be disposed at an at least a similar distance from the front of the case member as the voice coil, to be also disposed symmetrically (or asymmetrically) about the longitudinal axis of the cone, to be disposed about only a portion of the longitudinal axis of the cone, and the like. For all these dispositions, the counter member may be arranged to directly couple to the case member, drive member, dust cap, bracket, suspension, and/or spider. Alternatively, the system may include at least one coupler, while the counter member may also be arranged to couple with the case member, drive member, dust cap, bracket, suspension, and/or spider through the coupler.

In another exemplary embodiment of this aspect of the present invention, a system may include at least one speaker magnet and at least one counter member. The speaker magnet may be arranged to magnetically couple with the voice coil, to generate static magnetic fields capable of interacting with the first magnetic fields and generating first repulsive and/or attractive forces partially responsible for vibrating the cone between the voice coil and itself. The counter member may be arranged to couple with the case and/or drive members in a preset relation, to generate second dynamic fields capable of interacting with the first magnetic fields and also generating second repulsive and/or attractive forces preferentially responsible for vibrating the cone between the voice coil and itself, to irradiate counter electromagnetic waves capable of canceling at least a substantial (or only a selected) portion of the harmful waves, thereby minimizing the irradiation, and to be incorporated in various portions of such a system, e.g., to be disposed on an exterior (or interior) of the case member, bracket, cone, dust cap, suspension, and/or spider, to be embedded inside at least one of the case member, bracket, dust cap, suspension, cone, and/or spider, to be disposed between the case member and at least one of such a bracket, cone, dust cap, and suspension, to be disposed between the bracket and at least one of the suspension, cone, spider, and speaker magnet, to be disposed between the suspension and at least one of the cone and spider, to be disposed between such a cone and at least one of the spider, dust cap, and speaker magnet, to be disposed between the dust cap and the spider and/or speaker magnet, to be disposed closer to (or farther from) the front of the case member than the voice coil, to be disposed at a substantially similar distance from the front of the case member as the voice coil, to be disposed symmetrically (or asymmetrically) about the longitudinal axis of the cone, to be disposed about only a portion of the longitudinal axis of the cone, and the like. In all of these examples, such a counter member may be arranged to directly couple with the case member, drive member, dust cap, bracket, suspension, spider, and/or magnet. Alternatively, the system may further have at least one coupler, while the counter member may be arranged to couple with the case member, drive member, dust cap, bracket, suspension, spider, and/or speaker magnet through such a coupler.

In another aspect of the present invention, an electromagnetically-countered speaker system may be provided for generating audible sounds based on at least one dynamic signal while minimizing irradiation of harmful electromagnetic waves onto an user by shielding such an user from at least a substantial portion of the harmful waves.

In one exemplary embodiment of this aspect of the present invention, a system may include the first case member, the first drive member, and at least one magnetic shield of the first, second or third type.

In another exemplary embodiment of this aspect of the present invention, a system may include the first case member, the first drive member, at least one electric shield of the first type, and at least one magnetic shield of the first, second or third type.

In another exemplary embodiment of this aspect of the present invention, a system may include at least one In another exemplary embodiment of this aspect of the present invention, a system may include the first case member, the first drive member, and at least one electromagnetic shield. In one example, at least a portion of the electromagnetic shield may be arranged to be electrically conductive, to couple with the case and/or drive members, and to absorb electric waves of the harmful waves therein, and at least another portion of the electromagnetic shield may be arranged to couple with the case and/or drive members, to absorb magnetic waves of the harmful waves therein, and to reroute the magnetic waves away from the user therealong, thereby minimizing the irradiation. In another example, at least a portion of the electromagnetic shield may be arranged to be electrically conductive, to be coupled to the case and/or drive members, and to absorb electric waves of such harmful waves therein, while at least another portion of the electromagnetic shield may be arranged to couple with the case and/or drive members, to include at least one magnetically permeable path member and at least one magnet member defining at least one magnetic pole thereon and indirectly or directly coupling with such a path member, to absorb magnetic waves of the harmful waves along the path member, and to terminate the magnetic waves in the pole of the magnet member, thereby minimizing such irradiation. In yet another example, at least a portion of the electromagnetic shield may be arranged to be electrically conductive, to couple with the case and/or drive members, and to absorb thereinto electric waves of the harmful waves, while at least another portion of the electromagnetic may be arranged to couple with the case and/or drive members and to include a magnetically permeable path member, a magnet member having at least one magnetic pole thereon and directly or indirectly coupling to the path member, and another magnetically permeable shunt member, where the path member may be arranged to absorb magnetic waves of the harmful waves therein, where the magnet member may be arranged to terminate such magnetic waves in the pole while defining therearound static magnetic field, while the shunt member may be arranged to confine the static magnetic fields generated by the magnet member closer thereto, thereby minimizing the irradiation.

In another aspect of the present invention, an electromagnetically-countered earphone system may be provided for generating audible sounds based on at least one dynamic signal while minimizing irradiation of harmful electromagnetic waves to an ear and a brain of the user, where such a system may be an earphone at least a portion of which may be arranged to be disposed into a canal of an ear of the user, a headphone which may be arranged to be disposed around a head and over the ear of the user, a handset of a phone which may be arranged to be disposed over the ear of the user, and a mobile phone which may be arranged to be disposed over the ear of the user.

In one exemplary embodiment of this aspect of the present invention, a system may include at least one case member, at least one drive member, and at least one counter member, where the case member may be arranged to be disposed over (or into) the ear of the user. The drive member may be arranged to be supported by the case member, to include therein a first electromagnet and a mobile cone coupling with the first electromagnet, and to flow a first signal through the first electromagnet in a preset direction in order to generate therearound first dynamic magnetic fields. The counter member may be arranged to be supported by the case and/or drive members, to have a second electromagnet disposed in a preset relation to the first electromagnet, and then to flow a second signal through the second electromagnet in another preset direction in order to generate second dynamic magnetic fields therearound. The first and second magnetic fields may be arranged to exert therebetween repulsive and/or attractive forces based on the relation and directions, where magnitudes of each of the forces may be arranged to be in preset proportion to magnitudes of the first and/or second signals. The drive member may be arranged to generate vibration of the cone based upon such forces, to convert such vibration of the cone into the sounds, and to transmit the sounds onto the user while irradiating such harmful waves. The counter member may be arranged to emit counter electromagnetic waves which may be capable of canceling at least a portion of the harmful waves based upon such a relation and directions, thereby minimizing the irradiation. In one option, the counter member may include at least one insert disposed in another preset relation to the counter member and including therein at least one ferromagnetic material, thereby augmenting the second magnetic fields as the second signal flows in the second electromagnet. In another option, the drive member may include at least one permanent speaker magnet disposed in another preset relation to at least one of the electromagnets and exerting the repulsive and/or attractive forces which may then be supplementary to such forces between the first and second magnetic fields.

In another exemplary embodiment of this aspect of the present invention, a system may include at least one case member, at least one drive member, and at least one counter member, where such a case member may be arranged to be disposed over or into the ear of the user. Such a drive member may be arranged to be supported by the case member, to include a first electromagnet and a mobile cone coupling with the first electromagnet and to flow a first signal with first dynamic characteristics in a preset direction in the first electromagnet in order to generate therearound first dynamic magnetic fields. The counter member may be arranged to be supported by the case and/or drive members, to include a second electromagnet disposed in a preset relation to the first electromagnet and to flow a second signal with second characteristics at least similar to those of the first signal along the second electromagnet in another preset direction in order to generate therearound second dynamic magnetic fields. The first and second magnetic fields may be arranged to exert therebetween repulsive and/or attractive forces based on the relation and characteristics, where magnitudes of each of the forces may be arranged to be in preset proportion to amplitudes of the first and/or second signals. The drive member may be arranged to create vibration of the cone based on the forces, to convert the vibration into the sounds, and then to transmit the sounds onto the user while irradiating such harmful waves. The counter member may be arranged to emit counter electromagnetic waves capable of canceling at least a portion of the harmful waves based on the relation and characteristics, thereby minimizing the irradiation. In one option, such a counter member may include at least one insert disposed in another preset relation to the counter member and having therein at least one ferromagnetic material, thereby augmenting the second magnetic fields as the second signals flow through the second electromagnet. In another option, the drive member may include at least one permanent speaker magnet disposed in another preset relation to at least one of the electromagnets and exerting repulsive and/or attractive forces which may then be supplementary to the forces between the first and second magnetic fields.

Configurational and/or operational variations and/or modifications of the foregoing systems fall within the scope of the present invention.

The system may be any electric devices including at least one mechanism which may convert acoustic sounds into electric and/or optical signals, where examples of such devices may include, but not be limited to, speakers, earphones, headphones, handsets of phones, mobile phones, and the like. The system may be any electric devices including at least one mechanism which may convert electric and/or optical signals into acoustic sounds, where examples of such devices may include, but not be limited to, microphones. The system may be a system having at least two same or different speakers enclosed in a single case member, another system including at least two same or different speakers separately enclosed inside different case members, a system with a pair of earphones, a system with a pair of headphones, an assembly having at least one speaker and at least one microphone, and the like.

Such signals may be electrical signals, optical signals, magnetic signals, and the like. The first and second signals may be same signals sequentially flowing in the electromagnets, may be different portions of the dynamic signal supplied to the electromagnets in a parallel mode, may define identical or different amplitudes, and the like. The above directions may be identical, opposite or transverse. One of the first and second signals may be at least a portion of the dynamic signal, whereas the other of the first and second signals may also be derived from such one of the signals. One of the first and second signals may be at least a portion of the dynamic signal, while the other of the first and second signals may then be externally provided and manipulated to define the characteristics similar to those of such one of the signals, and the like.

The drive member may not include any permanent speaker magnet or may include at least one permanent speaker magnet which may generate only a preset portion of such repulsive or attractive forces required to generate the vibration. Such a preset portion may not exceed three quarters, one half, one third, a quarter, and the like. Such a proportion may also be a first-order proportion without an offset, another first-order proportion defining an offset, a simple higher-order proportion without an offset, another higher-order proportion defining another offset, and the like.

The movable part of the driver member may correspond to the cone. Such a cone may also be in an unstressed state as no signals flow in the electromagnets and move toward a stressed state by the one of the forces as the signals flow in the electromagnets. The cone may be in a stressed state when no signals flow in the electromagnets and move toward an unstressed state by the one of the forces as the signals flow in the electromagnets.

The first electromagnet of the driver member may correspond to the voice coil which may be releasably or fixedly couple around the cone. The second electromagnet may be movably or fixedly coupled to the drive member, counter member, and the like. The counter member or unit may include the second electromagnet which may movably or fixedly couple with the case and/or drive members. The relation may relate to a shapes and/or size of the counter member or unit, a shape and/or size of the voice coil, a shape and/or size of the magnet (if any), an orientation of the counter member or unit and/or voice coil (and/or magnet if any), an arrangement and/or an orientation of the counter member or unit and/or voice coil (and/or magnet if any), amplitudes of at least one of the signals flowing in the counter member or unit and/or voice coil, and/or directions of at least one of the signals flowing in the counter member or unit and/or voice coil, and the like. The first and second electromagnets may have identical, similar or different configurations. The first and second electromagnets may include multiple turns of conductive wires wound in identical, similar or different number of turns in identical, similar or different directions. Such first and second electromagnets and/or magnetic fields generated thereby may be aligned axially or laterally, misaligned axially or laterally, and the like. The counter member or unit may manipulate the counter waves to define amplitudes which may be at least substantially similar to, greater than or less than those of the harmful waves when measured at a preset distance from the user during use.

The counter member or unit also define a curvilinear shape of a wire, an array thereof, a strip, an array thereof, a sheet, an array thereof, a tube, an array thereof, a coil, an array thereof, a mesh, an array thereof, a mixture including at least two of the shapes, a combination of at least two of the shapes, and the like. Such an array may define a shape of a bundle, a braid, a coil, a mesh, and the like. The shape and/or array may define a two-dimensional shape or a three-dimensional shape. At least two portions of the counter member, at least two portions of the counter unit, and/or at least two counter units of the counter member may have the same shape with different sizes, different shapes with similar or different sizes, and the like. The counter member or unit and voice coil may define the same shape with different sizes, different shapes with similar or different sizes, and the like. At least a portion of the coil of the counter member or unit may also be wound into a two- or three-dimensional solenoid and/or toroid, where opposing ends of the solenoid and/or toroid may be arranged to oppose each other. The coil of the counter member or unit may include an even number of wires and/or strips at least two of which may generate the counter waves with at least partially opposite phase angles. At least one electric insulator may be disposed between at least two of the counter members or units disposed adjacent (or close) to each other when the counter members or units may not be coated by an electrically insulative material, may contact each other when at least one of the counter members or units may be coated by the insulative material, and the like. The counter member or unit may form at least substantially uniform shape and/or size along at least its substantial portion along its longitudinal axis, may have shapes and/or sizes varying along the direction, and so on.

At least two of the counter members or units may electrically couple to each other in a series pattern, in a parallel pattern or in a hybrid pattern. At least two of the counter members or units may also define longitudinal axes and may not electrically couple with each other along at least substantial portions along the axes. At least one of the counter members or units may enclose at least a portion of another of the counter units therein in a concentric arrangement, may be extended or braided along with the portion of such another counter member or unit in a paired arrangement, and the like. Such a counter member or unit may form at least one junction and/or bifurcation. The counter member or unit may include therealong multiple layers at least two of which may also operate as at least two of such counter members or units. The counter member or unit may have multiple portions which may couple with each other in series and/or parallel patterns, which may not couple with each other, and so on. The system may have multiple counter members or units which may couple with each other in series and/or parallel patterns or which may not couple with each other. At least two portions of the counter member, at least two portions of the counter unit, and/or at least two counter units of such a counter member may extend in the same direction while forming a series coupling, where the signals flowing therethrough may have the same amplitude. At least two portions of the counter member, at least two portions of the counter unit, and/or at least two counter units of the counter member may extend along the same direction while forming a parallel coupling, where the signals flowing therethrough may have the same amplitude or different amplitudes. The signals may flow through at least two portions of the counter unit, at least two counter units of the counter member, and/or at least two portions of such a counter member along the same direction, while such at least two of the portions and/or units may be wound along opposite directions, thereby canceling at least portions of the counter waves irradiated thereby. The signals may flow in at least two portions of the counter unit, at least two counter units of the counter member, and/or at least two portions of the counter member in opposite directions, but such at least two of the portions or units may be wound along the same direction, thereby canceling at least portions of the counter waves which may be irradiated thereby. The counter member or unit and driver member may define substantially identical, similar or different resonance frequencies. The counter member or unit and voice coil (or magnet, if any) may also define identical, similar or different resonance frequencies.

At least two portions of the counter member, at least two portions of the counter unit, and/or at least two counter units of the counter member may define resonance frequencies different from those of the rest thereof. In addition, at least one of multiple portions of the counter member, at least one of multiple portions of the counter unit, and/or at least one of multiple counter units of the counter member may similarly define a resonance frequency different from those of the rest thereof. At least one of multiple portions of such a counter member, at least one of multiple portions of the counter unit, and/or at least one of multiple counter units of the counter member may also be made of and/or include at least one different material, define a different resonance frequency, and have a different spectrum from the rest of the portions of the counter unit and from the rest of such counter units of the counter member, respectively. In addition, at least two portions of the counter member, at least two portions of the counter unit, and/or at least two counter units of the counter member may be made of and/or include at least one common material and one of such at least two portions or units may also include at least one frequency-modulating agent and have the spectrum which may then overlap only preset portions of the spectrum of another of the two of the portions or units but may not overlap the rest of the spectrum thereof. The preset portions of the electromagnetic waves may include low-frequency waves having frequencies less than 300 kHz, very low-frequency waves having frequencies less than 30 kHz, ultra low-frequency waves with frequencies less than 3 kHz, extremely low-frequency waves having frequencies less than 300 Hz, and carrier frequencies in a range of from about 50 Hz to about 60 Hz. At least one portion of the counter member, at least one portion of the counter unit, and/or at least one counter unit of such a counter member may be made of and/or include at least one material for emitting infrared rays including far-infrared rays, medium-infrared rays, and near-infrared rays as the signal flows therein. The rest of the electromagnetic waves may be far infrared rays in a frequency range from about 300 gHz to about 10 tHz, medium infrared rays in a frequency range from about 10 tHz to about 100 tHz, a near infrared rays in a frequency range from about 100 tHz to about 700 tHz, and the like.

The system may include at least one of the magnetic shields described hereinabove or in the co-pending Applications. The magnetic shields may be disposed in, on, over, around, and/or through at least one of the members. The magnetic shields may define shapes at least partially conforming to shapes of at least one of the members or, alternatively, may define shapes at least partially different from shapes of at least one of the members. Such a path member may preferably define a relative magnetic permeability greater than 1,000 or 10,000. The pole of the magnet member may be the South Pole. The shunt member may directly or indirectly contact the magnet member. Such a shunt member may also have a relative magnetic permeability greater than 1,000, 10,000 or 100,000. The magnetic shields described hereinabove or disclosed in the co-pending Applications may be incorporated into any of the prior art devices and define novel systems of this invention. Such a system may include at least one of the electric shields described hereinabove or in the co-pending Applications. The electric shields described hereinabove or disclosed in the co-pending Applications may be incorporated into any of the prior art devices and define novel systems of this invention. The magnetic and/or electric shields may form shapes and/or sizes which may be maintained uniform along a longitudinal axis of at least one of the members or which may change therealong. The shapes and/or sizes of the magnetic and/or electric shields may also be identical to, similar to or different from those of at least one of the members. The system may include multiple magnetic shields and/or electric shields. At least two of the magnetic and/or electric shields may shield against the magnetic waves and/or electric waves of the harmful waves defining same or different frequencies in same or different extents. The magnetic and/or electric shields may be disposed over at least a portion (or entire portion) of at least one of the members. The system may include the counter member as well as at least one of the electric shields and magnetic shields or, alternatively, may include at least one of such electric shields and magnetic shields but no counter member. At least one of the members may operate on AC or DC. The system may include at least one control member capable of controlling at least one of the members thereof. The control member may perform power operations for varying configurational characteristics of the dynamic signal, e.g., by squaring amplitudes thereof or square-rooting the amplitudes thereof. Such a control member may perform the power operations in a digital or analog mode.

In another aspect of the present invention, a method may be provided for generating audible sounds based upon dynamic signals using a speaker system while minimizing irradiation of harmful electromagnetic waves irradiated from at least one driver member by canceling at least a substantial (or only preset) portion of the harmful waves by at least one counter member.

In one exemplary embodiment of this aspect of the invention, a method may have the steps of: incorporating such a counter member in a preset relation to the drive member (to be referred to as the "first incorporating"); flowing a first signal in the drive member (to be referred to as the "first flowing"); generating the sounds by the drive member as a result of such flowing while irradiating such harmful waves thereby (to be referred to as the "first generating"); flowing a second signal in such a counter member (to be referred to as the "second flowing"); emitting counter electromagnetic waves of preset phase angles by the counter member (to be referred to as the "first emitting"); and manipulating such a relation between the members for canceling the portion of the harmful waves by the counter waves, thereby minimizing the irradiation.

In another exemplary embodiment of this aspect of the invention, such a method may have the steps of: incorporating such drive and counter members at preset distances from an user (which is to be referred to as the "second incorporating"); flowing a first signal having a first amplitude along a first direction in the drive member (to be referred to as the "third flowing"); the first generating; flowing a second signal of a second amplitude in a second direction in the counter member (to be referred to as the "fourth flowing"); the first emitting; and manipulating the amplitudes and directions to cancel the portion of the harmful waves with the counter waves, thereby minimizing the irradiation.

In another exemplary embodiment of this aspect of the invention, such a method may have the steps of: the second incorporating; the first flowing; the first generating; the second flowing; the first emitting; and manipulating the distances to cancel the portion of such harmful waves with the counter waves in proximity to the user, thereby minimizing the irradiation.

In another exemplary embodiment of this aspect of the invention, such a method may have the steps of: the first incorporating; implementing inside or through the second electromagnet at least one insert which may be at least one of magnetically hard and magnetically soft; the third flowing; the first generating; the fourth generating; the first emitting; augmenting the counter waves by the insert up to an amount determined by a shape of the insert, a size thereof, and/or a disposition thereof; and then manipulating the relation, amplitudes, directions, size, shape, and/or disposition to cancel the portion of the harmful waves by the counter waves, thereby minimizing the irradiation.

In another aspect of the present invention, a method may be provided for generating audible sounds based upon at least one dynamic signal by a speaker system while minimizing irradiation of harmful electromagnetic waves irradiated from at least one derive member of a first configuration by canceling at least a substantial (or only preset) portion of the harmful waves by at least one counter member.

In one exemplary embodiment of this aspect of the invention, a method may have the steps of: the first incorporating; the first flowing; the first generating; the second flowing; the first emitting; and manipulating a configuration of the counter member relative to the first configuration for canceling the portion of the harmful waves with the counter waves, thereby minimizing the above irradiation. Such manipulating may be replaced by one of the steps of: forming such a counter member at least similar to the first configuration to cancel the portion of such harmful waves by the counter waves, thereby minimizing the irradiation; forming the counter member to be different from the first configuration but in another configuration capable of canceling the portion of the harmful waves with the counter waves, thereby minimizing such irradiation; forming the counter member to be at least partially symmetric for canceling the portion of the harmful waves by the counter waves, thereby minimizing the irradiation; forming the counter member asymmetrically but in a configuration capable of canceling the portion of the harmful waves by the counter waves, thereby minimizing the irradiation; conforming the counter member to at least a portion of the first configuration to cancel the portion of the harmful waves by the counter waves, thereby minimizing the irradiation; conforming the counter member not to such a first configuration but into another configuration capable of canceling the portion of the harmful waves by the counter waves, thereby minimizing the irradiation; forming the counter and driver members in at least similar compositions to cancel the portion of the harmful waves by the counter waves, thereby minimizing the irradiation; and incorporating into the counter member at least one material which is not present in the driver member for canceling the selected portion of the harmful waves with the counter waves, thereby minimizing the irradiation.

In another exemplary embodiment of this aspect of the invention, such a method may include the steps of: incorporating the counter member in a preset disposition to the drive member; the first flowing; the first generating; the second flowing; the first emitting; and enclosing at least a portion of the drive member with the counter member, thereby canceling the portion of the harmful waves by the counter waves and minimizing the irradiation. The enclosing may be replaced by one of the steps of: disposing the counter member side by side to at least a portion of the drive member, thereby canceling the portion of the harmful waves by the counter waves and minimizing the irradiation; aligning such a counter member with at least a portion of the drive member to cancel the portion of the harmful waves by the counter waves, thereby minimizing the irradiation; misaligning such a counter member from the drive member but rather in a disposition for canceling the portion of the harmful waves by the counter waves, thereby minimizing the irradiation; disposing the counter member closer to (or farther from) an user than the drive member to cancel the portion of the harmful waves by the counter waves, thereby minimizing the irradiation; disposing the counter and drive members in at least similar distances from an user for canceling the portion of the harmful waves by such counter waves, thereby minimizing such irradiation; disposing the counter member to be at least partially symmetric to at least a portion of such a drive member to cancel the portion of the harmful waves by the counter waves, thereby minimizing the irradiation; and disposing the counter member asymmetrically to the drive member but rather in an arrangement to cancel the portion of the harmful waves by the counter waves, thereby minimizing the irradiation.

In another exemplary embodiment of this aspect of the invention, such a method may have the steps of: the first incorporating; the third flowing; the first generating; the fourth generating; the first emitting; and manipulating the amplitudes and directions of the signals in order to cancel the portion of the harmful waves by the counter waves, thereby minimizing the irradiation. The manipulating may be replaced by one of the steps of: manipulating the directions of the signals based on the relation so as to cancel the portion of the harmful waves by such counter waves, thereby minimizing the irradiation; manipulating the amplitudes of the signals based on a distance between an user and the drive member and another distance between the user and counter members for canceling the portion of the harmful waves by the counter waves, thereby minimizing the irradiation; electrically coupling the counter and drive members in a parallel mode, a series mode or a hybrid modes to cancel the portion of the harmful waves with the counter waves, thereby minimizing the irradiation; electrically coupling such a counter member with the drive member and supplying at least similar signals to the drive (or counter) member and thereafter to the counter (or drive) member to cancel the portion of such harmful waves with the counter waves, thereby minimizing the irradiation; and electrically coupling the counter member with the drive member and then supplying at least similar signals to the drive and counter members at least substantially simultaneously for canceling the portion of the harmful waves with the counter waves, thereby minimizing the irradiation.

In another exemplary embodiment of this aspect of the invention, such a method may have the steps of: defining a single drive member and a single counter member; the first incorporating; the first flowing; the first generating; the second flowing; the first emitting; and then manipulating the counter member to emit the counter waves capable of canceling the portion of such harmful waves, thereby minimizing the irradiation.

In another exemplary embodiment of this aspect of the invention, such a method may have the steps of: defining multiple sources emitting the harmful waves in the drive member; incorporating the counter member in a preset relation to one of such sources; the first flowing; the first generating; the second flowing; the first emitting; and manipulating the counter member to irradiate the counter waves capable of canceling the portion of the harmful waves irradiated by at least one of but not all of such sources, thereby minimizing the irradiation.

In another exemplary embodiment of this aspect of the invention, such a method may have the steps of: defining multiple sources emitting the harmful waves in the drive member; incorporating such a counter member in a preset relation to such sources; flowing first signals in such sources; the first generating; the second flowing; the first emitting; and manipulating the counter member to irradiate the counter waves capable of canceling the portion of such harmful waves irradiated by at least one but not all of the sources, thereby minimizing the irradiation. The defining may be replaced by the step of: defining multiple the drive member each of which is a source of the harmful waves.

In another exemplary embodiment of this aspect of the invention, such a method may have the steps of: defining multiple sources of such harmful waves in the drive member; incorporating multiple the counter members in a preset relation to the sources; flowing first signals in the sources; the first generating; flowing second signals in the counter members; emitting counter electromagnetic waves defining preset phase angles by at least two of the counter members; and manipulating at least two of the counter members to irradiate the counter waves capable of canceling the portion of such harmful waves emitted by all of the sources, thereby minimizing the irradiation. The defining may be replaced by the step of: defining multiple the drive member each of which is a source of the harmful waves.

In another aspect of the present invention, a method may be provided for generating audible sounds based upon at least one dynamic signal through vibrating a cone which couples with at least one first electromagnet of an electromagnetically-countered speaker system while irradiating harmful electromagnetic waves to an user of the system but capable of minimizing the irradiating the harmful waves with at least one second electromagnet of the system.

In one exemplary embodiment of this aspect of the invention, a method may have the steps of: disposing the second electromagnet in a preset relation to the first electromagnet (to be referred to as the "first disposing"); providing the signals through the electromagnets while providing repelling and/or attracting forces therebetween (which will be referred to as the "first providing"); vibrating the first electromagnet as well as the cone coupled thereto by the forces, thereby generating the sound while irradiating such harmful waves from the first electromagnet (to be referred to as the "first vibrating"); and then manipulating the relation of the second electromagnet while emitting counter electromagnetic waves by the second electromagnet until such counter waves cancel at least a substantial (or only a selected) portion of the harmful waves, thereby minimizing the irradiating the harmful waves.

In another exemplary embodiment of this aspect of the invention, such a method may have the steps of: aligning the second electromagnet with the first electromagnet; providing the signals having preset amplitudes along such electromagnets along preset directions while providing repelling and/or attracting forces therebetween (to be referred to as the "second providing"); the first vibrating; and manipulating amplitudes of the signals supplied to the second electromagnet and a distance from the second electromagnet to the first electromagnet while irradiating counter electromagnetic waves by the second electromagnet until such counter waves cancel at least a substantial (or only a selected) portion of the harmful waves, thereby minimizing the irradiating the harmful waves.

In another exemplary embodiment of this aspect of the invention, such a method may have the steps of: the first disposing; implementing inside (or through) the second electromagnet at least one insert which may be magnetically hard or magnetically soft; the first providing; the first vibrating; and manipulating the relation and an amplitude and/or a direction of the signal in the second electromagnet while irradiating counter electromagnetic waves by the second electromagnet and augmenting such counter waves by the insert, thereby canceling at least a substantial (or only a selected) portion of the harmful waves by the counter waves as well as minimizing the irradiating the harmful waves.

In another exemplary embodiment of this aspect of the present invention, such a method may have the steps of: the first disposing; the second providing; irradiating the harmful waves by the first electromagnet during the flowing (which will be referred to as the "first irradiating"); emitting counter electromagnetic waves from the second electromagnet during the flowing (to be referred to as the "second emitting"); the first vibrating; and manipulating such a relation, amplitudes, and/or directions for attaining maximum magnitudes of the forces and for matching magnitudes of the harmful waves with magnitudes of the counter waves, thereby canceling at least a substantial (or only a selected) portion of the harmful waves with the counter waves while minimizing the irradiating the harmful waves.

In another exemplary embodiment of this aspect of the invention, such a method may have the steps of: the first disposing; the second providing; the first irradiating; the second emitting; the first vibrating; manipulating at least one of the relation, amplitudes, and directions in order to attain maximum magnitudes of the forces and in order to match magnitudes of the harmful waves with magnitudes of such counter waves to a preset extent, thereby canceling at least a substantial (or only a selected) portion of the harmful waves with the counter waves (to be referred to as the "first manipulating"); and including at least one electrically conductive shield around at least one of the electromagnets to absorb at least a portion of electric waves of such harmful waves thereinto, thereby minimizing the irradiating the harmful waves (to be referred to as the "first electric shielding").

In another exemplary embodiment of this aspect of the invention, such a method may have the steps of: the first disposing; the second providing; the first irradiating; the second emitting; the first vibrating; the first manipulating; and including at least one magnetically permeable shield around at least one of the electromagnets to absorb at least a portion of magnetic waves of the harmful waves therein, thereby minimizing the irradiating the harmful waves (to be referred to as the "first magnetic shielding").

In another exemplary embodiment of this aspect of the present invention, such a method may have the steps of: the first disposing; the second providing; the first irradiating; the second emitting; the first vibrating; the first manipulating; the first electric shielding; and the first magnetic shielding.

In another aspect of the present invention, a method may be provided for generating audible sounds based upon dynamic signals by a speaker system fabricated into an earphone, a headphone, a handset of a telephone, and/or a mobile phone while minimizing irradiation of harmful electromagnetic waves by at least one drive member of the system to a brain of an user through canceling at least a substantial (only selected) portion of the harmful waves with at least one counter member.

In one exemplary embodiment of this aspect of the invention, a method may have the steps of: the first incorporating; the third flowing; the first generating; the fourth generating; the first emitting; and manipulating the relation of the counter member so as to cancel the portion of the harmful waves, thereby minimizing the irradiation.

In another exemplary embodiment of this aspect of the invention, such a method may have the steps of: the first incorporating; the third flowing; the first generating; the fourth generating; the first emitting; and manipulating at least one of the amplitudes and directions so as to cancel the portion of the harmful waves, thereby minimizing the irradiation.

In another exemplary embodiment of this aspect of the invention, such a method may have the steps of: the first incorporating; the third flowing; the first generating; the fourth generating; the first emitting; and manipulating dispositions of the members for canceling the portion of the harmful waves in a proximity to the user, thereby minimizing the irradiation.

In another aspect of the present invention, a method may be provided for generating audible sounds based upon dynamic signals by a speaker system including multiple speakers each including at least one drive member while minimizing irradiation of harmful electromagnetic waves from the drive members to a brain of an user of the system by canceling at least a substantial (only selected) portion of the harmful waves by at least one counter member.

In one exemplary embodiment of this aspect of the invention, a method may have the steps of: disposing the speakers in a single case member; defining at least one source of the harmful waves in each of the speakers; incorporating multiple counter members in preset relations to each of the wave sources; flowing first signals through the sources; generating the sounds while irradiating the harmful waves by the sources; flowing second signals defining preset amplitudes along each of the counter members in preset directions; and then manipulating such relations, amplitudes, and/or directions for irradiating by each of the counter members counter electromagnetic waves capable of canceling at least a portion of the harmful waves emitted by each of the sources, thereby minimizing the irradiation from each of the speakers.

In another exemplary embodiment of this aspect of the invention, such a method may have the steps of: disposing the speakers in a single case member; defining at least one source of the harmful waves in each of the speakers; incorporating at least one counter member in a preset relation to the sources; flowing first signals through the sources; generating the sounds while irradiating the harmful waves by the sources; flowing second signals of preset amplitudes in the counter member in a preset direction; and then manipulating such a relation, amplitudes, and/or direction for emitting by the counter member counter electromagnetic waves which are capable of canceling at least a portion of a sum of the harmful waves emitted by all of the sources, thereby minimizing the irradiation as well.

Configurational and/or operational variations and/or modifications of the foregoing methods fall within the scope of the present invention.

The above emitting may at least include one of the steps of: manipulating the phase angles of the counter waves to be at least similar to those of the harmful waves when the counter and harmful waves propagate in at least partially opposite directions; manipulating the phase angles of the counter waves to be at least opposite to those of the harmful waves when such counter and harmful waves propagate along at least similar directions; and manipulating the phase angles of the counter waves to be transverse to those of the harmful waves when the counter and harmful waves propagate along directions transverse to each other.

The incorporating may include at least one of the steps of: enclosing at least a portion of the drive member by the counter member; disposing the counter member symmetrically to the portion of the drive member (or source); disposing the counter member closer to or farther from the user than the drive member (or source); aligning the counter member with the drive member or source; and disposing the counter member along a line between the user and drive member or source during use. The incorporating may include at least one of the steps of: disposing at least a portion of such a drive member (or source) laterally or side by side with the counter member; disposing the counter member asymmetrically to such a portion of the drive member (or source); disposing such counter and drive members at similar distances to the user; misaligning the counter member from the source (or drive member); disposing the counter member off a line connecting the user and drive member (or source) during use; and the like. The incorporating may also include one of the steps of: directly coupling the counter member with a portion of the system; and coupling the counter member to the system through a coupler. The above incorporating may include the step of: manipulating at least one of configuration of at least a portion of the counter member, orientation thereof with respect to at least a portion of the source, arrangement thereof with respect thereto, and so on. The incorporating may include the step of: manipulating the configuration, orientation, and/or arrangement with respect to amplitudes of such signals flowing in the source, directions of the signals flowing therein, distances between the source or counter member and user, amplitudes of at least one of the counter and harmful waves measured by the user, and the like. The incorporating may also include one of the steps of: enclosing at least a portion of the source by the counter member; enclosing such a portion of the source by the counter member; and disposing the counter member without enclosing any of the source. Such incorporating may also include the steps of: defining multiple counter units in the counter member; and incorporating each of the counter units in the same relation or different relations to the source. The incorporating may include one of the steps of: electrically connecting the source to the counter member in a series mode, parallel mode or hybrid mode; and not directly connecting the source with the counter member electrically.

Such flowing the signals may include one of the steps of: flowing the signals along an entire portion of the source; flowing the signals in only a portion of the source; flowing different portions of the signals in different portions of the source; and the like. The flowing the signals may include one of the steps of: flowing the signals along a single direction along the source; flowing the signals along different directions in different portions of the source, and the like. Such a system may have multiple sources of the harmful waves and the flowing may include one of the steps of: flowing the signals of the same amplitudes along a same direction in all of the sources; flowing the signals defining the same amplitudes in different directions along the sources; flowing such signals of different amplitudes in the same direction in all of the sources; flowing the signals of different amplitudes in different directions in the sources, and the like. The flowings may include one of the steps of: flowing the signals with the same (or different) amplitudes in the counter member; flowing in the counter member another signal which may not be derived from the dynamic signal but may define a temporal pattern at least partially similar to that of the dynamic signal; flowing along the counter member another signal which may not be derived from the dynamic signal but may have a temporal pattern different from that of the dynamic signal. The flowing the currents and/or signals may include one of the steps of: flowing the signals in the source and then in the counter member; flowing the signals in the counter member and then in the source; and flowing the signals at least simultaneously in the source and counter member.

The including the shield may include at least one of the steps of: including the shield in at least a portion of the source; including the shield between at least two portions of the source; disposing the shield over (or on) the source; disposing the shield around at least a portion of the source; disposing the shield between the source and user while defining at least one opening in the shield, and the like. The including the shield may include one of the steps of: orienting the shield in a direction normal to a direction of propagation of the harmful waves; orienting the shield at a preset angle with respect to the harmful waves. The aligning may include at least one of the steps of: aligning a longitudinal axis of the source with that of the counter member; disposing different portions of the counter member along the axis of the source; concentrically disposing such a counter member about the axis of the source; misaligning the counter member from the axis of the source, and the like.

The irradiating and/or emitting the counter electromagnetic waves may also include the step of: manipulating phase angles of such counter waves to be at least partially (or substantially) opposite to those of the harmful waves. Such irradiating and/or emitting the counter electromagnetic waves may include at least one of the steps of: manipulating the amplitudes of such counter waves to be greater (or less) than those of the harmful waves when measured at the source; manipulating the amplitudes of the counter waves to be greater (or less) than those of the harmful waves when measured at the brain (or ear) of the user; manipulating the amplitudes of the counter waves to be at least substantially similar to those of such harmful waves when measured at one of the source, ear, and brain, and the like. The irradiating and/or emitting the counter electromagnetic waves may include at least one of the steps of: propagating the counter waves in a direction similar or identical to that of the harmful waves; propagating the counter waves in a direction different from that of the harmful waves emitted by each of multiple sources but in the same direction as that of a sum of the harmful waves from the sources, and the like.

The incorporating may include the step of: forming the counter member in at least one of such a configuration and shape, where such forming may include at least one of the steps of: extending a single wire for at least a portion of the counter member; extending an array or bundle of multiple wires for the portion of the counter member; extending a single strip therefor; extending an array or a bundle of multiple strips therefor; extending a single sheet therefor; extending an array or a bundle of multiple sheets therefor; extending a single tube therefor; extending a bundle and/or an array of multiple tubes therefor; winding a single coil therefor; winding a bundle or array of multiple coils therefor; extending a single annular mesh therefor; and extending an array or bundle of multiple annular meshes therefor. The incorporating may include the steps: forming at least two (or all) of the counter units in one of the steps of the forming. The incorporating the counter units may include the steps: providing at least one of the units based on one of the steps of the forming; and providing at least another of the units based on another of the steps of the forming. Such forming may further include at least one of the steps of: enclosing at least a portion of the source with an array and/or bundle of multiple wires of the counter member; enclosing the portion of the source by an array and/or bundle of multiple strips of the counter member; enclosing such a portion by an array and/or bundle of multiple sheets of the counter member; enclosing the portion of the source by an array and/or bundle of multiple tubes of the counter member; winding with at least one coil of the counter member about the portion of the source; winding such a portion of the source by an array and/or bundle of multiple coils; and enclosing such a portion of the source by at least one annular mesh of the counter member, and the like. The enclosing may include one of the steps of: disposing the counter member indirectly over (or around) the portion of source; and disposing the counter member directly on (or around) the portion of the source. Such enclosing may include at least one of the steps of: arranging at least two of the counter member concentrically; electrically coupling the units in one of a series mode, a parallel mode, and a hybrid mode, and the like. The manipulating such a relation may include the step of: manipulating such configurations, amplitudes, directions, shape, and/or the above arranging.

In another aspect of the present invention, an electromagnetically-countered speaker system may include at least one drive member and at least one counter member and may also be provided for generating audible sounds based on at least one dynamic signal which is supplied to at least one first electromagnet of the drive member and to at least one second electromagnet of the counter member while minimizing irradiation of harmful electromagnetic waves irradiated by such a first electromagnet toward an user by canceling at least a substantial portion (or only selected portion) of such harmful waves by counter electromagnetic waves irradiated by the second electromagnet.

In one exemplary embodiment of this aspect of the invention, such a system may be made by a process including the steps of: providing the drive member with a movable part coupling with the first electromagnet; arranging the first electromagnet to flow a first signal in a first direction therethrough; arranging the second electromagnet to flow a second signal in a second direction therein; disposing the second electromagnet away from the first electromagnet and in a preset relation thereto; flowing the signals along the electromagnets, thereby generating interacting magnetic fields around the first and second electromagnets and also exerting repulsive and/or attractive forces between the first and second electromagnets while irradiating such harmful waves with the first electromagnet; moving the movable part by such forces, thereby generating the sounds; arranging the second electromagnet to irradiate counter electromagnetic waves when the second signal flows therein; controlling amplitudes and the directions of the signals to manipulate the counter waves to define preset configurational and phase characteristics; controlling the relation between the first and second electromagnets in order to manipulate the characteristics of the counter waves to at least partially oppose those of such harmful waves; and propagating such counter waves against the harmful waves, thereby attaining the above canceling and minimizing.

In another exemplary embodiment of this aspect of the invention, a system may be made by a process including the steps of: providing the drive member with a movable part coupling with the first electromagnet; providing the drive member with at least one permanent speaker magnet; arranging the first electromagnet to flow a first signal in a first direction therein; arranging the second electromagnet to flow a second signal in a second direction therein; disposing the second electromagnet away from the first electromagnet and speaker magnet and also in a preset relation thereto; flowing the signals through the electromagnets, thereby generating interacting magnetic fields around the electromagnets and exerting repulsive and/or attractive forces between such electromagnets while irradiating such harmful waves by the first electromagnet; altering such magnet fields and forces by static magnetic fields of the speaker magnet; moving the movable part by the forces, thereby generating the sounds; arranging the second electromagnet to irradiate counter electromagnetic waves when the second signal flows therein; controlling amplitudes and the directions of the signals to manipulate the counter waves to define preset configurational and phase characteristics; controlling the relation between the electromagnets to manipulate such characteristics of the counter waves to at least partially oppose those of the harmful waves; and propagating the counter waves against the harmful waves, thereby attaining the canceling and minimizing.

In another exemplary embodiment of this aspect of the invention, a system may be made by a process including the steps of: providing the drive member with a movable part coupling with the first electromagnet; arranging the first electromagnet to flow a first signal in a first direction therethrough; arranging the second electromagnet to flow a second signal in a second direction therein; disposing the second electromagnet away from the first electromagnet and in a preset relation thereto; flowing the signals along the electromagnets, thereby generating interacting magnetic fields around the first and second electromagnets and exerting at least one of repulsive and attractive forces between the electromagnets while irradiating such harmful waves by the first electromagnet; moving the movable part by the forces, thereby generating the sounds; inserting at least one insert through such a second electromagnet to augment such magnetic fields and forces generated by the second electromagnet; arranging the second electromagnet to irradiate counter electromagnetic waves augmented by such an insert as well when the second signal flows therein; controlling amplitudes and the directions of the signals in order to manipulate such counter waves to define preset configurational and/or phase characteristics; controlling the relation between the electromagnets to manipulate the characteristics of the counter waves to at least partially oppose those of the harmful waves; and propagating such counter waves against the harmful waves, thereby attaining the canceling and minimizing.

In another aspect of the present invention, an electromagnetically-countered speaker system may be provided for generating audible sounds based upon at least one dynamic signal by vibrating a cone coupling to at least one first electromagnet while irradiating harmful electromagnetic waves to an user but capable of reducing or minimizing the irradiating the harmful waves by at least one second electromagnet.

In one exemplary embodiment of this aspect of the invention, such a system may be made by a process including the steps of: disposing such a second electromagnet in a preset relation to the first electromagnet; arranging the electromagnets to flow the signals therealong while generating repulsive and/or attractive forces therebetween; vibrating the cone by the above forces, thereby generating the sounds while emitting the harmful waves by the first electromagnet; emitting counter electromagnetic waves by the second electromagnet in the vibrating; and then manipulating the relation of the second electromagnet and configurational and/or phase characteristics of the counter waves for canceling at least a substantial portion (or only a selected portion) of the harmful waves by such counter waves, thereby attaining the minimizing.

In another exemplary embodiment of this aspect of the invention, a system may be made by a process including the steps of: aligning the first and second electromagnets; arranging such first and second electromagnets to flow the signals therein while generating repulsive and/or attractive forces therebetween; vibrating the cone by the forces, thereby generating the sounds while irradiating such harmful waves by the first electromagnet; irradiating counter electromagnetic waves by the second electromagnet in the vibrating; and then manipulating amplitudes and/or directions of the signals in the electromagnets for canceling at least a substantial portion (or only a selected portion) of the harmful waves by the counter waves, thereby attaining the minimizing.

In another exemplary embodiment of this aspect of the invention, a system may be made by a process including the steps of: disposing such a second electromagnet in a preset relation to the first electromagnet; inserting along the second electromagnet at least one insert which includes therein at least one material which is magnetically soft or hard; arranging the electromagnets to flow the signals therealong while generating at least one of repulsive and attractive forces therebetween; vibrating the cone by the forces, thereby generating the audible sounds while irradiating the harmful waves by the first electromagnet; irradiating counter electromagnetic waves by the second electromagnet during the vibrating while augmenting the counter waves by the insert; and then manipulating the relation of such a second electromagnet and configurational and/or phase characteristics of such counter waves for canceling at least a substantial (or only selected) portion of the harmful waves by the counter waves, thereby attaining the minimizing.

In another exemplary embodiment of this aspect of the invention, a system may be made by a process including the steps of: disposing such a second electromagnet in a preset relation to the first electromagnet; arranging the electromagnets to flow the signals therealong while generating repulsive and/or attractive forces therebetween; vibrating the cone by the forces, thereby providing the sounds while emitting the harmful waves by the first electromagnet; emitting counter electromagnetic waves by the second electromagnet in the above vibrating; and then manipulating the relation of the second electromagnet as well as configurational and phase characteristics of the counter waves in order to match magnitudes of the harmful waves with those of the harmful waves, thereby canceling at least a substantial portion (or only a selected portion) of the harmful waves with the counter waves while minimizing the irradiating the harmful waves.

More product-by-process claims may be constructed by modifying the foregoing preambles of the apparatus and/or method claims and by appending thereonto such bodies of the apparatus and/or method claims. In addition, such process claims may include one or more of the above features of the apparatus and/or method claims of the present invention.

As used herein, the term "magnet" refers to a material or an article which may spontaneously or actively generate magnetic fields therearound by itself, where a strength of the magnetic fields may be measured by a conventional gaussmeter. Accordingly, a permanent magnet defining any arbitrary shape, size, and/or number of the N and S poles may qualify as the "magnet" within the scope of this invention as far as the permanent magnet may generate the measurable magnetic fields therearound. It is to be understood that the "magnet" may not refer to electromagnets unless otherwise specified.

Similarly, the term "magnetic" refers to a property of a material or article which may be able to spontaneously or actively generate magnetic fields therearound. Therefore, a "magnetic material" or "magnetic article" refers to a permanent magnet or an article with the permanent magnet. In contrary, a "nonmagnetic" refers to a property of a material or article which may not spontaneously or actively generate such magnetic fields. Thus, a "paramagnetic," "diamagnetic," and "ferrimagnetic" material or article generally belongs to such a "nonmagnetic" material. It is to be understood that a ferromagnetic material or article may be or may not be "magnetic" depending upon its magnetic state and that such a "nonmagnetic" ferromagnetic material or article may be converted to be "magnetic" by properly aligning its magnetic domains. It is also to be understood that the term "magnetic" refers to the above meaning when related to an article. In contrary, the term "magnetic" may connote different meaning when used in conjunction with verbs, more particularly, the verb "couple" as follows.

The term "magnetic permeability" refers to a property of a substance of retaining magnetic field lines therein and, accordingly, has a dimension of Telsa meter/ampere or Newton/ampere$^2$. The terms "relative magnetic permeability" and "relative permeability" refer to a ratio of the "magnetic permeability" of a substance of interest to that of air and, therefore, are dimensionless properties. As used herein, the term "permeability" means the dimensionless "relative permeability" unless otherwise specified as the "magnetic permeability" with the above dimension. The term "very or highly permeable" means that the "permeability" is high such as, e.g., at least a few orders of magnitudes higher than that of the air. Ferromagnetic materials may be generally relatively permeable, where their examples may include, but not be limited to, elements such as iron, cobalt, nickel, and gadolinium, and certain alloys including or based upon one or more of such elements. Non-ferromagnetic and paramagnetic materials exhibit the "magnetic permeability" slightly greater than that of air, while non-ferromagnetic, diamagnetic materials have the "magnetic permeability" slightly less than that of air. Accordingly, the "permeabilities" of the ferromagnetic materials are very greater than 1.0, while the "permeabilities" of the paramagnetic and diamagnetic materials are respectively slightly greater than and slightly less than 1.0.

The terms "magnetic fields" and "magnetic waves" within the scope of this invention refer to those which are associated with various electromagnetic waves. Therefore, such "magnetic fields" are accompanied by matching electric fields, while such "magnetic waves" are also accompanied by matching electric waves. Only exceptions are the static magnetic fields which are not accompanied by the electric fields, where examples of such static magnetic fields are those generated by the Earth, permanent magnet of the magnet member, and the like. It is appreciated for simplicity of illustration that the "magnetic waves" or "MWs" may collectively include the "magnetic fields" or "MFs" therein and that the "electric waves" or "EWs" may collectively include the "electric fields" or "EFs" therein within the scope of the present invention.

Within the scope of the present invention, the term "wire" collectively refers to a wire, filament, fiber, rod, strand, and/or any other similar elongated shapes of articles each of which may be straight and/or curved (i.e., curvilinear), and each of which may also be arranged in a loop, a coil, a roll, and the like. The term "strip" collectively refers to a strip, bar, pad, tape, and any other planar articles with large aspect ratios (i.e., ratios of lengths to widths or heights) each of which may be straight and/or curved, each of which may be arranged in a two- or three-dimensional configuration, each of which may also be arranged in a loop, a coil, a roll, and so on. In addition, the term "sheet" collectively refers to a sheet, a slab, a foil, a film, a plate, a layer, and any other planar articles which may be relatively wider than the "strip," each of which may be planar (i.e., two-dimensional) and/or curved (i.e., three-dimensional), each of which may also be arranged in a segment, a roll, and the like. The terms "braid" and "braided article" collectively refer to any elongated article which is braided in such a manner that the "braid" or "braided article" consists of at least two "wires" or "strips" in a cross-section normal to a longitudinal axis of the "braid" or "braided article," where examples of such articles may include, but not be limited to, a thread, a yarn, any other articles made by conventional "braid" techniques, and the like. The term "mesh" also collectively refers to a mesh, a net, a screen, a quilt, a fabric, a garment, any other articles in a networking, woven, and/or interwoven structure. It is to be understood that at least a portion of each of such articles formed according to the foregoing terms in this paragraph may be arranged to be solid, hollow or porous such as, e.g., a foam, a sponge, and so on. It is also to be understood that each of such articles formed according to the foregoing terms of this paragraph may be arranged to include (or define) at least one hole, gap or opening.

Similarly and as used herein, the term "mixture" collectively refers to a liquid, a solution, a sol, a gel, an emulsion, a suspension, a slurry, and/or a powder, each of which may include therein multiple particles, particulates, grains, granules, filings, fragments, and/or pellets each of which may also have shapes of spheres, ellipsoids, cylinders, flakes, "wires," "strips," and the like, and each of which may be in a range of millimeters, microns or nanometers. When appropriate, such a "mixture" may include at least one solvent, at least one chemically, electrically, and/or magnetically inert filler for the purpose of providing mechanical strength and/or integrity thereto, and so on.

Unless otherwise defined in the following specification, all technical and scientific terms used herein have the same meaning as commonly understood by one of ordinary skill in the art to which the present invention belongs. Although the methods or materials equivalent or similar to those described herein can be used in the practice or in the testing of the present invention, the suitable methods and materials are described below. All publications, patent applications, patents, and/or other references mentioned herein are incorporated by reference in their entirety. In case of any conflict, the present specification, including definitions, will control. In addition, the materials, methods, and examples are illustrative only and not intended to be limiting.

Other features and advantages of the present invention will be apparent from the following detailed description, and from the claims.

DETAILED DESCRIPTION OF THE PREFERRED EMBODIMENTS

Figure 1A:
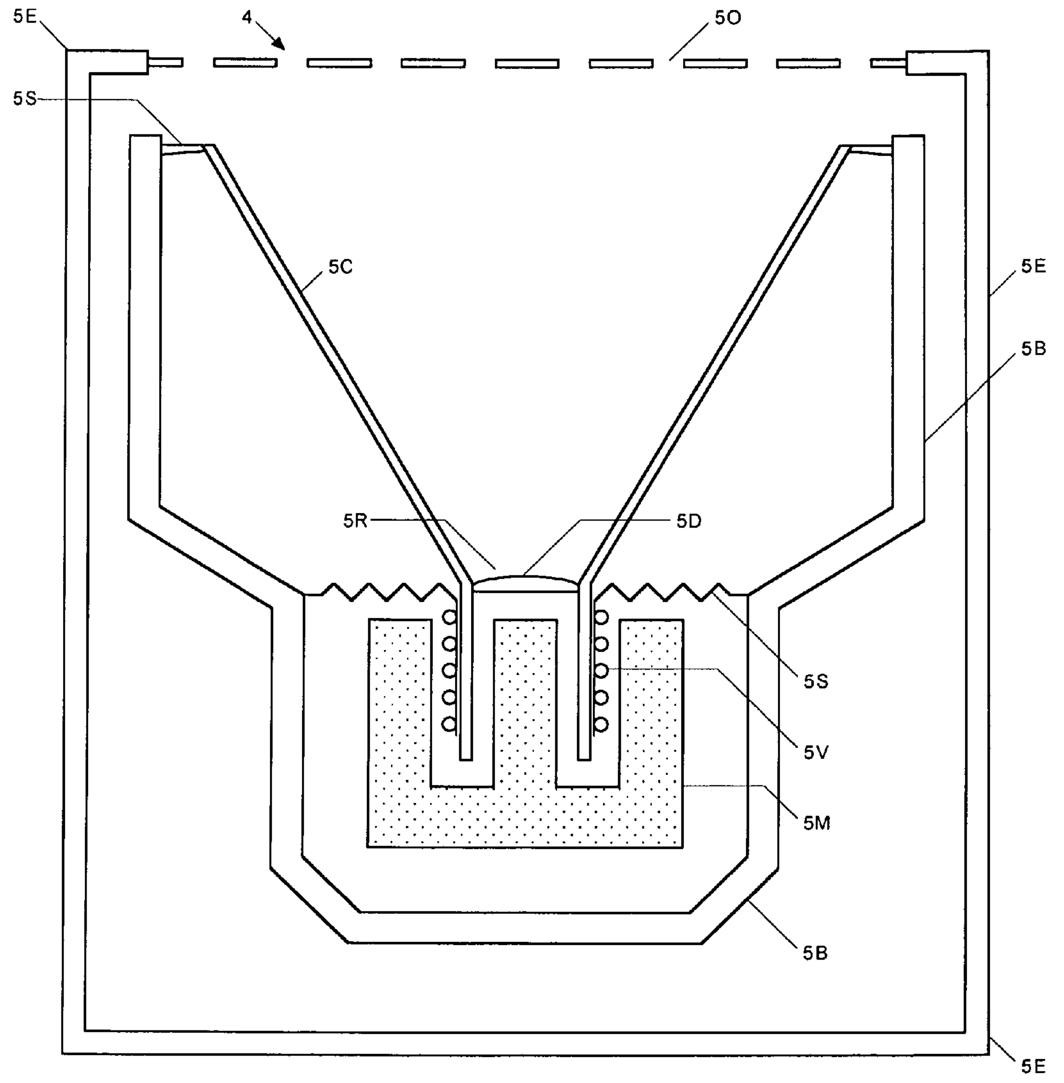
FIG. 1A (Prior Art)
FIG. 1A is a cross-sectional view of a conventional speaker device including a drive member irradiating harmful electromagnetic waves therefrom.

The present invention relates to various electromagnetically-countered speaker systems (to be abbreviated as "EMC speaker systems" or simply "systems" hereinafter) capable of generating audible sounds based upon at least one dynamic signal supplied thereto while minimizing irradiation of harmful electromagnetic waves (to be abbreviated as "harmful EM waves" or "harmful waves" hereinafter). More particularly, the present invention relates to an EMC speaker system which includes at least one source of such harmful waves (i.e., a drive member) and at least one counter member, where such a source does not include any permanent magnets but is capable of generating such sounds, while the counter member interacts with the drive member for generating such sounds while irradiating counter electromagnetic waves (to be abbreviated as "counter EM waves" or "counter waves" hereinafter) capable of canceling at least a substantial (or only a) portion (to be referred to as a "desirable portion" hereinafter) of the harmful waves based on their phase characteristics. Such a counter member may be formed in various shapes and receive various signals with preset amplitudes and flowing in preset directions therealong. The counter member may be disposed in various locations with respect to the drive member in various arrangements as far as the counter waves irradiated thereby may cancel the desired portion of the harmful waves. The present invention also relates to an EMC speaker system which has at least one electric shield and/or at least one magnetic shield capable of shielding and/or terminating electric waves and magnetic waves of the harmful electromagnetic waves, respectively, where the electric shield may include electrically conductive material, while the magnetic shield may include magnetically permeable material and at least one optional magnet and shunt.

The present invention relates to various methods of generating the sounds without including a permanent magnet in the drive member of an EMC speaker system while minimizing irradiation of such harmful waves irradiated by the drive member by canceling the desired portion of the harmful waves by the counter waves emitted by the counter member. More particularly, the present invention relates to various methods of generating repulsive and/or attractive forces with the first electromagnet of the drive member and the second electromagnet of the counter member and providing the audible sounds by such forces while canceling the desired portion of the harmful waves from the first electromagnet with the counter waves which are generated by the second electromagnet. To this end, the present invention provides various methods of generating by the counter member such counter waves which define preset amplitudes and/or phase angles for canceling the desired portion of the harmful waves, various methods of fabricating such a counter member in a preset shape and/or size to generate such counter waves, various methods of arranging the counter members with respect to the drive member for generating such counter waves, various methods of supplying to the counter member the dynamic signals having preset amplitudes and flowing in a preset direction therealong to generate the counter waves, various methods of manipulating the amplitudes and/or phase angles of the counter waves to cancel the desired portion of such harmful waves, various methods of manipulating such amplitudes and/or directions of the dynamic signals and emitting such counter waves capable of canceling such a desired portion of the harmful waves, and the like. The present invention may also relate to various methods of shielding and eliminating electric waves of such harmful waves using at least one electric shield, various methods of rerouting or optionally terminating magnetic waves of such harmful waves by at least one magnetic shield, and various methods of shielding such harmful waves by at least one electromagnetic shield which is an unitary article incorporating thereinto both of the above electric and magnetic shields. The present invention also relates to various methods of manipulating the counter member to not only maximize an extent of canceling the harmful waves by the counter waves but also optimize an efficiency of converting the dynamic signals into the audible sounds.

The present invention further relates to various processes for providing the speaker systems capable of minimizing irradiation of such harmful EM waves by their speakers. More particularly, the present invention relates to various processes for making the counter members capable of irradiating such counter waves capable of canceling a desired portion of such harmful waves based upon their amplitudes and phase angles, various processes for making the counter members receiving external currents or signals in preset directions, various processes for supplying such currents or signals of preset amplitudes and/or directions, various processes for making the counter members incorporated into various locations of the wave sources, various processes for making the counter members for emitting such counter waves aligned with such harmful waves in preset relations, various processes for making the counter member to be in preset relation to the wave source, and the like. The present invention may also relate to various processes for making the electric and magnetic shields capable of shielding the electric and magnetic waves of the harmful waves.

The present invention further relates to EMC speaker systems each of which includes at least two speakers which may be incorporated into the same case member or, alternatively, may instead be provided as separate articles. In addition, this invention relates to EMC microphone systems capable of minimizing irradiation of the harmful waves by similar counter members while converting the sounds into the dynamic signals.

The EMC speaker systems of the present invention may be fabricated in various embodiments. For example and as described above, such EMC speaker systems may be provided as earphones or headphones which may be disposed adjacent to or into ears of the users. The EMC speaker systems may also be incorporated into portable mobile or cellular phones, handsets of wired phones, and other communication devices such as walkie-talkies, and the like. Such EMC speaker systems may also be incorporated into other portable audio devices such as, e.g., portable tape players, CD players, DVD players, mp3 players, and the like. Such EMC speaker systems may be incorporated into speakers of consoles of various audiovisual devices examples of which may include, but not be limited to, TVs, CD players, DVD players, game machines, computers, and other electric or electronic devices designed to generate audible sounds, electric or optical signals representing such sounds, and so on. Whether used proximate to or at preset distances from the users, various EMC speaker systems of the present invention may effectively reduce the irradiation of the harmful waves to the user.

The EMC speaker systems of the present invention may be used in pairs or in greater numbers as well. Accordingly, multiple EMC speaker systems may be encased in a single case member, where each speaker system may be able to cancel the desired portion of the harmful waves generated by its wave source, where two or all of the speaker systems may be arranged to share a common counter member, a common electric and/or magnetic shield, and the like. Alternatively, multiple EMC speaker systems may be provided as separate articles, where such speaker systems may be disposed in a preset arrangement, where the speaker systems may be disposed in an arbitrary arrangement while manipulating its common counter member or their individual counter members to irradiate such counter waves capable of canceling the desired portion of the harmful waves.

Basic principles of the EMC speaker systems and counter members of such systems may be modified and applied to microphone systems. For example, such a microphone system may include at least one counter member which may be similar to that of the speaker system and emit counter waves capable of canceling at least a portion of harmful waves emitted by one or more wave sources of the microphone system. In the alternative, the microphone system may include at least one electric shield or magnetic shield capable of absorbing and eliminating electric and magnetic waves of such harmful waves, respectively. In addition, such EMC microphone system and speaker system may be encased in a single case member and used as an assembly of a receiver and a transmitter, where each of the systems may include its own counter member for canceling the desired portion of the harmful waves or where a single counter member may be arranged to cancel the desired portion of a sum of harmful waves from both systems.

Various aspects and/or embodiments of various systems, methods, and/or processes of this invention will now be described more particularly with reference to the accompanying drawings and text, where such aspects and/or embodiments thereof only represent different forms. Such systems, methods, and/or processes of this invention, however, may also be embodied in many other different forms and, accordingly, should not be limited to such aspects and/or embodiments which are set forth herein. Rather, various exemplary aspects and/or embodiments described herein are provided so that this disclosure will be thorough and complete, and fully convey the scope of the present invention to one of ordinary skill in the relevant art.

Unless otherwise specified, it is to be understood that various members, units, elements, and parts of various systems of the present invention are not typically drawn to scales and/or proportions for ease of illustration. It is also to be understood that such members, units, elements, and/or parts of various systems of this invention designated by the same numerals may typically represent the same, similar, and/or functionally equivalent members, units, elements, and/or parts thereof, respectively.

FIG. 1A is a cross-sectional view of a conventional speaker device including a drive member irradiating harmful waves therefrom. In general, the device 4 includes a case member or enclosure 5E forming multiple openings 5O on one side (or front). Inside the case member 5E is disposed a bracket 5B which is typically made of a metal and coupled to the case member 5E by various means. A drive member 5R is disposed inside and movably supported by the bracket 5B, where the drive member 5R consists of a cone or diaphragm 5C, a voice coil 5V, and a speaker magnet 5M. The cone 5C is made of paper, plastic, metal or other light materials and forms a wider end and a narrower end, where the wider end is disposed near the front of the case member 5E, while the narrower end is oriented to an opposite side (or rear) of the case 5E. The wider end of the cone 5C is attached to the bracket 5B by a suspension or a surround 5S which is a rim of a flexible material movably incorporated between the bracket 5B and cone 5C. Therefore, such a suspension 5S allows the cone 5C to move toward and away from the front of the case member 5E. The narrower end of the cone 5C is then attached to the voice coil 5V which is a wound coil of an electrically conductive wire. The voice coil 5V is generally attached to the bracket 5B by a spider 5S which is a ring of a flexible material. Therefore, the spider 5S holds the voice coil 5V in position but allows the voice coil 5C to move toward and away from the front of the case member 5E. Such a speaker magnet (or simply "magnet") 5M is a permanent magnet and defines a shape of an annular ring with (or without) a center core, where the voice coil 5V may be preferably disposed in a gap defined in the magnet 5M such that the voice coil 5V may be disposed inside static magnetic fields created by the magnet 5M. A dust cap 5D is made of any rigid or flexible material and encloses the narrower end of the cone 5C.

In operation, the voice coil 5V is disposed inside the gap formed inside the speaker magnet 5M in its rest position which is generally determined by a weight of the cone 5C and voice coil 5V, elastic properties of the suspension 5S, orientation of the case 5E, and the like. Dynamic electric signals are then supplied to the voice coil 5V, where such signals typically carry information about a voice, music, and the like. As the dynamic signals flow therein, the voice coil 5V generates dynamic magnetic fields of which strengths and directions may depend upon various factors such as, e.g., amplitudes of the signals, directions of such signals, a direction of winding of the coil 5V, and disposition of the coil 5V. By manipulating such factors, the voice coil 5V may be arranged to define the dynamic magnetic fields which may repel and attract the static dynamic fields of the magnet 5M while moving with the cone 5C back and forth. As a result, the cone 5C compresses air when it moves outward toward the front of the case 5E to its extended position, and rarefies air when it recoils back to its rest position. Thereby, the drive member 5R generates audible sounds and transmits such sounds toward an user situated in front of the case member 5E through the openings 5O. Concurrent therewith, the fluctuating or time-varying dynamic signals flowing through the voice coil 5V also generate fluctuating electric fields and magnetic fields, thereby irradiating the harmful electromagnetic waves or EM waves containing 60 Hz (or 50 Hz) components. When the user is situated at a greater distance from the voice coil 5V, such harmful waves may be attenuated when they impinge upon the user. However, when the device 4 is to be used as an earphone, a headphone, and/or a speaker of a communication device, such harmful waves may impinge upon brain cells of the user at significant strengths, thereby causing hazardous results.

Various EMC speaker systems of the present invention are designed to prevent irradiation of such harmful EM waves onto the user regardless of the distances between the systems and user.

Figure 1B:
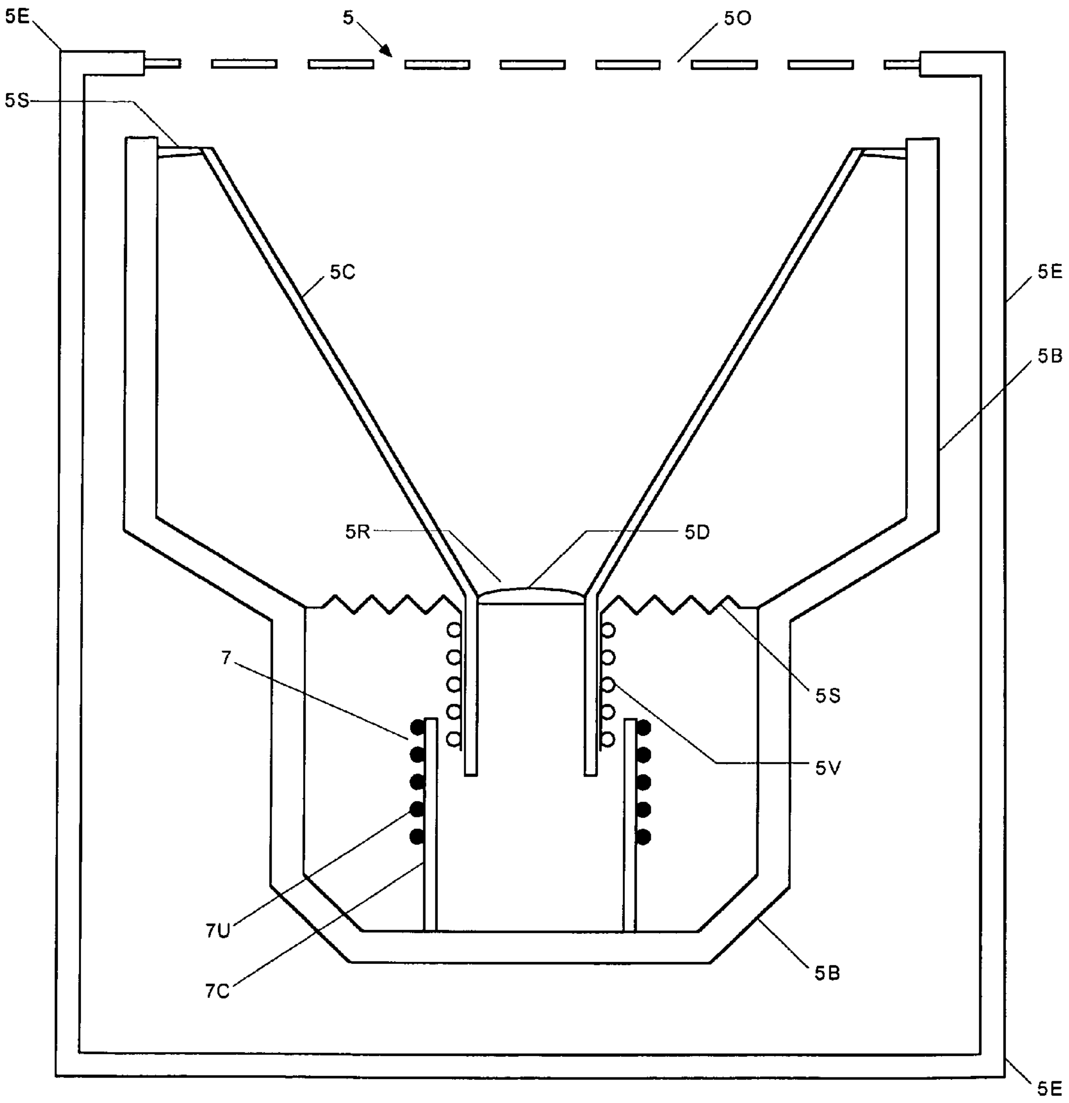
FIG. 1B is a cross-sectional view of an exemplary speaker system which has a drive member which not including any conventional speaker magnet but still irradiating such harmful electromagnetic waves and a counter member irradiating counter electromagnetic waves capable of canceling such harmful waves according to the present invention.

In one aspect of the present invention, an EMC speaker system may be provided by replacing the speaker magnet the conventional speaker device of FIG. 1A by at least one counter member. FIG. 1B is a cross-sectional view of an exemplary speaker system with a drive member which does not including any conventional speaker magnet but still irradiating such harmful waves and which includes a counter member irradiating counter electromagnetic waves capable of canceling a desired portion of the harmful waves according to the present invention. An exemplary EMC speaker system 5 may be generally similar to the speaker device 4 of FIG. 1A in that such a system 5 includes a case member or enclosure 5E which forms multiple openings 5O through its front and that a drive member 5R including a cone 5C and a voice coil 5V (but no speaker magnet) may be disposed in and supported by a metal bracket 5B which is in turn disposed inside and supported by the case member 5E. Such a cone 5C is also made of paper, plastic, metal, and/or other light materials and forms a wider end and a narrower end, where the wider end is disposed near the front of the case member 5E, while the narrower end is disposed toward an opposite side or a rear of the case member 5E. The wider end of the cone 5C is attached to the bracket 5B by a suspension 5S which is a flexible rim disposed between the cone 5C and bracket 5B. Therefore, the suspension 5S allows such a cone 5C to move toward and away from the front of the case member 5E. The narrower end of the cone 5C is attached to the voice coil 5V which is a wound coil of an electrically conductive wire. The voice coil 5V is typically attached to the basket 5B by a spider 5S which is a ring of a flexible material. Therefore, the spider 5S holds the voice coil 5V in position but allows the voice coil 5V to move back and forth from the case front. The drive member 5R does not include any speaker magnet of the device of FIG. 1A. A dust cap 5D may be made of any rigid or flexible materials and enclose the narrower end of the cone 5C.

The EMC speaker system 5 also includes a counter member 7 including a single counter unit 7U and a single coupler 7C. The counter unit 7U is generally made of an electric conductor wound into a shape of a coil and disposed around at least a portion of the voice coil 5V. The coupler 7C is fixedly coupled to an inner surface or wall of the bracket 5B and receives the counter unit 7U therein so as to keep the counter unit 7U in a desired position. Accordingly, such a counter unit 7U may preferably be disposed inside the case member 5E in a preset relation with respect to the drive member 5R.

In operation, the voice coil 5V is provided as a first electromagnet which defines a shape of a solenoid and which is incorporated around the narrower end of the cone 5C. In its rest position, the voice coil 5V does not receive any dynamic signals, where such a position is typically determined by a weight of the cone 5C and voice coil 5V, elastic properties of the suspension 5S, orientation of the case member 5E, and the like. The coupler 7C is incorporated onto an inner surface of a bottom of the bracket 5B and disposed in an arrangement of enclosing at least a portion of the voice coil 5V therein. The counter unit 7U is provided as a second electromagnet which also defines a shape of a solenoid as well and which is disposed around the coupler 7C in order to enclose at least a portion of the voice coil 5V therein. As both electromagnets are in position, the dynamic signals are supplied to the voice coil 5V and counter unit 7U, where the same signals may flow through the voice coil 5V and then the counter unit 7U (or vice versa) or, in the alternative, such signals may be provided to the voice coil 5V and coupler unit at least substantially simultaneously. When the signals flow therein, the voice coil 5V generates first dynamic magnetic fields therearound of which strengths and/or directions may depend upon various factors such as, e.g., amplitudes of such signals, directions of such signals, a direction of the winding of the coil 5V, and/or disposition of the coil 5V. The counter unit 7U similarly generates second dynamic magnetic fields therearound when the signals flow therein, where strengths and/or directions of such fields may depend upon various factors such as, e.g., amplitudes of such signals, directions of such signals, a direction of the winding of the counter unit 7U, disposition of the counter unit 7U, and the like. By disposing the second electromagnet of the counter unit 7U in a preset relation to the first electromagnet of the voice coil 5V, such first and second magnetic fields may interact each other while generating repulsive and/or attractive forces therebetween determined by, e.g., temporal characteristics of such signals supplied thereto. Due to such forces, the cone 5C compresses air as it moves outward toward the front of the case 5E to its extended position, and rarefies air as it recoils back to its rest position. Thereby, the drive member 5R generates acoustic sounds and transmits the sounds toward an user.

The fluctuating and/or time-varying dynamic signals supplied to such a voice coil 5V inevitably generate therearound fluctuating electric fields as well as magnetic fields, thereby irradiating harmful electromagnetic waves (or "harmful EM waves" or simply "harmful waves") containing therein 60 Hz (or 50 Hz) components. Concurrently therewith, similar dynamic signals flowing in the counter unit 7U also generate time-varying electric fields and magnetic fields therearound, thereby irradiating counter electromagnetic waves (or "counter EM waves" or simply "counter waves") also containing therein 60 Hz (or 50 Hz) components. Thus, at least a substantial portion or only a preset portion (or "a desired portion" hereinafter) of such harmful waves may be canceled by the counter waves by manipulating one or more of various factors such as, e.g., shapes and/or sizes of the electromagnets of the drive and counter members, arrangement and/or orientation between such electromagnets, such a relation between the electromagnets, amplitudes and/or directions of the signals flowing in one or both of the electromagnets, and the like. Accordingly, the second electromagnet of the counter unit 7U may not only provide the repulsive and/or attractive forces required for generating the audible sounds but also irradiate the counter waves required for canceling the desired portion of the harmful waves.

It is appreciated that such electromagnets of the embodiment of FIG. 1B may be deemed to be disposed concentrically, i.e., at least a portion of the first electromagnet is enclosed within the second electromagnet and may also be deemed to be disposed side by side thereto, i.e., such electromagnets are aligned with each other or longitudinal axes of such electromagnets are arranged to coincide with each other. It is, accordingly, preferred that adjacent poles of such electromagnets (e.g., a bottom of the first electromagnet and a top of the second electromagnet) may define like poles when the signals flow therethrough and that such electromagnets may generate the sounds not by the attractive forces but by the repulsive forces provided by the interacting dynamic magnetic fields of the electromagnets. Thereafter, each electromagnet may be wound in preset directions and the signals may be supplied in preset directions for the purpose of defining such like poles when the signals flow through both of the electromagnets. Depending upon details of the configurations and/or arrangements thereof, the first and second electromagnets may also be arranged to utilize the attractive forces for not only generating such sounds but also irradiating such counter waves capable of canceling the desired portion of the harmful waves.

Figure 1C:
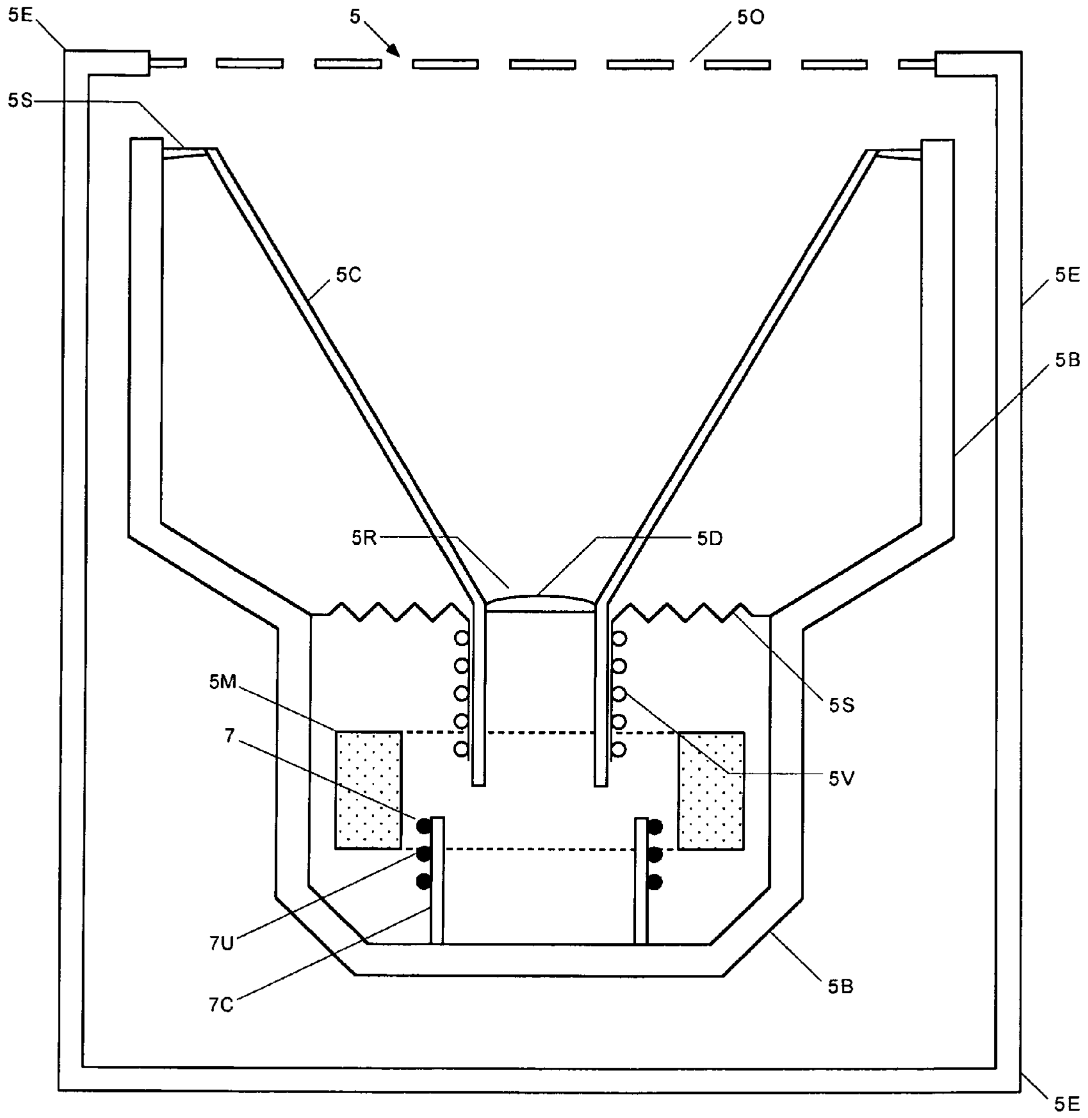
FIG. 1C is a cross-sectional view of an exemplary speaker system, which has a drive member including a smaller speaker magnet and irradiating such harmful electromagnetic waves and a counter member emitting counter electromagnetic waves capable of canceling such harmful waves according to the present invention.

In another aspect of the present invention, an EMC speaker system may further be provided by supplementing the counter member of FIG. 1B with at least one permanent speaker magnet commonly used in the conventional speaker device. FIG. 1C is a cross-sectional view of an exemplary speaker system with a drive member and counter member, where the drive member includes a small speaker magnet and irradiates such harmful electromagnetic waves and where the counter member irradiates such counter electromagnetic waves capable of canceling the desired portion of the harmful waves according to the present invention. An exemplary EMC speaker system 5 may be generally deemed to be a combination of the conventional speaker device of FIG. 1A and the novel speaker system of FIG. 1B in that a drive member 5R includes a permanent speaker magnet 5M and that the system 5 includes a counter member 7 with a coupler 7C as well as a counter unit 7U, where the latter is arranged to be disposed in a preset geometric and/or operational relation to the drive member 5R. More particularly, the counter unit 7U may be disposed around the coupler 7C which is similar or identical to that of FIG. 1B in an arrangement that the counter unit 7U does not enclose therein any portion of the voice coil 5V but that such a counter unit 7U is rather enclosed within at least a portion of the speaker magnet 5M. Accordingly, the first electromagnet of the drive member 5R generates therearound the first dynamic magnetic fields which may interact not only with the second dynamic magnetic fields generated by the second electromagnet of the counter unit 7U but also with the static magnetic fields generated around the magnet 5M. As a result, at least a major or substantial portion of such repulsive and/or attractive forces responsible for generating the audible sounds may be provided by the interaction between the first and second electromagnets, while the remaining portion of such forces may be supplemented by another interaction between the speaker magnet 5M and first and/or second electromagnets. In this respect, the EMC speaker system of FIG. 1B may offer a benefit of constructing a smaller and lighter speaker system, while the EMC speaker system of FIG. 1C may offer a benefit of constructing another speaker system which may be smaller and lighter than a conventional counterpart defining equivalent capabilities but may instead be a little bit bigger and heavier than that of FIG. 1B. Other configurational and/or operational characteristics of the EMS speaker system of FIG. 1C may be similar or identical to those of FIGS. 1A and 1B.

Configurational and/or operational variations and/or modifications of the speaker systems, their counter members, counter units, and other portions exemplified in FIGS. 1B and 1C also fall within the scope of this invention.

It is appreciated that various EMC speaker systems of this invention is to be differentiated from those of the co-pending Applications. First of all, a major difference between various EMC systems of this invention and various electromagnetically-shielded systems (or "EMS systems" hereinafter) of the above co-pending Applications lies in the fact that the dynamic magnetic fields of the voice coil of the latter EMS system typically interact with the static magnetic fields of the speaker magnet but not with the dynamic magnetic fields generated by the counter member. Therefore, the movable cone of such an EMS system may vibrate solely through the repulsive and/or attractive forces generated by such interaction between the voice coil and the speaker magnet. In contrary, the dynamic magnetic fields of the voice coil of the EMC speaker system of this invention interact only with the dynamic magnetic fields of the counter unit but typically not with the static magnetic fields of the speaker magnet, for the EMC speaker system may not include any of such magnets. Even when the drive member of the EMC speaker system of this invention may include the speaker magnet, such dynamic magnetic fields of the voice coil of the EMC system have to interact not only with the static magnetic fields of the magnet but also with the dynamic magnetic fields of the counter member, for the counter member of such an EMC system is to be disposed in the above preset relation which ensures that the second electromagnet is to be disposed in the preset arrangement, in the preset orientation, in the distance, and the like. Thus, the movable cone of the EMC speaker system of the present invention vibrate solely by the repulsive and/or attractive forces generated by such interactions between the first and second electromagnets (if the driver member does not include any permanent magnet) or, in the alternative, by such repulsive and/or attractive forces generated by such interactions among the speaker magnet as well as the first and second electromagnets (if the driver member does include at least one speaker magnet therein). Secondly, the counter member of the EMS speaker system of the co-pending Applications is arranged to be disposed in one preset relation with respect to the drive member and to emit the counter waves but not to interfere with the interaction between the dynamic fields of the voice coil and static magnetic fields of the speaker magnet. In contrary, the counter member of the EMC speaker system of this invention is disposed in another preset relation enough to intentionally interfere with or to even interact with the dynamic magnetic fields generated by the voice coil, thereby providing the repulsive and/or attractive forces as well as irradiating the counter waves.

The EMC speaker system of this invention may be readily differentiated from the EMS speaker system of the co-pending Applications rather quantitatively. In the EMS speaker system, magnitudes of the repulsive and/or attractive forces generated by such dynamic magnetic fields of the voice coil which interact with the static magnetic fields of the speaker magnet are generally proportional to the amplitudes of the signals or currents in the power of about 1.0, because the strengths of such static magnetic fields are constant and because the strengths of the dynamic magnetic fields are generally proportional to the amplitudes of the signals flowing therein. In contrary, magnitudes of the repulsive and/or attractive forces generated by such interacting magnetic fields of two electromagnets may be generally proportional to the amplitudes of the signals in the power of about 2.0 (in an ideal case) or somewhat less than 2.0, because the strengths of the dynamic fields are proportional to a product of the amplitudes of the signals, one for those flowing in the first electromagnet and another for those flowing in the second electromagnet. When the drive member includes the permanent magnet which also intervenes in generating such forces, the magnitudes of such forces may still be proportional in the power of about 2.0 or so while defining a positive or negative offset depending upon orientation and/or configuration of such a magnet, may be proportional in the power greater than 2.0 or so when the static magnetic fields of the magnet may augment such forces, may be proportional in the power which is less than 2.0 but greater than 1.0 when the static magnetic fields of the magnet may reduce such forces, and the like. Accordingly, the proportion between the magnitudes of such forces and the amplitudes of the signals or currents may delineate whether or not the system is the EMS speaker system of the co-pending Applications (when the proportion turns out to be about 1.0), the system is the EMC speaker system of this invention (when the proportion is greater than 1.0), and the like.

As described above, the counter member may be provided to satisfy the preset relation to the source of the harmful waves such as the drive member of the system. The relation within the scope of this invention collectively refer to various factors examples of which may include, but not be limited to, a shape and/or a size of the voice coil, a shape and/or a size of the permanent speaker magnet (if any), a shape and/or a size of the counter member and/or counter unit, an orientation of the voice coil, an orientation of the permanent speaker magnet (if any), an orientation of the counter member and/or counter unit, an arrangement of the voice coil, an arrangement of the magnet (if any), an arrangement of the counter member and/or counter unit, amplitudes of the signals supplied to the drive member and counter member (and/or unit), directions of the signals flowing through the drive member and counter member (and/or unit), and the like.

The counter member of the EMC speaker system of this invention may be provided in various shapes and/or sizes which may be determined by various factors such as, e.g., shapes and sizes of the drive member (including those of the voice coil as well as the speaker magnet if any), amplitudes and/or directions of the signals flowing in the drive and/or counter members and other portions of the system, an orientation of the drive member (including that of the voice coil as well as magnet if any), a number of drive members in the system, other electrical wiring of the speaker system, and so on. It is appreciated that a major source of the harmful waves is the voice coil of the drive member but that the harmful waves may also be dispersed through the speaker magnet if any. In addition, other electrical wiring may irradiate such harmful waves which may have wave characteristics different from those irradiated by the voice coil and speaker magnet (if any), although such waves may also include the 60 Hz (or 50 Hz) components. Therefore, such a counter member may be designed to effectively cancel as much a portion of all of these harmful waves.

In general, the counter member may define a configuration which conforms to that of the drive member so that the counter waves irradiated by the counter member may match various propagation characteristics of the harmful waves and effectively cancel the desired portion of the waves. To this end and as depicted in FIGS. 1B and 1C, the counter member may be disposed around a periphery of the drive member, preferably in an arrangement conforming or similar to the shape and/or size of the drive member. In some instances, the counter member may be shaped and sized to conform to only a portion of the drive member when it is impractical to devise a conforming configuration due to space limitation inside the case member or bracket, complicated geometry of the drive member, and so on. In the alternative, the counter member may instead define a symmetric configuration, may define another configuration not exactly conforming to that of the drive member but at least partially symmetric to the drive member. In another alternative, such a counter member may define an asymmetric configuration, may define another configuration at least partially asymmetric to the drive member, and so on. In all of these examples, it is appreciated that the EMC speaker system may include a single or multiple counter members or may include a single or multiple sources of the harmful waves in its drive member and in other portions thereof and that each of such multiple counter members may be similarly shaped and/or sized as described in this paragraph. It is appreciated that the foregoing conforming and/or symmetric configuration of the counter member may be generally preferred to emit the counter waves capable of canceling the desired portion of such harmful waves irradiated by a single wave source or a single drive member (which is to be referred to as "local canceling" hereinafter) but that the non-conforming and/or asymmetric configuration of the counter member may be suited to irradiate the counter waves capable of canceling the desired portions of a sum of the harmful waves irradiated by multiple wave sources or multiple drive members of a single speaker system or multiple speaker systems (which is to be referred to as "global canceling" hereinafter). Depending on detailed configurations, however, the conforming or symmetric configuration may be better suited for the global canceling, whereas the non-conforming or asymmetric configuration may be preferred for the local canceling.

In addition to its configurations, the counter member may be disposed in various arrangements with respect to the drive member. For example, the counter member may be arranged to enclose only a portion, to enclose an entire portion of the drive member, to be disposed side by side with respect to the drive member, to be disposed in other non-enclosing patterns, and so on. In another example, the counter member may be disposed in an arrangement symmetric to only a portion or an entire portion of the drive member, in another arrangement asymmetric to only a portion or an entire portion of the drive member, and the like. In all these examples, it is appreciated that the EMC speaker system may include a single or multiple counter members, may include a single or multiple sources of such harmful waves in its drive member and/or in other portions thereof, and the like, and that each of such multiple counter members may then be similarly arranged as described in this paragraph. It is also appreciated that the above enclosing or symmetric arrangement of the counter member may be generally preferred to emit such counter waves capable of canceling the desired portion of such harmful waves irradiated by a single wave source or a single drive member (i.e., the "local canceling") but that the non-enclosing or asymmetric arrangement of the counter member may be preferable for irradiating the counter waves capable of canceling the desired portions of the sum of the harmful waves irradiated by multiple wave sources or multiple drive members of a single speaker system or multiple speaker systems (i.e., the "global canceling"). Depending upon detailed configurations, however, such enclosing or symmetric configuration may be better suited for the global canceling, whereas the non-enclosing or asymmetric configuration may be preferred for the local canceling.

It is to be understood that the counter member may be configured in various shapes and sizes, may be disposed in various arrangements, may include various numbers of counter units therein, and may be provided in any number, as long as such counter EM waves irradiated thereby may cancel the desired portion of the harmful waves. Other details of the counter members and/or their counter units are to be disclosed below in conjunction with FIGS. 2A through 2X.

While the shape, size, and/or arrangement of such a counter member may dictate propagation characteristics of such counter waves, their phase angles may be decided by a direction of electric signals flowing in the counter member and an orientation of the counter member with respect to the drive member, while their amplitudes may be determined by amplitudes of the currents flowing in the counter member and a distance between the counter member and the user. For example, the counter member may receive the currents of amplitudes less than those of the signals flowing in the voice coil while irradiating such counter waves capable of effectively canceling such harmful waves when the counter member is disposed closer to the user, when the counter member may include more windings than the voice coil, when the counter member may include more layers of coils than the voice coil, and so on. Conversely, the counter member may receive the currents of amplitudes greater than those of the signals flowing in the voice coil while emitting the counter waves capable of effectively canceling the harmful waves when the counter member may be disposed farther away from the user, when the counter member may include less windings than the voice coil, when the counter member may include less layers of coils than the voice coil, and the like.

The counter member may operate on various sources of electric currents. In one example, the dynamic signals may be supplied to the counter member so that the same signals may flow in both of the counter member and voice coil. Such an arrangement may be embodied by electrically connecting the voice coil with the counter member in series, where the dynamic signals may first flow in such a counter member and then through the voice coil (or vice versa) and where an optional resistor may be disposed therebetween in order to regulate voltage thereacross. In another example, only a portion of the dynamic signals may be supplied to the counter member where this arrangement may be embodied by electrically connecting the voice coil and the counter member in parallel, by diverting such a portion of the dynamic signals through the counter member, and so on. Thus, different portions of the signals may flow through the counter member and voice coil simultaneously or sequentially. When desirable, an optional resistor may be disposed along the connection so as to regulate voltage thereacross. The counter member of all of these examples may then generate the counter waves which have temporal characteristics identical or at least substantially similar to those of the harmful waves and, therefore, cancel the desired portion of the harmful waves. In another example, such a counter member may be supplied with external electric signals (e.g., currents or voltages) which may not be directly obtained or derived from the dynamic signals as well.

Such internal or external signals may flow in the counter member in various directions as well, where such directions may be generally determined by configurations and/or orientations of the voice coil and counter member. Therefore, when the voice coil and counter member are wound in the same direction, such signals may flow therein along opposite directions. Conversely, as the voice coil and counter member are wound along the opposite directions, the signals may flow therein along the same direction.

The counter member may be incorporated into various locations and orientations of such EMC speaker system with respect to the drive member, the user, and the like. First, such dispositions may be characterized based upon distances between the user and the counter member and between the user and the drive member. For example, such a counter member may be disposed from the user at a distance which may be equal or at least substantially similar to a distance between the user and the drive member. Accordingly, when viewed from the user, the counter member and drive member may be disposed flush with each other. In another example, the counter member may be disposed closer to (or farther from) the user than the drive member. In such an example, the amplitudes of the counter waves irradiated by the counter member may be adjusted by manipulating such configurations of the counter member and/or amplitudes of the currents or signals flowing through the counter member for the purpose of equalizing the amplitudes of such counter waves with those of such harmful waves when measured at the user, rendering such counter waves have greater or less amplitudes than the harmful waves when measured thereat, and the like. Secondly, such dispositions may be defined in terms of individual portions of the system, where such counter members may be disposed on or over exterior and/or interior surfaces of such portions or may be incorporated into such portions. Thirdly, the counter member may be disposed in various orientations with respect to the user when compared with the drive member. In one example, the counter member may be disposed in an orientation so that the counter waves irradiated thereby may align with such harmful waves for maximizing cancellation of such harmful waves. It is appreciated that the drive member and its voice coil and magnet (if any) may be disposed in various orientation with respect to the case member and that the counter member may be disposed accordingly. In another example, the counter member may be disposed in another orientation which may align with that of the drive member or its voice coil and magnet (if any). In this example, the counter waves emitted by the counter member may be arranged to not perform the local canceling but to rather perform the global canceling so that the counter waves may cancel the desired portion of the sum of the harmful waves emitted by multiple sources. In another example, the counter member may be intentionally misaligned with the drive member or its voice coil and magnet (if any) so that the counter waves may cancel only a portion of the harmful waves. Details of such dispositions and/or orientations of the counter member and/or counter units thereof are provided in conjunction with FIGS. 3A to 3L.

As briefly described above, the counter member may be arranged to selectively cancel only a desired portion of such harmful waves. First, such a counter member may be arranged to selectively cancel the desired portion of the harmful waves regardless of their frequency components. That is, the counter waves irradiated by the counter member may cancel a preset portion or percentages of the harmful waves typically across an entire spectrum of the harmful waves. To this end, the counter member may have a preset configuration, may be disposed at a preset distance, may be supplied with the currents or signals of preset amplitudes, and the like, such that the counter waves may define the amplitudes less than those of the harmful waves when measured at the user. In the alternative, such a counter member may be arranged to emit the counter waves with the amplitudes greater than those of the harmful waves when measured thereat. Secondly, such a counter member may be arranged to selectively cancel only desired frequency components of the harmful waves. That is, the counter waves emitted by the counter member may cancel the desired portion or as much a portion of specific frequency components of the harmful waves, while leaving intact other frequency components of the harmful waves. To this end, such a counter member may be made of or include at least one material which is not present in the drive member, its voice coil, and/or its speaker. Alternatively, the counter and drive members may define compositions which may be at least slightly different from each other. Therefore, the counter waves emitted by the counter member may cancel only a portion or as much a portion of the desired frequency components of such harmful waves such as, e.g., 60 Hz (or 50 Hz) components, while leaving the potentially beneficial various infrared rays intact. When desirable, the counter member may also be arranged to emit such beneficial rays, where details of such frequency-specific cancellation and/or frequency-specific augmentation have been disclosed in the co-pending Applications.

The counter member may further include at least one insert therearound, where such an insert may be any magnetically hard or soft material. Therefore, when the external currents or signals flow in the counter member, the dynamic magnetic field generated thereby may be augmented by the insert as commonly employed in conventional electromagnets. The insert may define any shapes and sizes, although such an insert may define a configuration conforming to that of the counter member in order to uniformly augment the dynamic magnetic field of the counter member and to generate such counter waves of which amplitudes may be uniformly increased as well. In this context, the insert may have a symmetrical shape when feasible. It is appreciated that the dynamic magnetic fields generated by or around the counter member may depend upon the configurations of the counter member and insert. It then follows that such an insert may have another configuration which may not conform to that of the counter member, which may have an asymmetric shape, which may not be symmetric with respect to the counter member, and the like, as long as the configurations of the insert and counter member may be manipulated such that both of the insert and counter member may in unison generate the dynamic magnetic fields of a preset configuration and may emit the counter waves with preset characteristics. Accordingly, it is possible to arrange the shape, size, arrangement, and/or orientation of the insert to generate the dynamic magnetic field having the preset shape and to emit such counter waves which may align with or may be misaligned with the harmful waves.

The second electromagnet of the counter member or the counter member itself may further be incorporated in different embodiments. In one example, an entire portion of the counter member may be fixedly coupled to one or more of various portions of the system so that such a counter member may remain stationary when the signals flow therein and while generating the counter waves. In the alternative, at least a portion of the second electromagnet may be arranged to move while receiving the signals therein either directly or through a mobile portion of the counter member. Accordingly, the second electromagnet may then translate, vibrate or otherwise move while generating such counter waves. In one context, such movement of the mobile second electromagnet may be beneficial in that the counter waves may better match the harmful waves which may be generated by the translating or vibrating voice coil, as long as the movement of the second electromagnet is synchronized to that of the voice coil. In another context, such movement may further affect the proportionality between the magnitudes of the repulsive and/or attractive forces of the system and amplitudes of such signals flowing through the first and second electromagnets. For example, such movement may render such a system to become more damped, thereby decreasing the power of the above proportionality. Thus, such an embodiment may be beneficial when it becomes desirable to decrease the dependency of the magnitudes of such forces upon the amplitudes of the signals.

It is appreciated that the major functions of the counter member and/or unit is to provide such repulsive and/or attractive forces for generating the sounds as well as to irradiate the counter waves for canceling the desired portion of the harmful waves in either the local canceling arrangement or in the global canceling arrangement. As described above, various EMC speaker systems of the present invention are to be fabricated as the speakers of the earphones, headphones, and/or other devices to be disposed over or into the ear canal of the user. Therefore, the major target to be protected by the EMC speaker systems of this invention is brain cells of the user and the counter members and units of the EMC speaker systems may be tailored to fit into such devices and to protect the brain cells of the user by canceling as much a portion of the harmful waves.

In another aspect of the present invention, an EMC speaker system may include such counter members defining various configurations and generating the counter waves capable of canceling the desired portion or as much a portion of the harmful waves irradiated by the drive member of such a system. Such counter members may also be provided in various shapes and/or sizes as described heretofore and as will be further elaborated in FIGS. 2A to 2X. It is to be understood that such an EMC speaker system of the present invention may include a single counter member having a single counter unit, a single counter member with multiple counter units, multiple counter members each of which may include a single counter unit or multiple counter units, and the like. Accordingly, each counter member of FIGS. 2A to 2X may also be deemed as a single counter unit, and multiple counter units of a single counter member may also be deemed as an assembly of multiple counter members. In other words, the counter members and counter units may be interchangeably used within the scope of the present invention, where the counter member may also be used to collectively refer to multiple counter units. It is also appreciated for simplicity of illustration that only the narrower ends of the drive members are included in FIGS. 2A to 2X and that the wider ends of such drive members may be disposed on top of or below the narrower ends, thereby respectively transmitting the sounds upwardly or downwardly in the figures. It is further appreciated that the narrower ends of the drive members are represented by cylindrical shapes, although such ends may be embodied in other shapes as well. Such a counter member may be disposed in various geometric relations to the drive member by itself or may instead be received by various couplers capable of maintaining such geometric relations between the counter and drive members. FIGS. 2A to 2L and FIGS. 2S to 2X show various counter members or their units disposed in such relations by themselves, while FIGS. 2M to 2R exemplify various counter members or their units fixated to various couplers, although the former may also be interpreted to be fixated to the couplers which may be omitted from FIGS. 2A to 2L and FIGS. 2S to 2X for simplicity of illustration.

In one exemplary embodiment of this aspect of the invention, various counter members may be fabricated into coils of electrically conductive wires would in various shapes, sizes, and orientations. FIGS. 2A to 2F show schematic views of exemplary counter members which are wound as coils and disposed around the drive member according to the present invention. In one example of FIG. 2A, an exemplary voice coil 5V is wound around the cone in one direction and an exemplary counter member 7 includes a single counter unit 7U which is similarly shaped as a coil of wire which however defines a greater radius of winding and encloses an entire portion of the voice coil 5V therein. In addition, the counter unit 7U is wound at a pitch which is similar or identical to a pitch of the voice coil 5V but in an opposite direction. Therefore, when the dynamic signals flow in the voice coil 5V from the top to the bottom and as such signals also flow in the counter unit 7U along the same direction, the voice coil 5V irradiates the harmful waves of a preset phase angle, and the counter unit 7U generates the counter waves with an opposite phase angle, thereby canceling the desired portion of the harmful waves. It is to be understood that amplitudes of the counter waves may be manipulated by various means. For example, amplitudes of the signals supplied to the counter member and/or configuration of the counter unit 7 may be manipulated in order to render amplitudes of the counter waves equal to, greater than or less than those of the harmful waves. In addition, by manipulating the disposition of the counter unit 7, the amplitudes of such counter waves and harmful waves may be controlled when measured at the user. In another example of FIG. 2B, an exemplary counter unit 7U is similar to that of FIG. 2A, except that the counter unit 7U is wound at a longer pitch than the voice coil 5V. According to the Ampere's law, a number of windings around the counter unit 7U may not change the amplitudes of such counter waves as long as the amplitudes of the dynamic signals flowing therein remain the same. Therefore, the resistance of the counter unit 7U or voltage thereacross may be manipulated to emit the counter waves with suitable amplitudes. Other characteristics of the counter unit 7U of FIG. 2B are similar or identical to those of the counter unit of FIG. 2A. In another example of FIG. 2C, an exemplary counter unit 7U is similar to that of FIG. 2A, except that the counter unit 7U is wound along the same direction as the voice coil 5V. Thus, the dynamic signals may flow in a direction opposite to another direction in which such signals flow in the voice coil 5V, thereby guaranteeing the counter waves to cancel the desired portion of the harmful waves. Other characteristics of the counter unit 7U of FIG. 2C may be similar or identical to those of the counter units of FIGS. 2A and 2B. In another example of FIG. 2D, an exemplary counter unit 7U is similar to those of FIGS. 2A and 2B, except that the counter unit 7U has a pitch varying in a longitudinal direction. Other characteristics of the counter unit 7U of FIG. 2D may be similar or identical to those of the counter units of FIGS. 2A to 2C. In another example of FIG. 2E, an exemplary counter unit 7U is similar to that of FIG. 2A, except that the radius of winding of the counter unit 7U varies along its longitudinal direction. Other characteristics of the counter unit 7U of FIG. 2E may be similar or identical to those of the counter units of FIGS. 2A to 2D. In another example of FIG. 2F, an exemplary counter member 7 includes a pair of counter units 7U1, 7U2 disposed one over the other and enclosing therein different portions of the voice coil 5C, where the first counter unit 7U1 is similar to that of FIG. 2A, the second counter unit 7U2 is similar to that of FIG. 2C, and the like. Other characteristics of the counter units 7U1, 7U2 of FIG. 2F are similar or identical to those of the counter units of FIGS. 2A to 2E. It is to be understood that such a counter unit may also be arranged to have a shape, a size, an orientation, and an arrangement which may be a combination of any two or more of the above examples.

In another exemplary embodiment of this aspect of the invention, the counter member and/or its counter unit may be made of and/or include at least one electrically conductive article which may then be fabricated into various shapes, sizes, and/or orientations. In general, the counter unit may define a shape of a wire, a strip, a sheet, a tube, a coil, a mesh, an array of one or more of the above shapes, a combination of one or more of such shapes, and/or a combination of one or more of such shapes. It is to be understood that the counter member may define a symmetric (or an asymmetric) shape, may also be disposed in an arrangement symmetric (or asymmetric) to a preset portion or an entire portion of the voice coil and/or speaker magnet (if any), and so on. The counter member may include multiple counter units, where all of such counter units may define an identical or similar shape, where at least two of the counter units may define different shapes, and the like. In addition, such counter units may be disposed in an arrangement symmetric to each other, in another arrangement symmetric to a preset portion or an entire portion of the voice coil and/or speaker magnet (if any), and the like. FIGS. 2G to 2L are perspective views of exemplary counter members and/or their units enclosing therein at least a portion of the drive member according to the present invention.

In one example, the counter member may define a shape other than the coils of FIGS. 2A to 2F. As shown in FIG. 2G, an exemplary counter member 7 may include a single counter unit 7U forming a single loop disposed around the voice coil 5V. The dynamic signals may flow in the counter unit 7U in a direction opposite to another direction of such signals flowing in the voice coil 5V, thereby allowing the counter waves to cancel the desired portion of such harmful waves. In this example, amplitudes of the signals supplied to the counter unit 7U may be manipulated to accomplish the canceling of the desired portion of the harmful waves. The counter unit 7U may be disposed in any location along the longitudinal axis of the voice coil 5V so that the amplitudes of the counter waves may be controlled to achieve such desired canceling of the harmful waves. Other characteristics of the counter unit 7U of FIG. 2G are similar or identical to those of the counter units of FIGS. 2A to 2F.

In another example, the counter member may form at least one coil disposed around the voice coil and wound in a direction perpendicular to the longitudinal axis of the voice coil. As exemplified in FIG. 2H, an exemplary counter member 7 may include a single counter unit 7U wound around a preset elevation of the voice coil 5V by a preset number of turns. Because the counter unit 7U forms multiple layers of turns, such an unit 7U may generate the dynamic magnetic field stronger than that of FIG. 2G and may also emit the counter waves stronger than those of FIG. 2G when other factors being equal. As also exemplified in FIG. 2I, an exemplary counter member 7 may include a pair of counter units 7U1, 7U2 of FIG. 2H disposed one over the other along the longitudinal axis of the voice coil 5C and enclose different portions of the voice coil 5V therein. Other characteristics of the counter units 7U, 7U1, 7U2 of FIGS. 2H and 2I are similar or identical to those of the counter units of FIGS. 2A to 2G.

In another example, the counter member may form a tube of an arbitrary cross-section which may also enclose therein at least a substantial portion of the voice coil. In an exemplary embodiment of FIG. 2J, a counter member 7 may include a single counter unit 7U defining a circular cross-section and enclosing the voice coil 5V in its center in a symmetric arrangement such that the counter waves emitted by the counter unit 7U may cancel the desired portion of the harmful waves. To such an end, the signals may be supplied to the counter unit 7U in a direction opposite to that of the signals flowing in the voice coil 5V. It is appreciated that such a tube-shaped counter unit 7U may define other cross-sectional shapes, may define openings therethrough, and the like, as long as the counter waves may accomplish the desired canceling. Other characteristics of the counter unit 7U of FIG. 2J are similar or identical to those of the counter units of FIGS. 2A to 2I.

In another example, the counter member may define a mesh and enclose at least a substantial portion of the voice coil therein while maintaining a fluid communication therethrough. In an exemplary embodiment of FIG. 2K, a counter member 7 may have a single mesh which may be wrapped around the voice coil 5V in a symmetric arrangement, similar to that of conventional coaxial cables. Thus, the counter waves irradiated by the counter unit 7U may cancel the desired portion of the harmful waves as the dynamic signals may flow therein along a direction opposite to that of the voice coil 5V. Other characteristics of the counter unit 7U of FIG. 2K are similar or identical to those of the counter units of FIGS. 2A to 2J.

In another example, the counter member may consist of multiple conductive articles disposed in various arrangements each of which may preferably allow the articles to irradiate the counter waves capable of canceling such desired portion of the harmful waves. In an exemplary embodiment of FIG. 2L, multiple wire-shaped counter units 7U may be disposed around a circumference of the voice coil 5V at a preset interval so that the sum of the counter waves irradiated by such counter units 7U may cancel the desired portion of the harmful waves. It is to be understood that such a counter member 7 may include any desirable number of counter units 7U each of which may define the same or similar shape or at least two of which may define different shapes. In addition, the counter units 7U may be disposed in an arrangement symmetric (or asymmetric) to each other, in an arrangement symmetric (or asymmetric) to the voice coil 5V and/or speaker magnet (if any) of the drive member 5, and so on. Other characteristics of the counter unit 7U of FIG. 2L are similar or identical to those of the counter units of FIGS. 2A to 2K.

In another exemplary embodiment of this aspect of the invention, the counter members may be disposed in various arrangement and/or orientations with respect to the drive member of the system. FIGS. 2M to 2R represent schematic views of exemplary counter members each of which is placed in a preset relation with respect to the drive member according to the present invention. It is appreciated that all of these figures may be best interpreted as top (or bottom) views of various counter members and various cones wrapped by the voice coils. It is also appreciated that such counter members may enclose only portions or entire portions of the voice coils along the longitudinal direction of the cones (i.e., the direction perpendicular to the paper).

In one example, the counter member (or unit) may enclose therein at least a substantial portion of the cone. As exemplified in FIG. 2M, an exemplary counter member 7 may include a single counter unit 7U (or multiple counter units 7U along the longitudinal direction) which may be coupled to a coupler 7C which may define a circular cross-section and enclose the cone 5C near its center in a symmetric arrangement. Therefore, the counter waves irradiated from the counter unit 7U may be automatically aligned with the harmful waves irradiated by the voice coil 5V wrapped around the cone 5C. Further characteristics of the counter unit 7U of FIG. 2M are similar or identical to those of the counter units of FIGS. 2A to 2L. In another example of FIG. 2N, an exemplary counter member 7 is similar to that of FIG. 2M, except that a coupler 7C may define an oval cross-section. Accordingly, the counter unit 7U may enclose the cone 5C near its center in a symmetric arrangement, while facing different portions of the voice coil 5V at different distances. Accordingly, such a counter unit 7U may emit the counter waves with different amplitudes in different directions, although such counter waves may also be arranged to have uniform amplitudes therearound by manipulating the configuration of the counter unit 7U, e.g., by including more conductive articles in those portions disposed farther away from the cone 5C and including less conductive articles in those portions closer to the cone 5C. In the alternative, amplitudes of the dynamic signals supplied to different portions of the counter unit 7U may further be controlled to manipulate the counter unit 7U to irradiate such counter waves defining desirable distribution of their amplitudes. In another alternative, the counter unit 7U may also enclose the cone 5C in an off-center location capable of manipulating the distribution pattern of the amplitudes of the counter waves. Other characteristics of the counter unit 7U of FIG. 2N are similar or identical to those of the counter units of FIGS. 2A to 2M. In another example of FIG. 2O, an exemplary counter member 7 is similar to those of FIGS. 2M and 2N, except that a coupler 7C may not have any symmetric cross-section and, thus, the counter unit 7U may be disposed in an asymmetric arrangement. As described above, however, the configuration of the counter unit 7U, arrangement of such an unit 7U, and directions of the signals may also be manipulated to generate such counter waves of suitable amplitude distribution patterns. Other characteristics of the counter unit 7U of FIG. 2O are similar or identical to those of the counter units of FIGS. 2A to 2N.

In another example, the counter member (or unit) may be disposed beside the cone while not enclosing a substantial portion of the cone therein. As exemplified in FIG. 2P, a curvilinear coupler 7C as well as a counter unit 7U wrapped therearound may be disposed on one side of the cone 5C in a symmetric arrangement. Because of such an off-center disposition, it may not be feasible to cancel at least a substantial portion of the harmful waves by the counter waves generated by the counter unit 7U. Accordingly, such a disposition may be employed when it is desirable to cancel only a portion of the harmful waves in a preset area around the cone 5C. In the alternative, such counter members 7 may be provided in multiple numbers around multiple sources and/or cones 5C so that the sum of the counter waves irradiated by such counter units 7U may also cancel the desired portion of the harmful waves. It is appreciated, however, that the counter unit 7U of FIG. 2P may form a symmetry between its top and bottom portions such that the counter waves may also define similar symmetric properties. As also exemplified in FIG. 2Q, an asymmetric curvilinear coupler 7C may be similarly disposed away from the cone 7C and a counter unit 7U may be wrapped therearound so as to generate the counter waves which may be misaligned with such harmful waves or, may be manipulated to be aligned with such harmful waves by any of the aforementioned means. Other characteristics of the counter units 7U of FIGS. 2P and 2Q are similar or identical to those of such counter units of FIGS. 2A to 2P.

In another example, the counter member may include multiple counter units disposed around or alongside the cone in various enclosing or non-enclosing arrangements. As exemplified in FIG. 2R, an exemplary counter member 7 may have a pair of identical counter units 7U1, 7U2 each of which may define an oval cross-section. The counter units 7U1, 7U2 may then be disposed in opposite sides of the cone 5C at an equal distance in a symmetric arrangement so that the counter waves generated by such counter units 7U1, 7U2 may further be at least partially aligned with such harmful waves. Other characteristics of the counter unit 7U of FIG. 2R are similar or identical to those of the counter units of FIGS. 2A to 2Q.

Figure 2A:
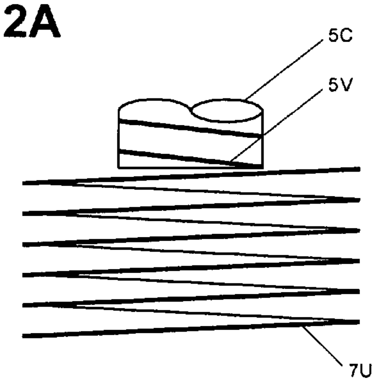
FIGS. 2A to 2F are schematic views of exemplary counter members which are wound as coils and disposed around the drive member according to the present invention.
Figure 2B:
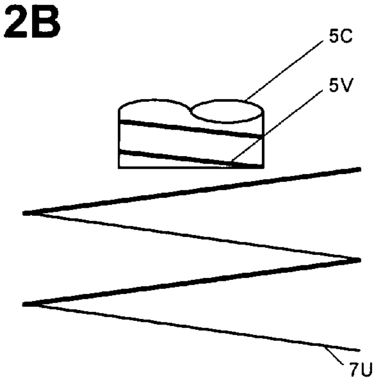
Figure 2C:
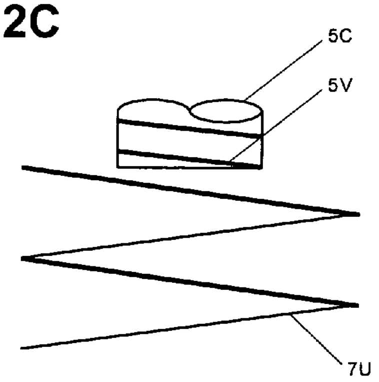
Figure 2D:
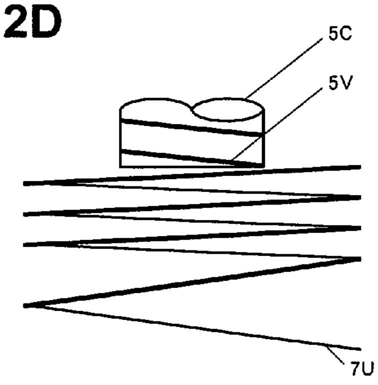
Figure 2E:
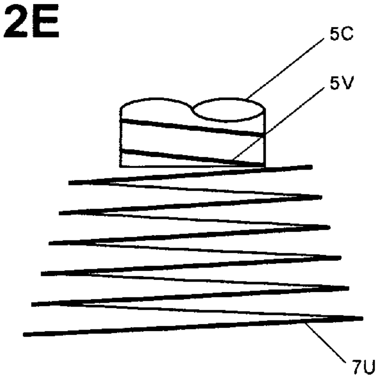
Figure 2F:
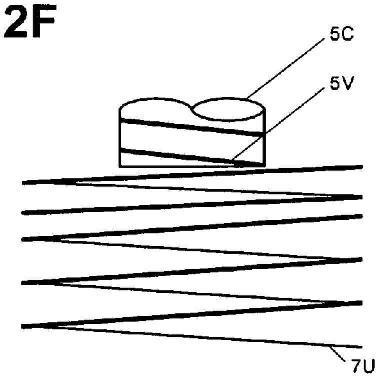
Figure 2G:
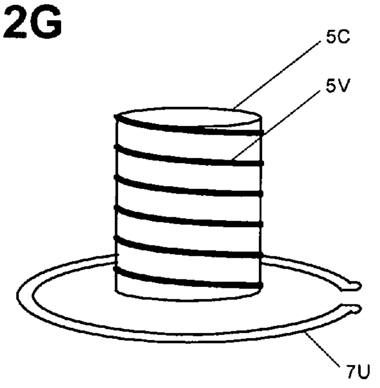
FIGS. 2G to 2L are perspective views of exemplary counter members enclosing therein at least a portion of the drive member according to the present invention.
Figure 2J:
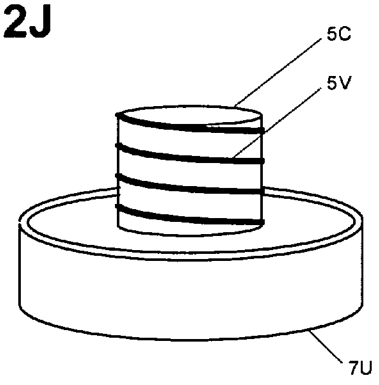
Figure 2H:
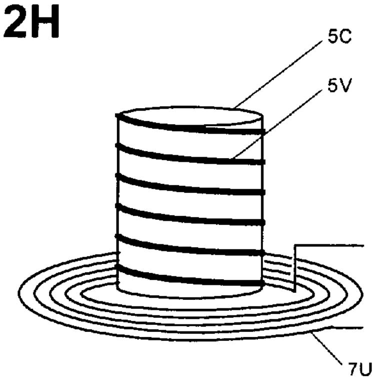
Figure 2K:
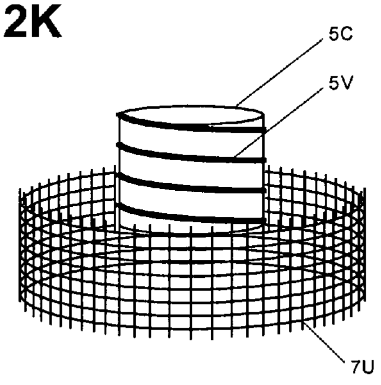
Figure 2I:
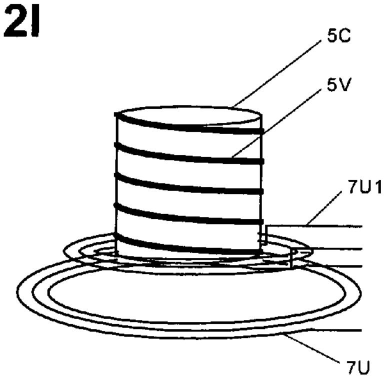
Figure 2L:
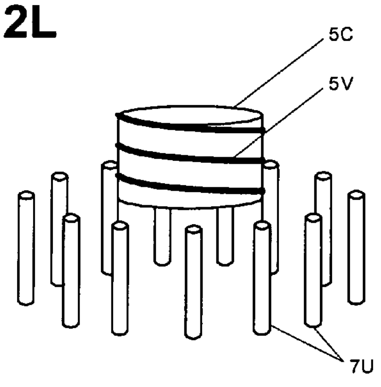
Figure 2M:
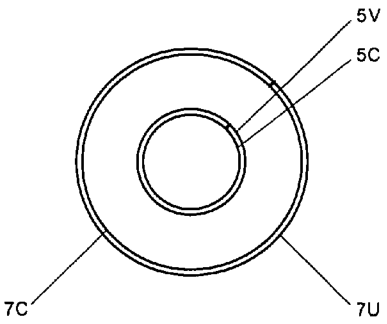
FIGS. 2M to 2R are schematic views of exemplary counter members each of which is placed in a preset relation with respect to the drive member according to the present invention.
Figure 2P:
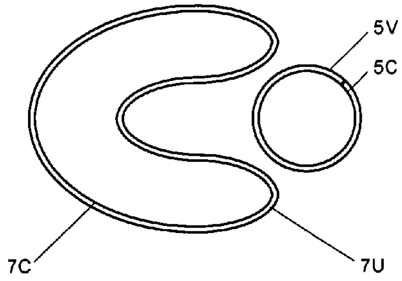
Figure 2N:
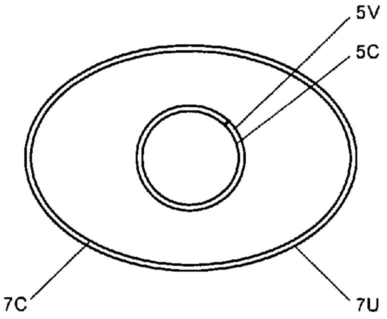
Figure 2Q:
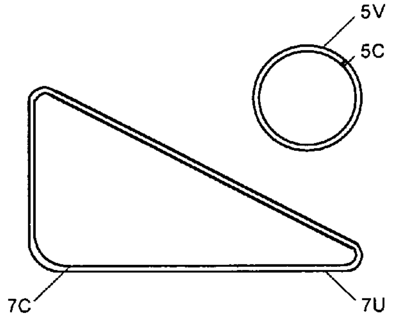
Figure 2O:
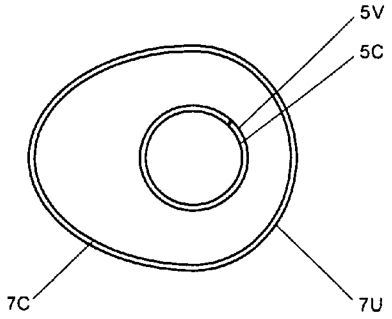
Figure 2R:
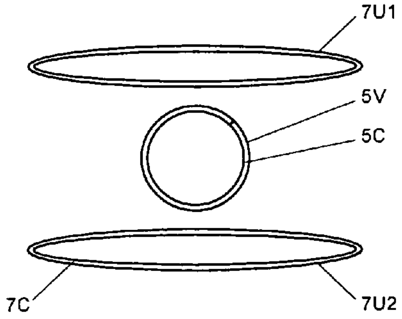

In another exemplary embodiment of this aspect of the invention, the counter members may be incorporated in other shapes, sizes, and orientations with respect to the drive member of the system. FIGS. 2S to 2X represent schematic views of exemplary counter members each of which is disposed in another preset relation to the drive member according to the present invention. It is appreciated that FIGS. 2S to 2V are to be interpreted as top (or bottom) views of various counter members and cones wrapped by such voice coils and that FIGS. 2W and 2X are to be interpreted as side views of various counter members and cones wrapped thereby. It is also appreciated that such counter members may include multiple counter units disposed in various arrangements and orientations, where such counter units may define identical, similar or different shapes and/or sizes and where such counter units may be disposed symmetrically (or asymmetrically) to each other, symmetrically (or asymmetrically) to the cone and/or speaker magnet (if any).

Figure 2S:
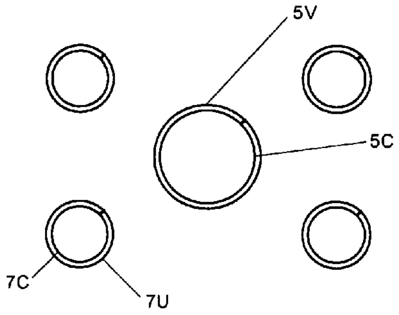
FIGS. 2S to 2X are schematic views of exemplary counter members each of which is disposed in another preset relation with respect to the drive member according to the present invention.

In one example of FIG. 2S, an exemplary counter member 7 may include four counter units 7U defining identical shapes and sizes and coupled to four couplers 7C which may in turn be disposed in four corners of a square or rectangle in a center of which the cone 5C may be disposed. Therefore, the counter waves emitted by such counter units 7U may be manipulated to have desirable symmetric propagation characteristics capable of canceling the desired portion of such harmful waves. As also exemplified in FIG. 2T, an exemplary counter member 7 may also include three counter units 7U having identical shapes and sizes and coupled to three couplers 7C which may be disposed in three vertices of an arbitrary. Therefore, the counter waves emitted by the counter units 7U may be manipulated to define preset propagation characteristics for canceling the desired portion of the harmful waves. As further exemplified in FIG. 2U, an exemplary counter member 7 may instead include three counter units 7U disposed on only one side of the cone 5C. Such an arrangement may be utilized in various ways as described in conjunction with those of FIGS. 2P and 2Q. Other characteristics of the counter unit 7U of FIGS. 2S to 2U are similar or identical to those of the counter units of FIGS. 2A to 2R.

Figure 2V:
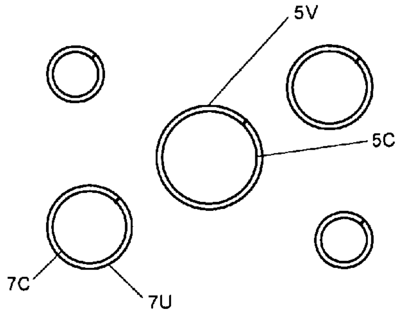
Figure 2T:
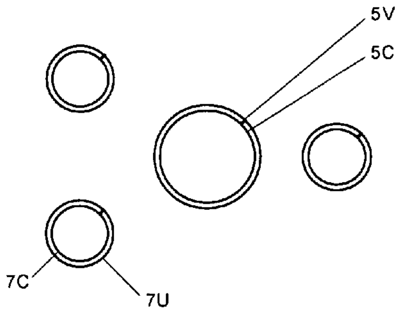
Figure 2W:
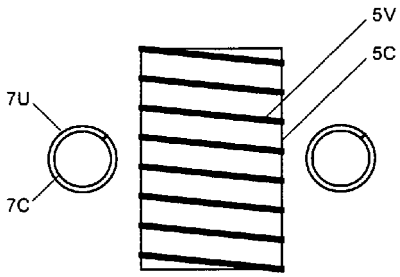
Figure 2U:
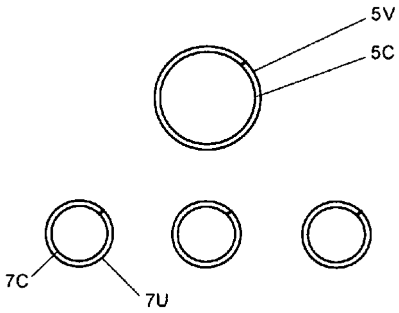
Figure 2X:
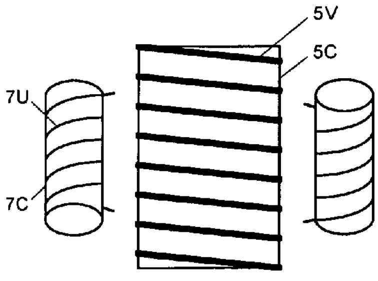

In another example of FIG. 2V, an exemplary counter member 7 may include four counter units 7U having different shapes and sizes and coupled to four couplers 7C which may in turn be disposed in four corners of a square or rectangle in a center of which the cone 5C may be disposed. Thus, the counter waves emitted by the counter units 7U may also be manipulated to have desirable propagation characteristics for canceling the desired portion of the harmful waves. Further characteristics of the counter unit 7U of FIG. 2V are similar or identical to those of the counter units of FIGS. 2A to 2U.

In another example of FIG. 2W, an exemplary counter member 7 may include a pair of counter units 7U which may wound around a pair of couplers 7C which may be disposed on opposite sides of the cone 5C and which may extend along a direction perpendicular to the longitudinal axis of the cone 5C. In order to align the counter waves irradiated thereby, such counter units 7U may be arranged to define various configurations and/or may be supplied with such external currents or source signals in various directions as well as described heretofore and hereinafter. In another example of FIG. 2X, an exemplary counter member 7 may have another pair of counter units 7U which may be wound around a pair of couplers which may be disposed on opposite sides of the cone 5C at angles which may not 90°. Similar to those of FIG. 2W, such counter units may also be arranged to emit the counter waves for canceling the desired portion of the harmful waves, e.g., by manipulating their configurations and dispositions, controlling the amplitudes and/or directions of the dynamic signals, and the like. Further characteristics of the counter unit 7U shown in FIGS. 2W and 2X may be similar or identical to those of the counter units of FIGS. 2A to 2V.

Configurational and/or operational variations and/or modifications of the counter members and units exemplified in FIGS. 2A through 2X also fall within the scope of this invention.

As described above, such counter members and counter units may be used interchangeably within the scope of the present invention. Accordingly, all of the foregoing variations and modifications described in conjunction with FIG. 1B may be applied to each counter unit and/or to assemblies of the counter units of FIGS. 2A to 2X unless otherwise specified.

As described above, the counter unit may be arranged to enclose therein at least a portion of the drive member or, in the alternative, to be disposed alongside the drive member without enclosing any portion of the drive member. When the counter member may include a single counter unit, such an unit may enclose therein such a portion of the drive member or may be disposed side by side with the drive member. When the counter member may include multiple counter units, such units may then be disposed around and enclose therewithin such a portion of the drive member or, in the alternative, may be disposed alongside the drive member in a preset pattern.

Similar to the counter member, a single counter unit may be disposed in a preset relation to the drive member and also generate the counter waves for canceling the desired portion of such harmful waves. Alternatively, the single counter unit may be supplied with the dynamic signals for generating the counter waves capable of canceling the desired portion of the harmful waves. When the counter member includes multiple counter units, at least two or all of such units may be disposed in a preset relation to a single or multiple wave sources of the drive member for canceling the desired portion of the harmful waves by the local or global canceling. In the alternative, at least two or all of the counter units may be supplied with the dynamic signals of the same or similar amplitudes and/or flowing in the same or similar directions therefor. In another alternative and depending upon detailed configurations, arrangements, and/or orientations thereof, at least two or all of the counter units may be supplied with the dynamic signals defining different amplitudes and/or flowing in different directions therefor.

In addition and as exemplified in some of the above figures, the counter member may include a single symmetric counter unit or may include a single symmetric or asymmetric counter unit disposed around or alongside the drive member in a symmetric arrangement. Alternatively, the counter member may include a single asymmetric unit or may instead include a single symmetric or asymmetric counter unit disposed around or alongside the drive member in an asymmetric arrangement. When the counter member may have multiple counter units, such units may be symmetric or asymmetric or, alternatively, the counter units may be disposed around or alongside the drive member in a symmetric arrangement. The counter member may instead include multiple asymmetric units or, in the alternative, may include multiple symmetric or asymmetric counter units disposed around or alongside the drive member in an asymmetric arrangement.

Similar to the case of multiple counter members as described above, multiple counter units of a single counter member may have an identical configuration or similar configurations, may be disposed in a symmetric or asymmetric arrangement, and the like. In particular, such counter units may have the same shape such as, e.g., wires, strips, sheets, tubes, coils, meshes, and so on. At least one of the counter units may define an assembly, a combination, and/or mixture of one or more of such shapes. Such counter units may further be disposed at the same distance from the user and/or drive member or at least one of such counter units may be disposed closer to or farther away from the user and/or drive member. In addition, each of such counter units may generate the counter waves defining the same or similar amplitudes and/or propagation directions or, alternatively, at least one of such counter units may generate the counter waves defining stronger or weaker amplitudes than the rest thereof. As described above, each counter unit may be disposed around one of multiple wave sources of the drive member and perform the local canceling. In the alternative, at least two of the counter units may be arranged to irradiate the counter waves the sum of which may be capable of canceling the desired portion of the harmful waves and perform the global canceling.

As described in conjunction with FIGS. 1B and 2A to 2X, various counter members and units of the present invention may define various configurations, may be disposed in various arrangements or orientations, may be supplied with the external currents or at least portions of the signals with various amplitudes and/or directions, may be disposed in various distances from the user and wave sources of the drive member, and the like. The principal requirement of all of the above criteria, however, is to ensure that the counter waves irradiated by a single or multiple counter members and/or units may be capable of canceling the desired portion of the harmful waves. Accordingly, such counter members and units are to be preferably constructed according to the above criteria while satisfying the above requirement. In other words, such counter members and counter units may be constructed in various embodiments as long as such requirement is met.

As described in detail in the co-pending Applications and briefly described above, it is widely believed that various EM waves in the range of infrared rays, more particularly, far-infrared rays are beneficial to humans. Therefore, the EMC speaker system may be tailored to selectively irradiate such beneficial IR rays, e.g., by selectively canceling the low-frequency portions of the harmful waves by the counter members or counter units, by emitting the IR rays by the counter members or counter units while performing the selective or overall cancellation of the harmful waves, and the like.

Other configurational and/or operational characteristics of the counter units may be identical or similar to those of the counter members as described above. In addition, other configurational and/or operational characteristics of the counter members and units may be similar or identical to those of the co-pending Applications.

In another aspect of the present invention, such counter members and/or counter units may be incorporated into various portions of the EMC speaker system of the present invention. FIGS. 3A to 3L are cross-sectional views of the exemplary speaker system of FIG. 1B incorporating various counter members and units in various locations thereof according to the present invention. It is appreciated in these figures that various counter members and/or units are depicted by multiple dots, that such dots may denote cross-sections of coils, but that such dots may also describe other shapes such as, e.g., wires, strips, tubes, sheets, meshes, arrays thereof, combinations thereof, mixtures thereof, and the like. It is also appreciated that each figure only include a single quadrant of an entire cross-section of the EMC speaker and that such dots may depict a specific disposition of the counter members or units only in that location or may describe a symmetric disposition of the counter members or units about an axis of symmetry which may coincide with a center longitudinal axis of the system, with an off-center longitudinal axis thereof, with an axis perpendicular to such longitudinal axes, and the like.

Figure 3A:
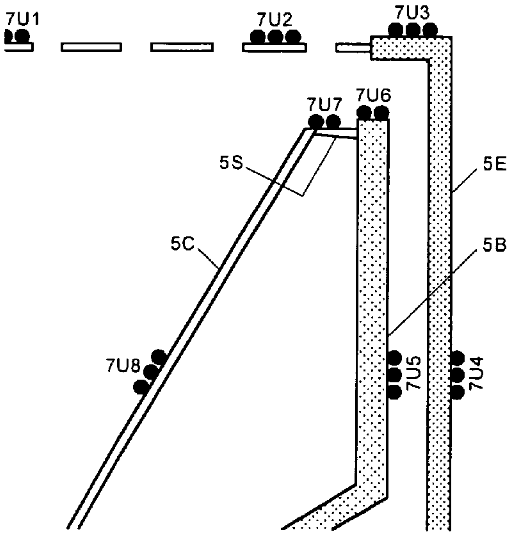
FIGS. 3A to 3L are cross-sectional views of the exemplary speaker system of FIG. 1B which incorporates the counter member in various locations thereof according to the present invention.

In one exemplary embodiment of this aspect of the invention and as exemplified in FIG. 3A, an exemplary counter unit (or member) may be disposed in various locations of an upper quadrant of the cross-section of the EMC system. For example, such a counter unit may be disposed on an exterior of the case member 5E and on a top center portion (7U1), on a top middle portion (7U2), on a top edge portion (7U3), on its side (7U4), and so on. A counter unit may also be disposed on an exterior of the bracket 5B and on its side (7U5) or on a top edge (7U6), or may be disposed on top of the suspension 5N (7U7) or on top of the cone 5C (7U8).

Figure 3C:
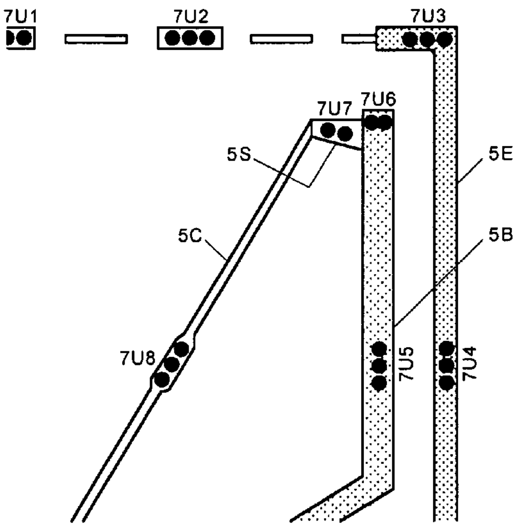
Figure 3B:
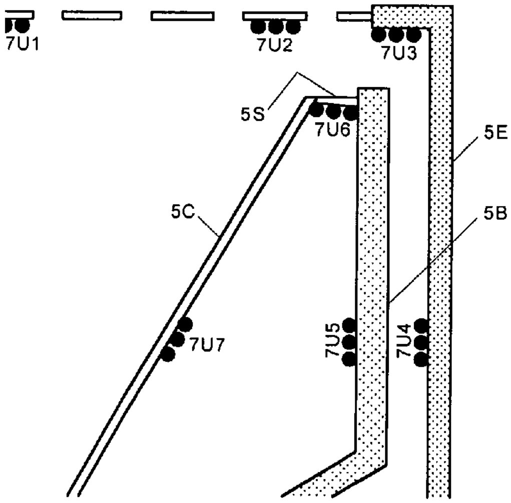

In another exemplary embodiment of this aspect of the invention and as exemplified in FIG. 3B, an exemplary counter unit (or member) may be disposed in various locations of the upper quadrant of the cross-section of the EMC system. For example, a counter unit may be incorporated on an interior of the case member 5E and below a top center portion (7U1), below a top middle portion (7U2), below a top edge portion (7U3) or on its side (7U4). A counter unit may instead be disposed on an interior of the bracket 5B and on its side (7U5), may also be disposed below the suspension 5N (7U6) or below the cone 5C (7U7).

In another exemplary embodiment of this aspect of the invention and as exemplified in FIG. 3C, an exemplary counter unit (or member) may be embedded in various locations of the upper quadrant of the cross-section of the EMC system. For example, a counter unit may be embedded into the case member 5E and in a top center portion (7U1), in a top middle portion (7U2), in a top edge portion (7U3) or in a side (7U4). A counter unit may be embedded into the bracket 5B and on its side (7U5) or on its top (7U6), may be embedded into the suspension 5N (7U7) or into the cone 5C (7U8).

Figure 3D:
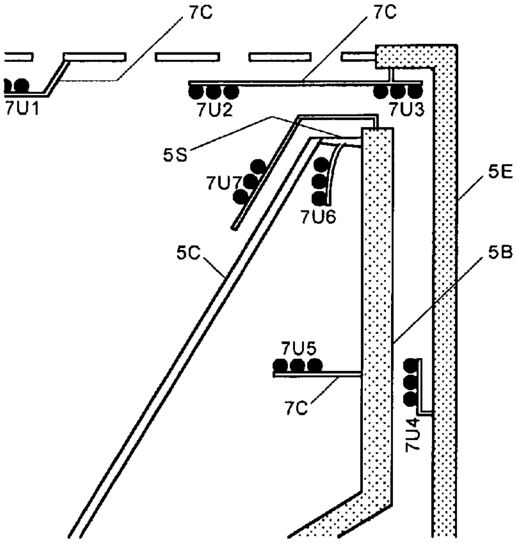

In another exemplary embodiment of this aspect of the invention and as exemplified in FIG. 3D, an exemplary counter unit (or member) may be disposed in various locations of the upper quadrant of the cross-section of the EMC system by various couplers releasably or fixedly coupling with various portions of such EMC systems. For example, a coupler 7C may be releasably or fixedly coupled to the case member 5E and receive thereonto a counter unit which may then be disposed on an interior (or exterior) of the case member 5E and below (or over) a top center portion (7U1), below (or over) a top middle portion (7U2), below (or over) a top edge portion (7U3) or over a side (7U4). A coupler 7C may similarly couple with the bracket 5B and receive thereonto a counter unit which may be disposed into (or out of an interior (or exterior) of the bracket 5B and over a side (7U5) or over a top edge (7U6). A coupler 7C may be coupled to the suspension 5N and receive thereonto another counter unit which may then be disposed on into interior (or exterior) thereof (7U7) as well.

Figure 3E:
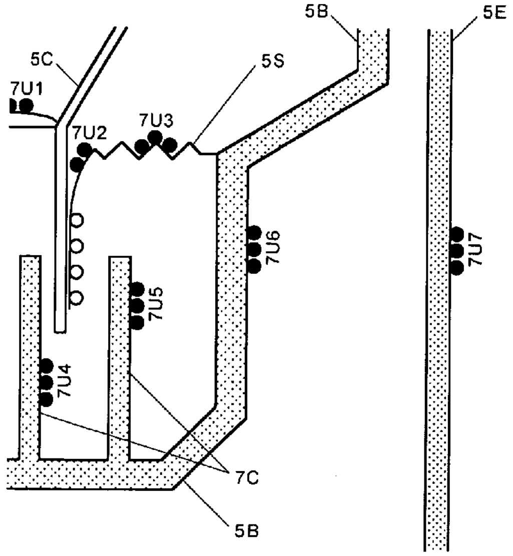

In another exemplary embodiment of this aspect of the invention and as exemplified in FIG. 3E, an exemplary counter unit (or member) may be disposed in various locations of a middle quadrant of the cross-section of the EMC system. For example, a counter unit may be disposed on an exterior of the dust cap 5D (7U1), on an exterior of the spider 5S and near the cone 5C (7U2) or near the bracket 5B (7U3), on an exterior of the coupler 7C (7U4 and 7U5) which may be disposed inside and outside of the narrow end of the cone 5C, respectively, on an exterior and on a side of the bracket 5B (7U6) or case member 5E (7U7), and the like.

Figure 3G:
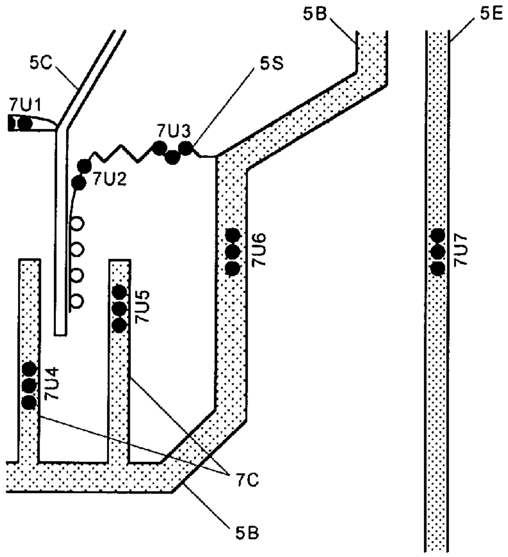
Figure 3F:
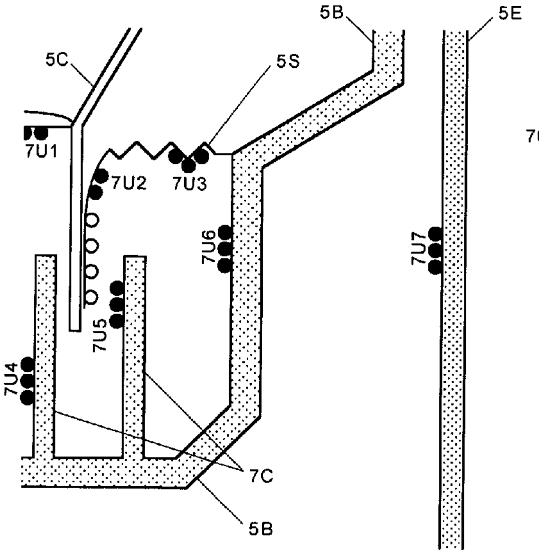

In another exemplary embodiment of this aspect of the invention and as exemplified in FIG. 3F, an exemplary counter unit (or member) may be disposed in various locations of the middle quadrant of the cross-section of the EMC system. For example, a counter unit may be disposed below an interior of the dust cap 5D (7U1), below an interior of the spider 5S and near the cone 5C (7U2) or near the bracket 5B (7U3), on an interior of the coupler 7C (7U4 and 7U5) which may be disposed inside and outside the narrower end of the cone 5C, respectively, on an interior and on a side of the bracket 5B (7U6) or case member 5E (7U7).

In another exemplary embodiment of this aspect of the invention and as exemplified in FIG. 3G, an exemplary counter unit (or member) may be embedded in various locations of the middle quadrant of the cross-section of the EMC system. For example, a counter unit may be embedded into the dust cap 5D (7U1), embedded into the spider 5S and near the cone 5C (7U2) or near the bracket 5B (7U3), embedded into the coupler 7C (7U4 and 7U5) which may be disposed inside and outside the narrower end of the cone 5C, respectively, embedded inside the bracket 5B (7U6) or inside the case member 5E (7U7), and the like.

Figure 3H:
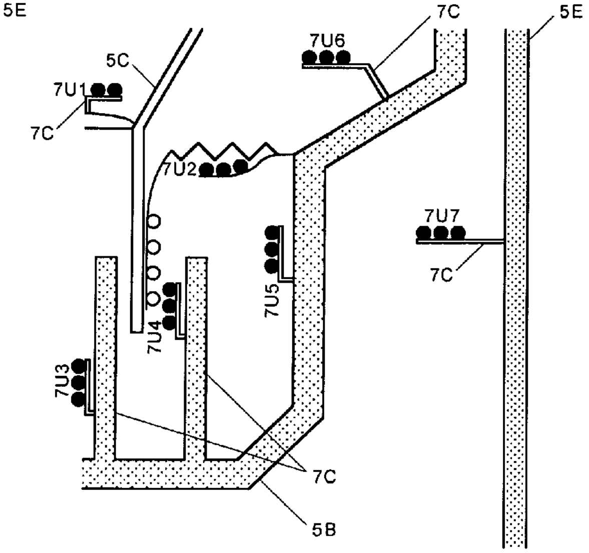
Figure 3I:
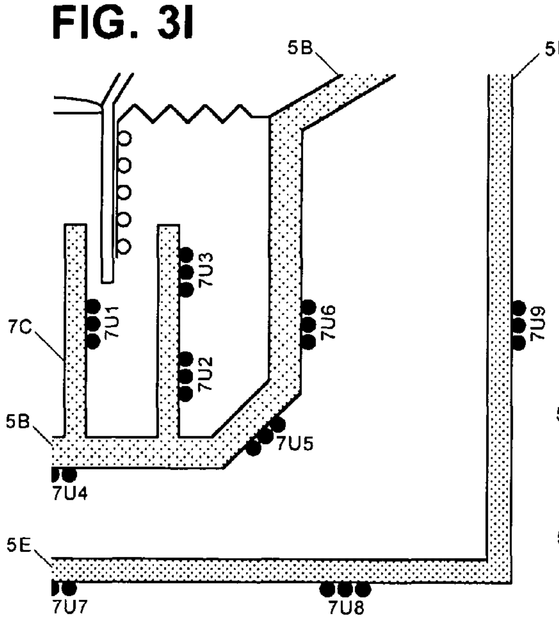

In another exemplary embodiment of this aspect of the invention and as exemplified in FIG. 3H, an exemplary counter unit (or member) may be disposed in various locations of the middle quadrant of the cross-section of the EMC system by various couplers releasably or fixedly coupling with various portions of such EMC systems. For example, a coupler 7C may be releasably or fixedly coupled to the dust cap 5D and receive thereon a counter unit (7U1) which may then be disposed over an interior (or exterior) of the cone 5C. A coupler 7C may similarly couple with the spider 5S and receive thereon a counter unit which may be disposed respectively over an interior (or exterior) of the spider 5S (7U2). A counter unit may also be received on the coupler 7C (7U3 and 7U4) which may be disposed inside and outside the narrower end of the cone 5C, respectively. In addition, the coupler 7C may couple to an interior (or exterior) of the bracket 5B and below the spider 5S (7U5) or above the spider 5S (7U6), to an interior (or exterior) of the case member 5E (7U7).

In another exemplary embodiment of this aspect of the invention and as exemplified in FIG. 31, an exemplary counter unit (or member) may be disposed in various locations of a lower quadrant of the cross-section of the EMC system. For example, a counter unit may be disposed on an exterior of the coupler 7C (7U1, 7U2, 7U3) which may be disposed inside and outside of the narrower end of the cone 5C, respectively. A counter unit may be disposed on an exterior of the bracket 5B and below a bottom center portion (7U4), below a bottom edge (7U5), and on a side (7U6). A counter unit may be disposed on an exterior of the case member 5E and below a bottom center portion (7U7), on a bottom edge (7U8) or on a side (7U9).

Figure 3K:
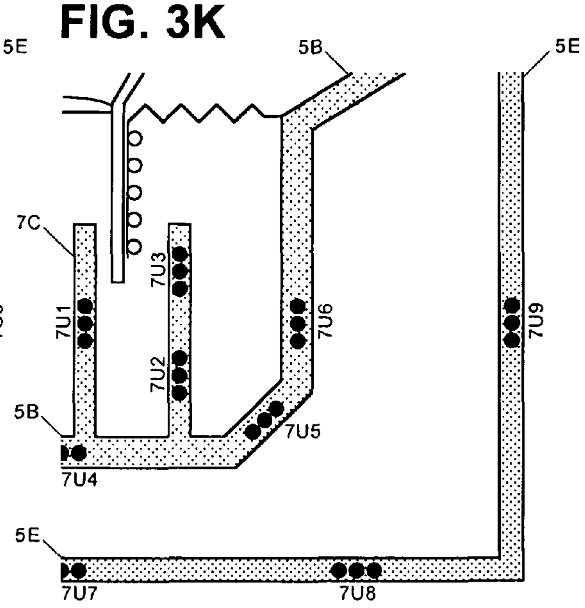
Figure 3J:
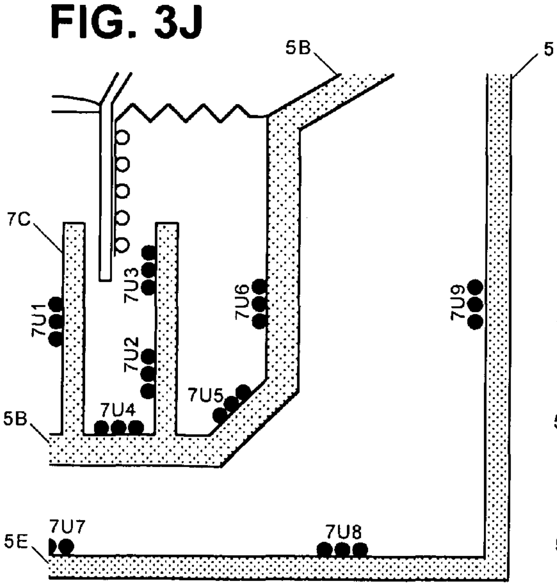

In another exemplary embodiment of this aspect of the invention and as exemplified in FIG. 3J, an exemplary counter unit (or member) may be disposed in various locations of a lower quadrant of the cross-section of the EMC system. For example, a counter unit may be disposed on an interior of the coupler 7C (7U1, 7U2, 7U3) which may be disposed inside and outside the narrower end of the cone 5C, respectively. A counter unit may be disposed on an interior of the bracket 5B and over a bottom center portion (7U4), over a bottom edge (7U5), and on a side (7U6). A counter unit may also be disposed on an interior of the case member 5E and on a bottom center portion (7U7), on a bottom edge (7U8), and on an inner side (7U9).

In another exemplary embodiment of this aspect of the invention and as exemplified in FIG. 3K, an exemplary counter unit (or member) may be embedded in various locations of the lower quadrant of the cross-section of the EMC system. For example, such a counter unit may be embedded into the coupler 7C (7U1, 7U2, 7U3) which may then be embedded into the coupler 7C which may be disposed inside and outside the narrower end of the cone 5C, respectively, may be embedded into the bracket 5B and in a bottom center portion (7U4), in a bottom edge (7U5) or in a side (7U6), may be embedded into the case member 5E and in a bottom center portion (7U7), in a bottom peripheral portion (7U8) or on a side (7U9).

Figure 3L:
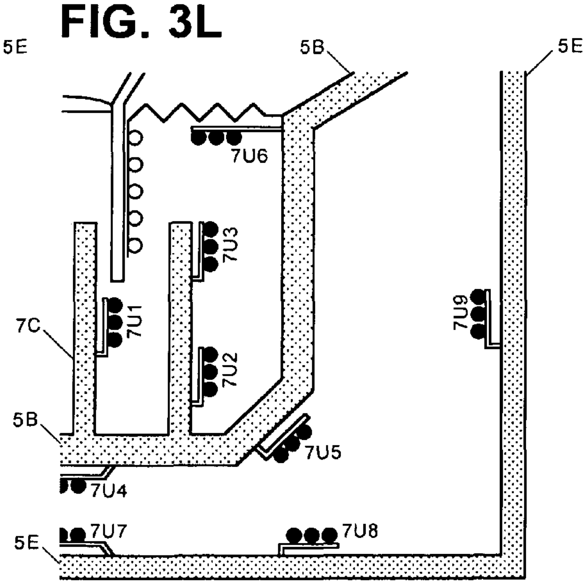

In another exemplary embodiment of this aspect of the invention and as exemplified in FIG. 3L, an exemplary counter unit (or member) may be disposed in various locations of the lower quadrant of the cross-section of the EMC system by various couplers releasably or fixedly coupling with various portions of such EMC systems. For example, a coupler 7C (7U1, 7U2, 7U3) may also be releasably or fixedly coupled inside or outside the narrower end of the cone 5C, respectively. A coupler 7C may be coupled to the bracket 5B and receive thereon a counter unit below (or over) a bottom center portion (7U4), below (or over) a bottom edge (7U5), and on a side (7U6). A coupler 7C may also couple with the case member 5E and receive thereon a counter unit which may also be disposed over (or below) a bottom center portion (7U7), over (or below) a bottom peripheral portion (7U8) or on a side (7U9).

Configurational and/or operational variations and/or modifications of the counter members and units exemplified in FIGS. 3A through 3L also fall within the scope of this invention.

As described above, multiple dots of such figures may represent various counter members or counter units each of which may define one or more of the above shapes such as, e.g., wires, strips, tubes, sheets, coils, meshes, arrays thereof, combinations thereof, mixtures thereof, and the like. It is also appreciated that each set of multiple dots of such figures may represent a single counter member or unit, that each set of multiple dots thereof may represent multiple counter members or units each of which may define the identical or similar shape or at least two of which may define different shapes, that such counter members or units may be disposed in the same, similar or different arrangements or orientations, that such counter members or units may be supplied with the external currents or signals having the same, similar or different amplitudes and flowing therethrough along the identical, similar or different directions.

In addition, such a counter member or unit denoted by each set of such dots may be disposed in the specific location denoted by the dots such that, e.g., the counter unit 7U2 of FIG. 3A may denote the conductive article having a finite size and disposed on the specific area of the exterior of the case member. Alternatively, the counter member or unit denoted by each set of such dots may instead be disposed in more than one quadrant of the cross-section of the system in a symmetric or asymmetric arrangement while revolving around a preset portion of the system or its drive member about a preset axis of revolution. For example, the counter unit 7U2 of FIG. 3A may describe a coil of such an article which may symmetrically or asymmetrically wind the top exterior of the case member around the axis of revolution which also corresponds the longitudinal axis of such a system. Thus, such an unit 7U2 may encompass the top right and top left quadrants. Alternatively, such a counter unit 7U2 of FIG. 3A may instead be viewed as another coil of such an article which may symmetrically or asymmetrically wind the right side of the system around the axis of revolution which corresponds to a transverse or lateral axis of the system which in turn intersects the longitudinal axis at angles not equal to 0° or 180°.

Moreover, the counter member or unit represented by each set of the dots may extend or wind in a direction which may or may not coincide with a direction in which such dots are disposed in such figures. For example, the counter unit 7U2 of FIG. 3A may correspond to any of the coils of FIGS. 2A to 2F which are wound from top to bottom or vice versa and, therefore, extend in a direction opposite to a direction of such dots are positioned in the figure. Alternatively, such an unit 7U2 of FIG. 3A may correspond to the coil of FIG. 2H which may be wound from the center portion to the periphery of the top portion of the case member or vice versa and, therefore, extends in the same direction as the dots are positioned in the figure. In another alternative, the counter unit 7U2 of FIG. 3A may correspond to the array of multiple loops of FIG. 2G which may be stacked from top to bottom (or vice versa) or from the center portion to the periphery of the top portion of the case member (or vice versa).

As described hereinabove, the counter members or counter units may be disposed by various means. In one example, such counter members or units may be disposed in preset portions of such a system by being disposed onto various couplers which may be releasably or fixedly coupled to preset portions of the system. In another example, such counter members or units may be directly coupled to the preset portions of the system such as, e.g., on the exterior of, on the interior of or inside the case member, bracket, suspension, cone, spider, magnet, and the like. In another example, such counter members or units may be disposed freely in a gap space formed between various portions of such a system without being aided by the couplers. As long as such counter members or units may irradiate such counter waves capable of canceling the desired portion of the harmful waves, detailed coupling means for the counter members or units may not be material within the scope of this invention.

In another aspect of the present invention, an EMC speaker system may include at least one of at least one electric shield and at least one magnetic shield. In one example, the electric shield (to be referred to as the "ES" hereinafter) and/or magnetic shield (to be referred to as the "MS" hereinafter) may be incorporated into, on, over or below various portions of the system. In another example, such an ES and/or MS may be incorporated as above and also used in conjunction with the above counter member or unit. In general, the ES may be made of and/or include at least one electrically conductive material such that the electric waves of the harmful waves may be absorbed thereinto and rerouted therealong. When desirable, the ES may also be grounded so that the absorbed and rerouted electric waves may be eliminated therefrom. The MS may be made of and/or include at least one magnetically permeable path member such that magnetic waves of the harmful waves may be absorbed thereinto and rerouted therealong. When desirable, such an MS may include a magnet member which may be magnetically coupled to the path member and terminate the absorbed and rerouted magnetic waves in one of magnetic poles of the magnet member. The MS may further include a shunt member which may be also magnetically permeable and shield its magnet member, thereby confining a magnetic field from the magnet member closer thereto. Further details of such ES and MS have been provided in the co-pending Applications, where such details may be modified so that various heating elements of the co-pending Applications may be replaced by the counter members and/or units of this invention and such ES and/or MS may be incorporated into the counter members and/or units in this invention as such ES and/or MS have been incorporated into various heating elements of the co-pending Applications. It is to be understood that such ES and/or MS may also be incorporated into various portions of the EMC speaker system as the counter members and/or units are incorporated into such portions of the EMC speaker system.

As described above, the EMC speaker system of this invention may be provided with multiple defense mechanisms against the harmful waves generated by various sources of the system such as, e.g., the drive member and other wiring of the system. In one example, the counter member may be incorporated into various portions of such a system as described above. Accordingly, a single or multiple counter members and/or counter units may be disposed in a two- or three-dimensional paired or concentric arrangement in which the counter members and/or units may be disposed alongside the source of the system or may enclose at least a portion of the wave source, respectively. In another example, the ES and/or MS may be incorporated into various portions of such a system and shield the electric and/or magnetic waves of the harmful waves, respectively, where dispositions of the shields have been described in the co-pending Application. In another example, not only the counter member (and/or counter unit) but also at least one of the shields may be implemented into the system such that the counter member (or unit) may cancel such a desired portion of the harmful waves and that the ES and/or MS may absorb and reroute the rest of the harmful waves.

Configurational and/or operational variations and/or modifications of the EMC speaker systems also fall within the scope of this invention.

Such a system may be an earphone including at least one speaker with the counter member or electric and/or magnetic shields, a headphone including such a speaker, an audio and/or video system including such a speaker, another electric device including such a speaker, a speak of various electric devices, a microphone, an assembly of the speaker and microphone, and the like. Such a system may also be at least two same or different speakers enclosed in a single case member, at least two same or different speakers separately enclosed inside different case members, a pair of earphones, a pair of headphones, an assembly having at least one speaker and at least one microphone, and the like.

Such a relation may relate to a shape and/or a size of the counter member (or counter unit), a shape and/or a size of the voice coil, a shape and/or size of the magnet (if any), an orientation of the voice coil, counter member (or unit), and/or magnet (if any), an arrangement of the counter member (or unit), voice coil, and/or magnet (if any), amplitudes of the signals flowing in the counter member (or unit) and/or voice coil, directions of the currents and/or signals flowing in the counter member (or unit) and/or voice coil, and the like. The counter member and/or counter unit may also define a curvilinear shape of a wire, an array thereof, a strip, an array thereof, a sheet, an array thereof, a tube, an array thereof, a coil, an array thereof, a mesh, an array thereof, a combination of two or more of the above shapes, a mixture of two or more of such shapes, and the like, where the array may define a shape of a bundle, a braid, a coil, a mesh, and the like. Such a shape and/or array may further define a two-dimensional shape or a three-dimensional shape.

At least two portions of the counter member and/or counter unit may define the same or similar shapes of different sizes. At least two portions of the counter member and/or counter unit may have different shapes of similar or different sizes. At least two of the counter units may define the same or similar shapes of different sizes. At least two of the counter units may define different shapes of the same, similar or different sizes. The counter unit and voice coil may define the same or similar shapes of different sizes or, in the alternative, the counter unit and voice coil may define different shapes of similar or different sizes. The coil may be wound into a two-dimensional or three-dimensional solenoid and/or a toroid. Opposing ends of the solenoid or toroid may be arranged to oppose each other. The coil for the solenoid and/or toroid may include an even number of wires or strips at least two of which may generate the waves defining at least partially opposite phase angles. At least two of the counter units disposed adjacent (or close) to each other may be separated by at least one electric insulator as the units may not be coated by an insulative material, may contact each other when at least one of the units may be coated by the insulative material, and the like.

The counter unit may form an uniform shape and/or size along at least its substantial portion in a direction of its longitudinal axis, may have shapes and/or sizes varying in the direction, and the like. At least two of the counter units may electrically couple with each other in a series, parallel or hybrid pattern. At least two of the counter units may define longitudinal axes and may not electrically couple with each other in at least substantial portions along the axes. At least one of the counter units may enclose therein at least a portion of another counter units in a concentric arrangement, may extend (or be braided) along with the portion of another counter unit in a paired arrangement, and the like. Such a counter member (or unit) may define at least one junction and/or bifurcation therealong. The counter member may include therealong multiple layers at least two of which may operate as at least two of the counter units. The counter member (or unit) may include multiple portions which may couple with each other in series and/or parallel patterns or which may not be coupled to each other. The system may include multiple counter members (or units) which may be coupled to each other in series and/or parallel patterns or which may not be coupled to each other. At least two portions of the counter unit or at least two counter units of the counter member may extend in the same direction while forming a series coupling, where such currents or signals may flow therein with the same amplitude. At least two portions of the counter unit or at least two counter units of the counter member may extend in the same direction while forming a parallel coupling, where the currents or signals may flow therein with the same amplitude or different amplitudes.

The dynamic signals may flow through at least two portions of the counter unit or at least two counter units of the counter member along the same direction but such at least two of the portions or units may also be wound in opposite directions, thereby canceling at least portions of such magnetic waves emitted thereby. Such dynamic signals may flow through at least two portions of the counter unit or at least two counter units of the counter member in opposite directions and such at least two of the portions or counter units may be wound along the same direction, thereby canceling at least portions of the magnetic waves emitted thereby. The counter member and driver member may define substantially identical, similar or different resonance frequencies. The counter member and at least one of the voice coil and magnet may have identical, similar or different resonance frequencies. At least two portions of the counter unit or at least two counter units of the counter member may also define resonance frequencies which may be different from those of the rest thereof. At least one of multiple portions of the counter unit or at least one counter unit of the counter member may define a resonance frequency different from those of the rest thereof. At least one of multiple portions of the counter unit or at least one counter unit of the counter member may also be made of and/or include a different material, define a different resonance frequency, and have a different spectrum from that of the rest of the portions of the counter unit and from that of the rest of the counter units of the counter member, respectively. At least two portions of the counter unit or at least two counter units of such a counter member may be made of and/or include at least one common material and one of such at least two portions or units may include at least one frequency-modulating agent and define such spectrum which may overlap only preset portions of the spectrum of another of such two of the units but may not overlap the rest of the spectrum thereof. The preset portions of the electromagnetic waves may include low-frequency waves having frequencies less than 300 kHz, very low-frequency waves of frequencies less than 30 kHz, ultra low-frequency waves of frequencies less than 3 kHz, extremely low-frequency waves of frequencies less than 300 Hz, carrier frequencies in a range of from about 50 Hz to about 60 Hz, and the like. At least one portion of the counter unit or at least one counter unit of the counter member may be made of and/or include at least one material irradiating infrared rays including far-infrared rays, medium-infrared rays, and near-infrared rays as the current flows therein. The rest of the electromagnetic waves may be far infrared rays in a frequency range from about 300 gHz to about 10 tHz, medium infrared rays in a frequency range from about 10 tHz to about 100 tHz, a near infrared rays in a frequency range from about 100 tHz to about 700 tHz, and the like.

The system may include at least one of the magnetic shields described hereinabove or in the co-pending Applications. The magnetic shields may be disposed in, on, over, around, and/or through at least one of the members. The magnetic shields may define shapes at least partially conforming to shapes of at least one of the members of the system or, in the alternative, may define shapes at least partially different from shapes of at least one of the members. The path member may define a relative magnetic permeability greater than 1,000 or 10,000. The pole of the magnet member may be a South pole. The shunt member may directly or indirectly contact the magnet member. Such a shunt member may define a relative magnetic permeability greater than 1,000, 10,000 or higher. The magnetic shields described hereinabove or disclosed in the co-pending Applications may also be incorporated into any of the prior art devices and define novel systems of this invention. The system may further include at least one of the electric shields described hereinabove or in the co-pending Applications. The electric shields described hereinabove or disclosed in the co-pending Applications may be incorporated into any of the prior art devices and define novel systems of this invention. Such magnetic and/or electric shields may form shapes and/or sizes which may be maintained uniform along a longitudinal axis of at least one of the members or which may vary therealong. Such shapes and/or sizes of the magnetic shields and/or electric shields may be identical to, similar to or different from those of at least one of the members. The system may include multiple magnetic and/or electric shields. At least two of such magnetic and/or electric shields may shield against the magnetic waves and/or electric waves having same or different frequencies in same or different extents. The magnetic and/or electric shields may be disposed over at least a portion (or entire portion) of at least one of the members. The system may include the counter member and at least one of the electric shields and magnetic shields. At least one of the members may operate on AC or DC.

Unless otherwise specified, various features of one embodiment of one aspect of the present invention may apply interchangeably to other embodiments of the same aspect of this invention and/or embodiments of one or more of other aspects of this invention. Therefore, the counter member or unit of FIG. 1B may correspond to any of those exemplified in FIGS. 2A to 2X, and may also be disposed in any of the portions of the EMC speaker system exemplified in FIGS. 3A to 3L. In addition, the counter member of FIG. 2L may define an array of multiple counter units of various shapes described above. Similarly, each of the counter members or units shown in FIGS. 2M to 2R may correspond to any of the counter members or units exemplified in FIGS. 2A to 2L.

As described hereinabove, the EMC speaker system may include a control member which may be arranged to manipulate various operations of the system, in particular, an operation for canceling the desired portion of the harmful waves irradiated by the wave source of the system. To this end, the control member may perform various control operations such as, e.g., manipulating the amplitudes and/or directions of the dynamic signals supplied to the counter member, sensing the harmful waves and manipulating the counter member to emit the counter waves accordingly, offering various options to the user for selecting a suitable canceling operation, and the like.

Various EMC speaker systems of this invention may operate on the AC power while canceling the preset portion of the harmful EM waves with their counter members. When desirable, such EMC speaker systems may also operate on the DC power while similarly canceling the preset portion of the harmful waves. It is to be understood that the systems may also employ any conventional modalities capable of shielding and/or canceling such harmful waves. Therefore, it is preferable that any extra wires other than the counter members or counter units may be braided, bundled, and/or concentrically fabricated in order to minimize irradiation of the harmful waves.

It is to be understood that, while various aspects and embodiments of the present invention have been described in conjunction with the detailed description thereof, the foregoing description is intended to illustrate and not to limit the scope of the invention, which is defined by the scope of the appended claims. Other embodiments, aspects, advantages, and modifications are within the scope of the following claims.

What is claimed is:

1. An electromagnetically-countered speaker system for generating audible sounds based on at least one dynamic signal supplied to at least two electromagnets while minimizing irradiation of harmful electromagnetic waves onto an user of said system comprising:

at least one drive member which is configured to include at least one first electromagnet and a mobile cone, wherein said mobile cone is configured to be fixedly coupled to said first electromagnet, and wherein said first electromagnet is configured to receive a first signal of a first amplitude therein in a first preset direction and to generate first dynamic magnetic fields therearound; and at least one counter member including at least one second electromagnet which is configured to be disposed in a preset relation to said first electromagnet and to receive a second signal having a second amplitude therein in a second preset direction and to generate second dynamic magnetic fields therearound, wherein said first and second magnetic fields are configured to generate one of repulsive and attractive forces therebetween primarily based upon said relation, amplitudes, and directions, wherein magnitudes of said forces are configured to be decided based upon a preset proportion to amplitudes of at least one of said first and second signals, wherein said drive member is configured to generate vibration of said cone primarily based on said forces, to convert said vibration of said cone into said sounds, and to transmit said sounds onto said user while irradiating said harmful waves, and wherein said counter member is configured to irradiate counter electromagnetic waves capable of canceling at least a portion of said harmful waves based upon said relation, amplitudes, and directions, thereby minimizing said irradiation.

2. The system of claim 1, wherein said drive member is configured to not include any permanent speaker magnet therein.

3. The system of claim 2 which is configured to generate said at least one of said forces solely by said first and second electromagnets.

4. The system of claim 3 which is configured to generate said sounds solely by said forces.

5. The system of claim 1, wherein said drive member is configured to include therein at least one permanent speaker magnet capable of generating static magnetic fields therearound.

6. The system of claim 5 which is configured to generate at least a portion of said at least one of said forces in cooperation with at least one of said electromagnets.

7. The system of claim 1, wherein said second electromagnet is configured to be disposed one of closer to and farther away from said user than said first electromagnet during use of said system.

8. The system of claim 1, wherein said second electromagnet is configured to have at least one of a configuration and an arrangement each of which is configured to conform to a configuration and an arrangement of said first electromagnet, respectively.

9. The system of claim 8, wherein said first electromagnet is configured to be shaped into a first coil and wherein said second electromagnet is configured to be shaped into a second coil disposed in said preset relation to said first coil.

10. The system of claim 8, wherein said second electromagnet is configured to be disposed along a straight line defined between said user and first electromagnet.

11. The system of claim 1 further comprising a plurality of second electromagnets at least one of which is configured to have at least one of a configuration and an arrangement each of which is then configured to conform to a configuration and an arrangement of said first electromagnet, respectively.

12. The system of claim 11, wherein at least two of said second electromagnets are configured to be disposed around and to enclose therein at least a portion of said first electromagnet.

13. The system of claim 11, wherein at least two of said second electromagnets are configured to be concentrically disposed around and to enclose therein at least a portion of said first electromagnet.

14. The system of claim 1, wherein said counter waves are configured to define an phase angle which is at least partially opposite to that of said harmful waves for said canceling and minimizing.

15. The system of claim 1 further comprising at least one insert which is configured to include at least one material which is one of magnetically hard and soft, to be disposed inside and along said second electromagnet, and to augment said at least one of said forces.

16. The system of claim 1 which is configured to be fabricated into a speaker including said drive and counter members, an earphone including said speaker therein, a headphone including therein said speaker, and a speaker assembly formed as a single article and including a plurality of said speakers therein.

17. A method of generating audible sounds based upon at least one dynamic signal by vibrating a cone coupling to at least one first electromagnet of an electromagnetically-countered speaker system while irradiating harmful electromagnetic waves onto an user of said system but capable of minimizing said irradiating said harmful waves with at least one second electromagnet of said system comprising the steps of:

disposing said second electromagnet in a preset relation to said first electromagnet;

flowing said signals of preset amplitudes along said electromagnets in preset directions while providing at least one of repelling and attracting forces therebetween;

irradiating said harmful waves from said first electromagnet during said flowing;

emitting counter electromagnetic waves from said second electromagnet during said flowing;

vibrating said first electromagnet as well as said cone coupled thereto by said forces, thereby generating said sound while irradiating said harmful waves from said first electromagnet; and manipulating said relation, amplitudes, and directions for attaining maximum magnitudes of said forces and for matching magnitudes of said harmful waves with magnitudes of said counter waves, thereby canceling at least a substantial (or only a selected) portion of said harmful waves with said counter waves while minimizing said irradiating said harmful waves.

18. The method of claim 17 further comprising the steps of:

including no permanent speaker magnet; and generating said at least one of said forces solely by said first and second electromagnets.

19. The method of claim 17 further comprising the steps of:

forming at least one insert of a material which is one of magnetically hard and soft;

inserting said insert into and along said second electromagnet; and augmenting said at least one of said forces while miniaturizing said second electromagnet.

20. An electromagnetically-countered speaker system for generating audible sounds based on at least one dynamic signal supplied to at least one first electromagnet of a drive member of said system and to at least one second electromagnet of a counter member thereof while minimizing irradiation of harmful electromagnetic waves irradiated by said first electromagnet toward an user by canceling at least a substantial portion (or only selected portion) of said harmful waves by counter electromagnetic waves irradiated by said second electromagnet made by a process comprising the steps of:

providing said drive member with a movable part coupling with said first electromagnet;

configuring said first electromagnet to flow a first signal in a first direction therein;

configuring said second electromagnet to flow a second signal in a second direction therein;

disposing said second electromagnet away from said first electromagnet and also in a preset relation thereto;

flowing said signals along said electromagnets, thereby generating interacting magnetic fields around said electromagnets and exerting at least one of repulsive and attractive forces between said electromagnets while irradiating said harmful waves by said first electromagnet;

moving said movable part by said forces, thereby generating said sounds;

configuring said second electromagnet to irradiate counter electromagnetic waves when said second signal flows therein;

controlling amplitudes and said directions of said signals to manipulate said counter waves to define preset configurational and phase characteristics;

controlling said relation between said electromagnets to manipulate said characteristics of said counter waves to at least partially oppose those of said harmful waves; and propagating said counter waves against said harmful waves, thereby attaining said canceling and minimizing.

* * * * *